United States Patent
Power et al.

(10) Patent No.: US 9,642,874 B2
(45) Date of Patent: *May 9, 2017

(54) COMPOSITIONS OF SELENOORGANIC COMPOUNDS AND METHODS OF USE THEREOF

(71) Applicant: Alltech, Inc., Nicholasville, KY (US)

(72) Inventors: Ronan Power, Lexington, KY (US); Zi-Jian Lan, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/855,128

(22) Filed: Sep. 15, 2015

(65) Prior Publication Data

US 2016/0045533 A1 Feb. 18, 2016

Related U.S. Application Data

(63) Continuation-in-part of application No. PCT/US2014/029542, filed on Mar. 14, 2014.

(51) Int. Cl.
| | | |
|---|---|---|
| *A61K 31/7076* | (2006.01) | |
| *A61K 38/05* | (2006.01) | |
| *A61K 31/7135* | (2006.01) | |
| *A61K 31/28* | (2006.01) | |
| *A61K 38/28* | (2006.01) | |

(52) U.S. Cl.
CPC .......... *A61K 31/7135* (2013.01); *A61K 31/28* (2013.01); *A61K 31/7076* (2013.01); *A61K 38/05* (2013.01); *A61K 38/28* (2013.01)

(58) Field of Classification Search
CPC .. A61K 31/095; A61K 31/52; A61K 31/7076; A61K 36/064; A61K 38/05
See application file for complete search history.

(56) References Cited

U.S. PATENT DOCUMENTS

| | | | |
|---|---|---|---|
| 8,865,763 B2 | 10/2014 | Lyons et al. | |
| 2006/0198906 A1 | 9/2006 | Majeed et al. | |
| 2007/0077238 A1* | 4/2007 | Teo | A61K 33/04 424/93.45 |
| 2007/0122491 A1 | 5/2007 | Lyons et al. | |
| 2008/0107755 A1* | 5/2008 | Lyons | A61K 33/04 424/702 |
| 2012/0094947 A1 | 4/2012 | Lubin et al. | |
| 2015/0057243 A1 | 2/2015 | Zhou et al. | |
| 2016/0082033 A1 | 3/2016 | Power et al. | |
| 2016/0090397 A1 | 3/2016 | Zhou et al. | |

FOREIGN PATENT DOCUMENTS

| | | |
|---|---|---|
| WO | 2013151975 A1 | 10/2013 |
| WO | 2014144776 A1 | 9/2014 |
| WO | 2015137983 A1 | 9/2015 |

OTHER PUBLICATIONS

Preud'homme, H., et al., "Large Scale identification of selenium metabolites by online size-exclusion-reversed phase iquid chromatography with combined inductively coupled plasma (ICP-MS) and electrospray ionization linear trap-Orbitrap mass spectrometry (ESI-MS(n))", Metallomics, May 2012, vol. 4 (5), pp. 422-432.
Pieczenik, S. R., et al., "Mitochondrial dysfunction and molecular pathways of disease", Experimental and Molecular Pathology, 2007, vol. 83, pp. 84-92.
Pinto, A., et al., "Supranutritional selecnium induces alterations in molecular targets related to energy metabolism in skeletal muscle and visceral adipose tissue of pigs", Journal of Inorganic Biochemistry, 2012, vol. 114, pp. 47-54.
Amaudguilhem, C., et al., "Selenium metabolomics in yeast using complementary reversed-phase/hydrophilic ion nteraction (HILIC) liquid chromatography-electrospray hybrid quadrupole trap/Orbitrap mass spectrometry", Anal. Chim. Acta., Dec. 13, 2012 (757), pp. 26-38.
Ouerdane, L., et al., "Comprehensive speciation of low-molecular weight selenium metabolites in mustard seeds using HPLC-electrospray linear trap/Orbitrap tandem mass spectrometry", Metallomics, Sep. 2013, 5 (9), pp. 1294-1304.
Bierla, K., et al., "Comprehensive speciation of selenium in selenium-rich yeast", Trends in Analytical Chemistry, Dec. 2012, vol. 41, pp. 122-132.
Dudos, R. I., et al., "Synthesis and characterization of Se-adenosyl-L-selenohomocysteine selenoxide", J Sulphur Chem., Apr. 2015, 36(2), pp. 135-144.
Kogami, M., et al., "An efficient method for the synthesis of selenium modified nucleosides: its application in the synthesis of Se-adenosyl-L-selenomethionine (SeAM)", Organic & Biomolecular Chemistry, Aug. 2015, 13(36), pp. 9405-9417.
Bothwell, I. R., et al., "Large-Scale, Protection-Free Synthesis of Se-Adenosyl-L-selenomethionine Analogues and Their Application as Cofactor Surrogates of Methyltransferases", Org. Lett., May 2014, 16(11), pp. 3056-3059.
Singh, S., et al., "Facile Chemoenzymatic Strategies for the Synthesis and Utilization of S-Adenosyl-(L)-Methionine Analogues", Angew. Chem. Int. Ed., Mar. 2014, 53 (15), pp. 3965-3969.
SciFinder, "Kogami_2015_Org_Bio_Chem_Structures", ACS, 2015, structure 31, 1805788-83-3, 8 pages.
International Search Report for International Patent Application PCT/US2014/US2014/029542 mailed Jul. 31, 2014, 3 pages.
U.S. Appl. No. 14/855,065, filed Sep. 15, 2015, Ronan Power et al.
International Search Report and the Written Opinion for corresponding International Patent Application PCT/US2015/050476 mailed Dec. 17, 2015.
International Search Report and the Written Opinion for International Patent Application PCT/US15/50490 mailed Jan. 27, 2016.
U.S. Appl. No. 15/121,412, filed Aug. 25, 2016, Ronan Power et al.

* cited by examiner

*Primary Examiner* — Jeffrey E Russel
(74) *Attorney, Agent, or Firm* — Kilyk & Bowersox, P.L.L.C.; Valerie Calloway

(57) ABSTRACT

The present application relates to compositions comprising selenium compounds, such as 5'-Methylselenoadenosine, Se-Adenosyl-L-homocysteine, Gamma-glutamyl-methyl-seleno-cysteine, a compound of Formula (I), Formula (II), or Formula (III), and combinations thereof, and methods of using the same for modulating glucose metabolism in a subject.

34 Claims, 25 Drawing Sheets

COMPOSITIONS OF SELENOORGANIC COMPOUNDS AND METHODS OF USE THEREOF

CROSS-REFERENCE TO RELATED APPLICATION

This patent application is a continuation-in-part of International Patent Application Serial No. PCT/US2014/029542, filed 14 Mar. 2014, which application is incorporated by reference herein.

FIELD OF THE PRESENT APPLICATION

The present application relates to compositions of selenoorganic compositions and compounds and methods for their use to replace insulin, enhance insulin activity, inhibit glucose production, or modulate glucose metabolism in various biological pathways.

BACKGROUND

Selenium (Se) is an essential trace element that plays a critical role in many biological processes, such as reproduction, thyroid hormone metabolism, DNA synthesis and protection from oxidative damage and infection. Selenium is incorporated at the catalytic site of various selenium dependent enzymes such as glutathione peroxidase (GPx), thioredoxin reductases and one methionine-sulfoxidereductase. These selenoenzymes contribute to regulation of metabolic activity, immune function, antioxidant defense, intracellular redox regulation and mitochondrial function.

In addition, results in the literature indicate that different chemical forms of selenium have different bioactivities. For example, a selenozolidine was more effective at reducing the number of lung tumors than selenomethionine. (Poerschke et al, J Biochem Molecular Toxicology 2012 26:344). Barger et al. showed that mice fed different sources of selenium, for example, selenium methionine, sodium selenite and selenized yeast, had differential effects on gene expression and on specific functional pathways of mitochondrial structure and function. (Barger et al, Genes and Nutrition 2012 7:155). Selenized yeast contains many selenium and sulfur compounds but not all of the selenium compounds in selenized yeast impact biological processes. In addition, a mixture of selenium and sulfur compounds in selenized yeast have been shown to be inhibitory to each other, to negatively impact biological processes, or be toxic to cells.

Noninsulin-Dependent (Type II) Diabetes Mellitus (DM) is a disease characterized by insulin resistance in skeletal muscle, liver and fat, combined with defects in insulin secretion due to pancreatic β-cell function. Insulin resistance is a central feature of Type II diabetes. In liver, members of the Forkhead Box Class O (FOXO) gene transcription factor family become activated in their unphosphorylated state and they reside in the cell nucleus. In the nucleus, FOXO transcription factors bind to the promoter region of genes, such as Glucose 6-Phosphatase (G6PC). Together with other transcription factors, such as PGC-1α, increased transcription of G6PC occurs, thereby increasing the rate of glucose production. Glucose 6-phosphatase also catalyzes the last step in gluconeogenesis and glycogenolysis causing the release of glucose from the liver. Therefore, G6PC is important in the control of glucose homeostasis, particularly in diabetic subjects.

The apparent difference in bioactivity and availability of distinct chemical forms of selenium requires identification of compounds containing selenium that positively impact biological processes. In particular, there is a need to characterize the effects of selenium in insulin replacement, enhanced insulin activity, inhibition of glucose production, or modulation of glucose metabolism in various biological pathways. Further, there is a need to determine the effect of selenium compounds and their efficacy as insulin replacement therapies for individuals suffering from Type I or Type II diabetes.

SUMMARY OF THE INVENTION

The present disclosure provides a method of replacing insulin in a subject. The method of replacing insulin comprises administering a composition to the subject, the composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. The composition of the method may also comprise a carrier.

The present disclosure also provides a method of enhancing insulin activity in a subject. The method of enhancing insulin activity comprises administering a composition to the subject, the composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. The composition of the method may also comprise a carrier. The method of enhancing insulin activity may further comprise administering insulin or an analog or derivative thereof.

The present disclosure further provides a method of inhibiting glucose production in a subject. The method of inhibiting glucose production comprises administering a composition to the subject, the composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. The composition of the method may also comprise a carrier.

The present disclosure further provides a method of modulating glucose metabolism in a subject. The method of modulating glucose metabolism comprises: administering a composition to the subject, the composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. The composition of the method may also comprise a carrier.

In any one of the methods of replacing insulin, enhancing insulin activity, inhibiting glucose production, or modulating glucose metabolism in a subject, the composition may comprise 5'-Methylselenoadenosine, Se-Adenosyl-L-homocysteine and Gamma-glutamyl-methylseleno-cysteine. In any one of the methods of replacing insulin, enhancing insulin activity, inhibiting glucose production, or modulating glucose metabolism in a subject, the composition may comprise at least 0.1% (w/v) of 5'-Methylselenoadenosine. In any one of the methods of replacing insulin, enhancing insulin activity, inhibiting glucose production, or modulating glucose metabolism in a subject, the composition may be in a dried or capsular form.

In any one of the methods of replacing insulin, enhancing insulin activity, inhibiting glucose production, or modulating glucose metabolism in a subject, the composition may further comprise insulin or an analog or derivative thereof. In any one of the methods of replacing insulin, enhancing insulin activity, inhibiting glucose production, or modulating glucose metabolism in a subject, the composition may further comprise an insulin sensitizer, an insulin secretagogue, or an incretin mimetic. In any one of the methods of replacing insulin, enhancing insulin activity, inhibiting glucose production, or modulating glucose metabolism in a subject, the composition may exclude one or more of 5'-Methylthioadenosine, S-Adenosyl-L-homocysteine or Gamma-glutamyl-methyl-cysteine.

In any one of the methods of replacing insulin, enhancing insulin activity, inhibiting glucose production, or modulating glucose metabolism in a subject, the composition may be administered orally. In any one of the methods of replacing insulin, enhancing insulin activity, inhibiting glucose production, or modulating glucose metabolism in a subject, the 5'-Methylselenoadenosine or the compound of Formula (I) is a selenoglycoside. In any one of the methods of replacing insulin, enhancing insulin activity, inhibiting glucose production, or modulating glucose metabolism in a subject, the composition may be administered to the liver cells of the subject.

The present disclosure provides a composition comprising at least two different compounds selected from the group consisting of 5'-Methylselenoadenosine, Se-Adenosyl-L-homocysteine, Gamma-glutamyl-methylseleno-cysteine, a compound of Formula (I), a compound of Formula (II) and a compound of Formula (III), and combinations thereof. The composition may also comprise a carrier.

The present disclosure further provides a composition comprising at least three different compounds selected from the group consisting of 5'-Methylselenoadenosine, Se-Adenosyl-L-homocysteine, and Gamma-glutamyl-methylseleno-cysteine. The composition may also comprise a carrier.

The present disclosure provides a composition comprising at least 0.1% (w/v) of a compound according to Formula (I):

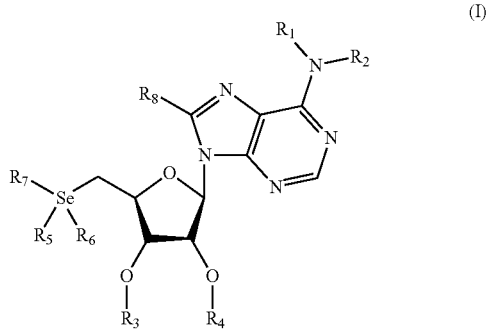

(I)

or a pharmaceutically acceptable salt, hydrate, or prodrug thereof.

$R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen.

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen.

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen.

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen.

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl.

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl.

$R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

$R_8$ is hydrogen, azido, alkyl, alkenyl, or alkynyl. The Formula (I) composition may also comprise a carrier. In addition, the 5'-Methylselenoadenosine or the compound of Formula (I) of the composition may be a selenoglycoside. The Formula (I) composition may also be administered to the liver cells of the subject.

The present disclosure also provides a composition comprising at least 0.1% (w/v) of a compound according to Formula (II):

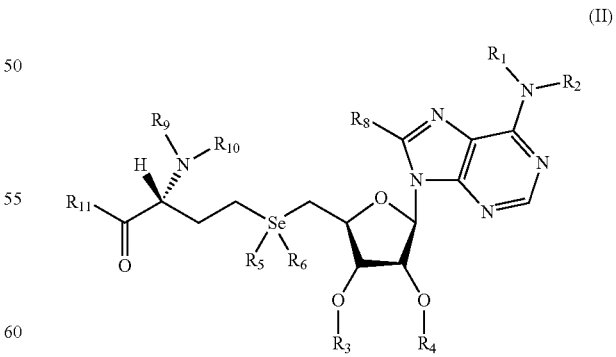

(II)

or a pharmaceutically acceptable salt, hydrate, or prodrug thereof.

$R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen.

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen.

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen.

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen.

$R_5$ is oxo, hydroxyl, alkyl, alkenyl, alkynyl, OR", or is absent; wherein R" is selected from alkyl, alkenyl, alkynyl, cycloalkyl, aryl, or aralkyl.

$R_6$ is oxo, hydroxyl, alkyl, alkenyl, alkynyl, OR", or is absent; wherein R" is selected from alkyl, alkenyl, alkynyl, cycloalkyl, aryl, or aralkyl.

$R_8$ is hydrogen, azido, alkyl, alkenyl, or alkynyl.

$R_9$ is H, acyl, alkyl, alkenyl, alkynyl, aralkyl, carboxyl, cycloalkyl, C(O)$R^c$, or C(O)O$R^c$, where $R^c$ is alkyl, cycloalkyl, aryl, aralkyl, or heterocyclyl; or $R_9$ together with $R_{10}$ form a heterocyclic ring having 4 to 8 ring members with at least one heteroatom selected from nitrogen.

$R_{10}$ is H, acyl, alkyl, alkenyl, alkynyl, aralkyl, carboxyl, cycloalkyl, C(O)$R^c$, or C(O)O$R^c$, where $R^c$ is selected from alkyl, cycloalkyl, aryl, aralkyl, or heterocyclyl; or $R_9$ together with $R_{10}$ form a heterocyclic ring having 4 to 8 ring members with at least one heteroatom selected from nitrogen.

$R_{11}$ is OR, alkoxy, aralkoxy, or amino, where R is selected from alkyl, cycloalkyl, aryl, aralkyl, or heterocyclyl.

The Formula (II) composition may comprise a carrier. The Formula (II) composition may also be administered to the liver cells of the subject.

Finally, the present disclosure provides a composition comprising at least 0.1% (w/v) of a compound according to Formula (III):

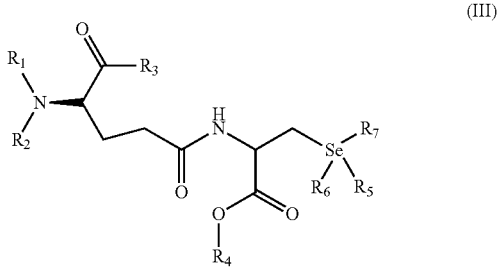

(III)

or a pharmaceutically acceptable salt, hydrate, or prodrug thereof.

$R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen.

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen.

$R_3$ is OH, OR, alkoxy, aralkoxy, or amino, where R is selected from alkyl, cycloalkyl, aryl, aralkyl, or heterocyclyl.

$R_4$ is alkyl, alkenyl, alkynyl, cycloalkyl, aryl, aralkyl, or heterocyclyl.

$R_5$ is oxo, hydroxyl, alkyl, alkenyl, alkynyl, OR", or is absent; wherein R" is selected from alkyl, alkenyl, alkynyl, cycloalkyl, aryl, or aralkyl.

$R_6$ is oxo, hydroxyl, alkyl, alkenyl, alkynyl, OR", or is absent; wherein R" is selected from alkyl, alkenyl, alkynyl, cycloalkyl, aryl, or aralkyl.

$R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

The Formula (III) composition may comprise a carrier. The Formula (III) composition may also be administered to the liver cells of the subject.

The compositions described herein may comprise at least about 0.033% (w/v) of the composition of each of two compounds or at least about 0.033% (w/v) of the composition of each of three compounds.

BRIEF DESCRIPTION OF THE DRAWINGS

A brief description of the drawings is as follows. When a mixture of selenium compounds is indicated, amount in ppb indicates the amount of ppb of selenium in each selenium compound in the mixture. When a mixture of sulfur compounds is indicated, amount in ppb indicates the amount of ppb of sulfur each sulfur compound in the mixture. For example, 150 ppb of Compounds CDE contains 150 ppb of selenium in Compound C, 150 ppb of selenium in Compound D, and 150 ppb of selenium in Compound E in combination for a total selenium concentration of 450 ppb. For example, 150 ppb of Compounds HU contains 150 ppb of sulfur in Compound H, 150 ppb of sulfur in Compound I, and 150 ppb of sulfur in Compound J in combination for a total sulfur concentration of 450 ppb.

FIG. 2A is a bar graph showing relative G6pc mRNA levels in AML-12 cells treated with a control and 150 ppb Compounds CDE and Compounds HIJ for 48 hours.

FIG. 2B is a bar graph showing relative G6pc mRNA expression in AML-12 cells treated with individual Compound C, Compound D, Compound E, Compound H, Compound I and Compound J for 48 hours.

FIG. 5A is a bar graph showing relative Insr mRNA expression levels in AML-12 cells treated with 150 ppb of Compounds CDE and 150 ppb of Compounds HIJ for 24 hours. ** $P<0.01$ when compared to control (water vehicle-treated) group.

FIG. 5B is a bar graph showing relative Igf1r mRNA expression levels in AML-12 cells treated with 150 ppb of Compounds CDE and 150 ppb of Compounds HIJ for 24 hours. ** $P<0.01$ when compared to control (water vehicle-treated) group.

FIG. 5C is a bar graph showing relative Insr mRNA expression levels in AML-12 cells treated with control, 10 or 100 nM insulin, 150 ppb or 300 ppb Compounds CDE, or cotreated with 8-CPT/Dex, insulin and Compounds CDE. *, $P<0.05$, ** $P<0.01$ when compared to control (no 8-CPT/Dex/insulin/Compounds CDE-treated) group.

FIG. 5D is a bar graph showing relative Igfr1 mRNA expression levels in AML-12 cells treated with control, 10 or 100 nM insulin, 150 ppb or 300 ppb Compounds CDE, or cotreated with 8-CPT/Dex, insulin and Compounds CDE. *, $P<0.05$, ** $P<0.01$ when compared to control (no 8-CPT/Dex/insulin/Compound CDE-treated) group.

FIG. 6A is a Western blot showing protein expression of various signaling molecules, including pFoxo3T32 and pFoxo4T28, in response to treatment of AML-12 cells with a water control or 150 ppb of Compounds CDE and 150 ppb of Compounds HIJ for 6 hours.

FIG. 6B is a bar graph showing quantitative analysis of pFoxo3T32 protein levels in the gel of FIG. 6A.

FIG. 6C is a bar graph showing quantitative analysis of pFoxo4T28 protein levels in the gel of FIG. 6A.

FIG. 7A is a Western blot showing protein expression of various signaling molecules, including pFoxo3T32 and pFoxo4T28, in response to treatment of AML-12 cells with a water control or 150 ppb of Compounds CDE, 150 ppb of Compounds CE, and 150 ppb of Compounds DE for 6 hours.

FIG. 7B is a bar graph showing quantitative analysis of pFoxo3T32 protein levels in the gel of FIG. 7A.

FIG. 7C is a graph showing quantitative analysis of pFoxo4T28 protein levels in the gel of FIG. 7A.

FIG. 9A is a bar graph showing relative glucose levels in the culture media of mouse hepatocyte cells treated with control, 8-CPT/Dex, 10 or 100 nM insulin, 150 ppb or 300 ppb Compounds CDE, and combinations of insulin and Compounds CDE. * $P<0.05$ vs vehicle treatment group (the first bar in the graphs).

FIG. 9B is a bar graph showing relative G6pc mRNA levels in mouse hepatocyte cells treated with control, 10 or 100 nM insulin, 150 ppb or 300 ppb Compounds CDE, and combinations of insulin and Compounds CDE. * $P<0.05$ vs vehicle treatment group (the first bar in the graphs).

FIG. 9C is a bar graph showing relative LDH levels in the culture media of mouse hepatocyte cells treated with control, 10 or 100 nM insulin, 150 ppb or 300 ppb Compounds CDE, and combinations of insulin and Compounds CDE.

FIG. 10A is a bar graph showing relative glucose levels in the culture media of mouse hepatocyte cells treated with control, 8-CPT/Dex, combinations of 8-CPT/Dex and insulin or Compounds CDE, and combinations of 8-CPT/Dex, insulin and Compounds CDE.

FIG. 10B is a bar graph showing relative G6pc mRNA levels in mouse hepatocyte cells treated with control, 8-CPT/Dex, combinations of 8-CPT/Dex and insulin or Compounds CDE, and combinations of 8-CPT/Dex, insulin and Compounds CDE.

FIG. 10C is a bar graph showing relative LDH levels in the culture media of mouse hepatocytes treated with control, 8-CPT/Dex, combinations of 8-CPT/Dex and insulin or Compounds CDE, and combinations of 8-CPT/Dex, insulin and Compounds CDE. * $P<0.05$ vs vehicle treatment group (the first bar in the graph).

FIG. 11A is a bar graph showing relative glucose levels in the culture media of mouse hepatocyte treated with basal control (water vehicle), 10 or 100 nM insulin (Ins), 150 ppb or 300 ppb Compounds CDE, and combinations of insulin and Compounds CDE in the presence or absence of 8-CPT/Dex for 6 hours. # $P<0.05$ vs basal control group (the first bar in the graph). * $P<0.05$ vs the 8-CPT/Dex treatment group (the first filled bar in the graph).

FIG. 11B is a bar graph showing relative LDH levels in the culture media of mouse hepatocyte cells treated with basal control (water vehicle), 10 or 100 nM insulin (Ins), 150 ppb or 300 ppb Compounds CDE, and combinations of insulin and Compounds CDE in the presence or absence of 8-CPT/Dex for 6 hours.

(pFoxo1T24), Foxo3 at threonine 32 (pFoxo3T32), Foxo4 at threonine 28 (pFoxo4T28), and Gsk3b at serine 9 (pGsk3bS9) in primary mouse hepatocytes.

Figure 12A:
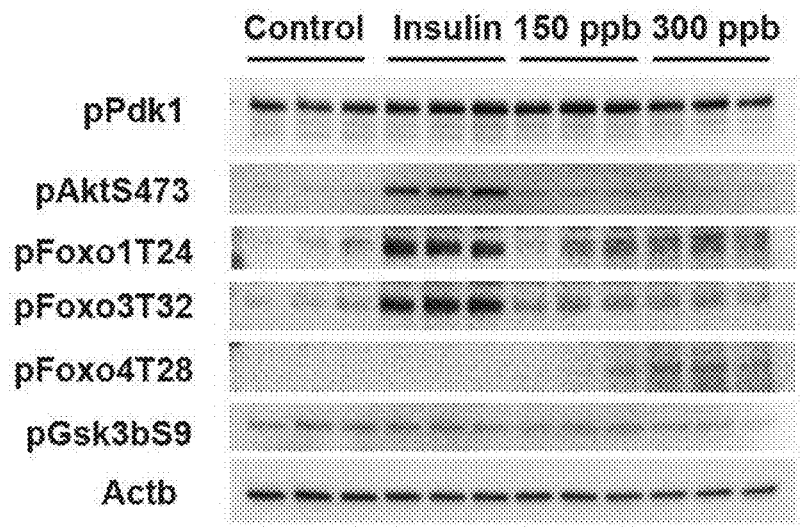
FIGS. 12A-12F show the effect of Compounds CDE on protein expression levels of phosphorylated Pdk1 (pPdk1), Akt at serine 473 (pAktS473), Foxo1 at threonine 24

FIG. 12A is a Western blot showing the effect of a control, insulin, or 150 ppb or 300 ppb Compounds CDE on protein levels of pPdk1, pAktS473, pFoxo1T24, pFoxo3T32, pFoxo4T28, and pGsk3bS9 in primary mouse hepatocytes.

Figure 12B:
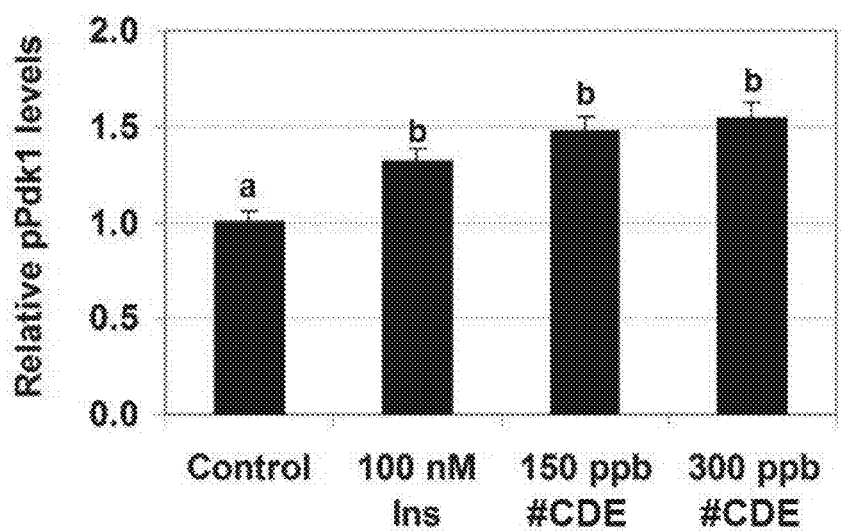

FIG. 12B is a bar graph showing the relative pPdk1 protein levels in mouse hepatocytes treated with a control, 100 nM of insulin, or 150 ppb or 300 ppb Compounds CDE.

Figure 12C:
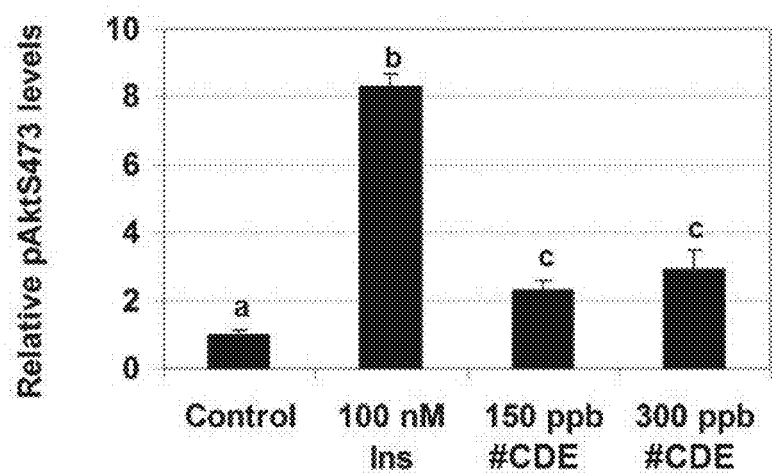

FIG. 12C is a bar graph showing the relative pAktS473 protein levels in mouse hepatocytes treated with a control, 100 nM of insulin, or 150 ppb or 300 ppb Compounds CDE.

Figure 12D:
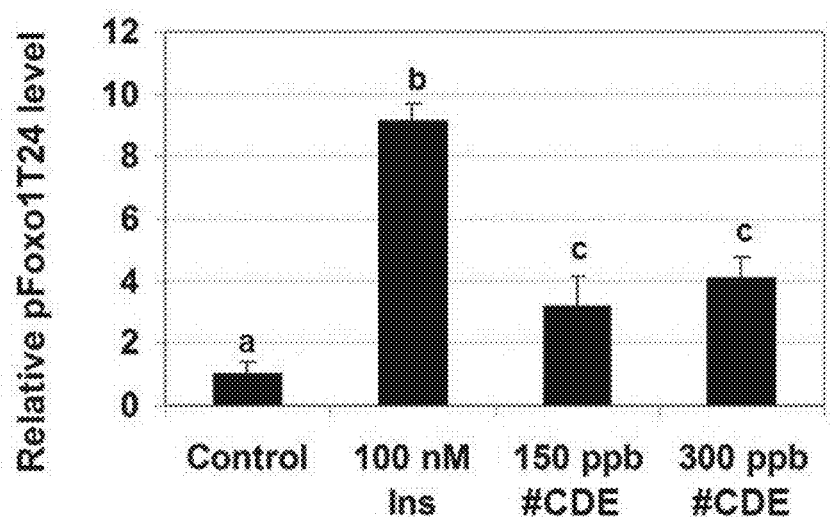

FIG. 12D is a bar graph showing the relative pFoxo1T24 protein levels in mouse hepatocytes treated with a control, 100 nM of insulin, or 150 ppb or 300 ppb Compounds CDE.

Figure 12E:
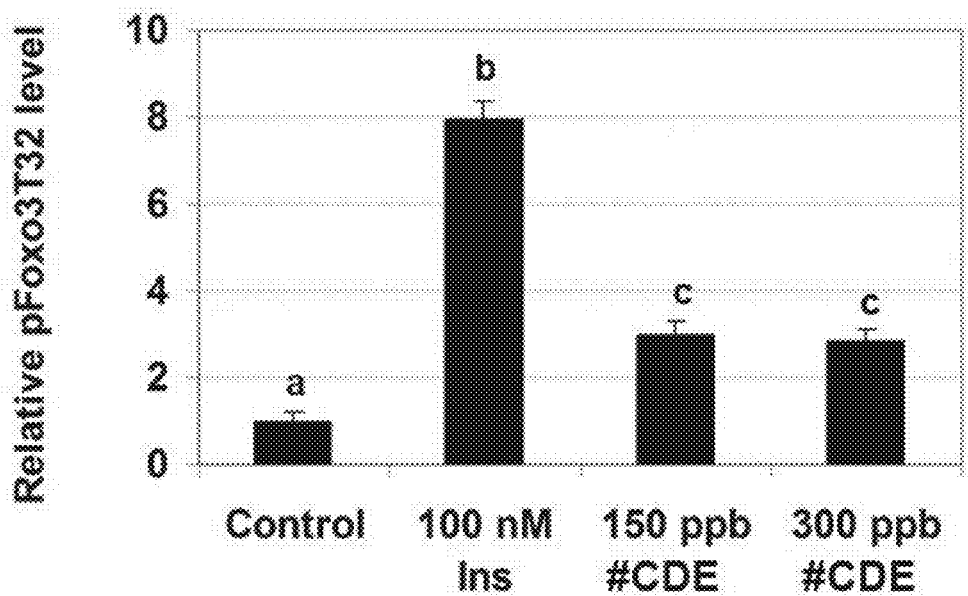

FIG. 12E is a bar graph showing the relative pFoxo3T32 protein levels in mouse hepatocytes treated with a control, 100 nM of insulin, or 150 ppb or 300 ppb Compounds CDE.

Figure 12F:
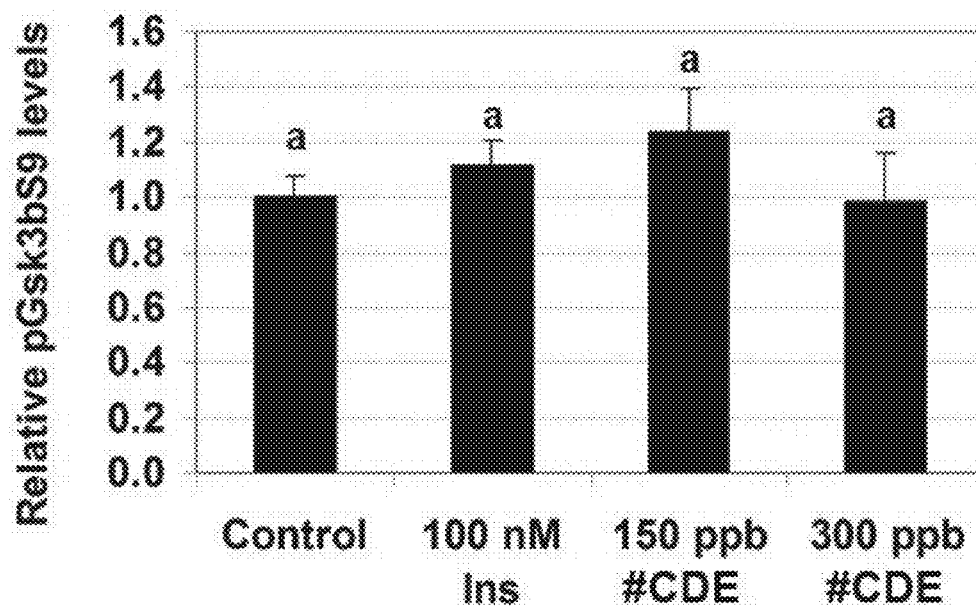

FIG. 12F is a bar graph showing the relative pGsk3bS9 protein levels in mouse hepatocytes treated with a control, 100 nM of insulin, or 150 ppb or 300 ppb Compounds CDE.

FIGS. 13A-13D show the time-effect of Compounds CDE treatment on protein expression levels of phosphorylated Pdk1, Akt, Foxo1 and Foxo3 in primary mouse hepatocytes cultured under serum-free conditions.

Figure 13A:
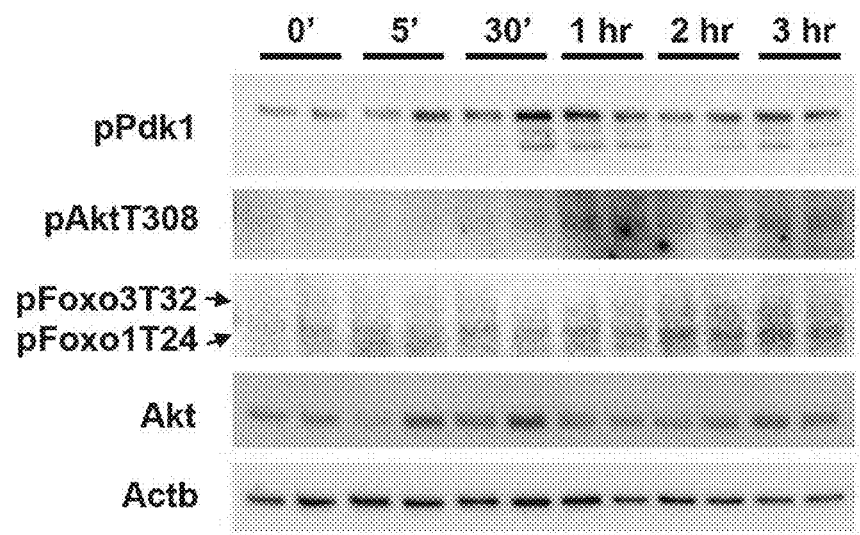

FIG. 13A is a Western blot showing the effect of Compounds CDE treatment for 0 minute, 5 minutes, 30 minutes, 1 hour, 2 hours, and 3 hours on protein levels of pPdk1, pAktT308, pFoxo1T24, pFoxo3T32, Akt, and Actb in primary mouse hepatocytes.

Figure 13B:
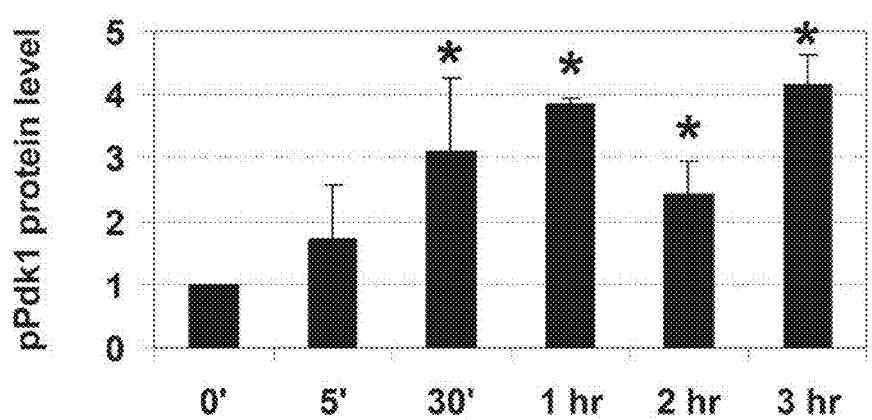

FIG. 13B is a bar graph showing the relative pPdk1 protein levels after treatment of mouse hepatocytes with Compounds CDE for 0 minute, 5 minutes, 30 minutes, 1 hour, 2 hours, and 3 hours. * P at least <0.05 when compared to no compounds CDE treatment (0 minute group).

Figure 13C:
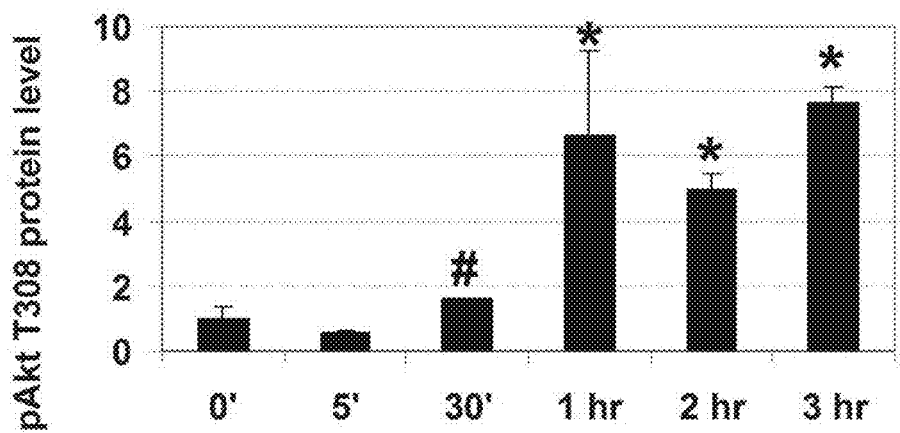

FIG. 13C is a bar graph showing the relative pAktT308 protein levels after treatment of mouse hepatocytes with Compounds CDE for 0 minute, 5 minutes, 30 minutes, 1 hour, 2 hours, and 3 hours. #P<0.15, * P at least <0.05 when compared to no compounds CDE treatment (0 minute group).

Figure 13D:
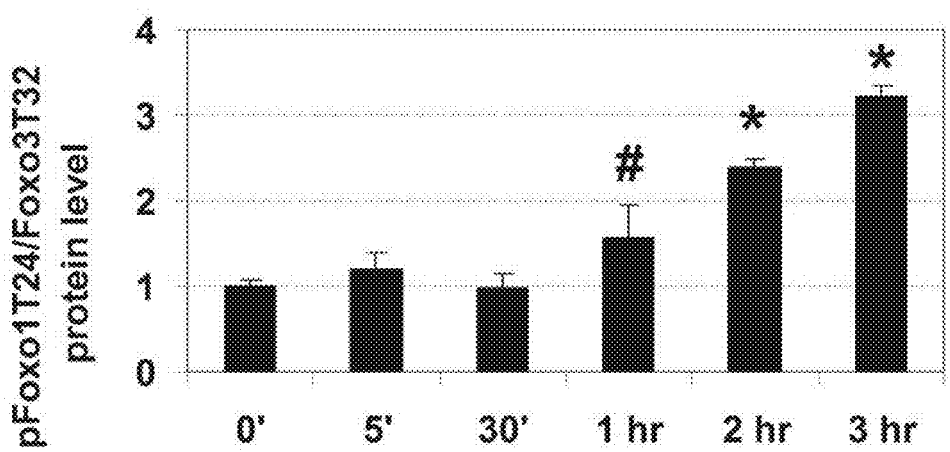

FIG. 13D is a bar graph showing the combined pFoxo1T24 and pFoxo3T32 protein levels after treatment of mouse hepatocytes with Compounds CDE for 0 minute, 5 minutes, 30 minutes, 1 hour, 2 hours, and 3 hours. #P< 0.15, * P at least <0.05 when compared to no compounds CDE treatment (0 minute group).

Figure 14A:
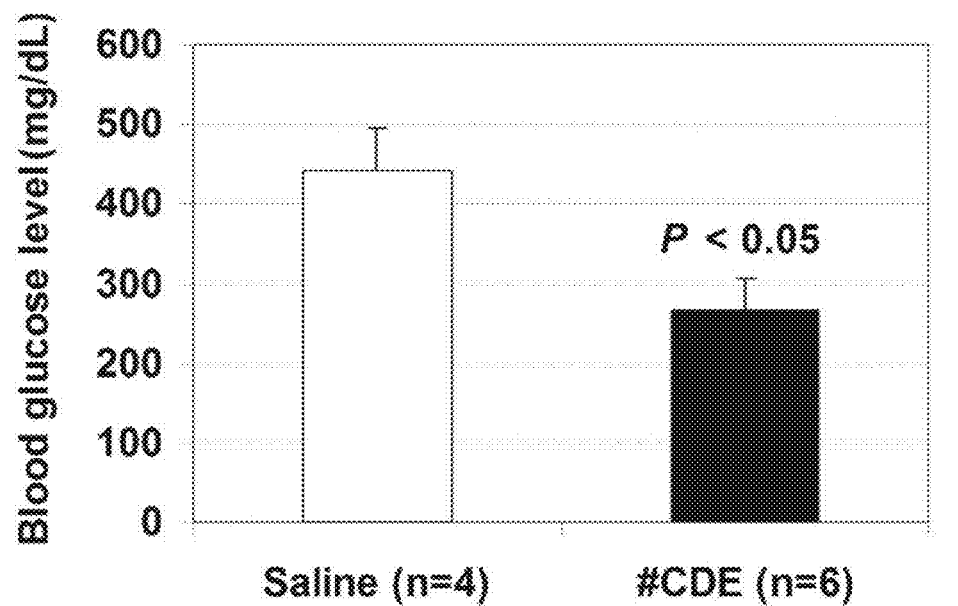
Figure 14B:
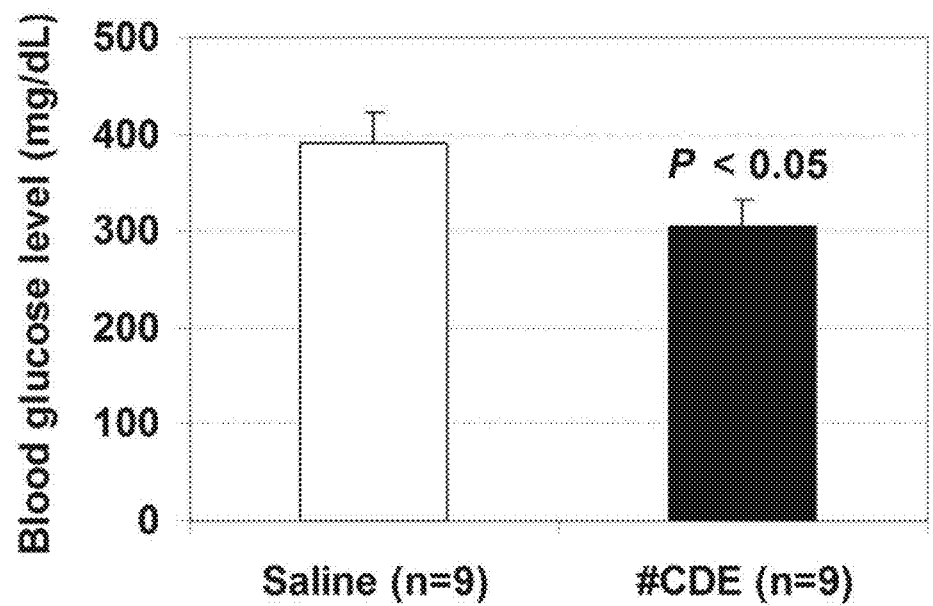

FIGS. 14A-14B show the effect of Compounds CDE on blood glucose levels in Lepr$^{db/db}$ mice.

FIG. 14A is a bar graph showing the blood glucose levels in Lepr$^{db/db}$ mice after intraperitoneally injected with physiological saline or Compounds CDE every other day from the mouse age of 27 days to 3.5 months.

FIG. 14B is a bar graph showing the blood glucose levels in Lepr$^{db/db}$ mice after intraperitoneally injected with physiological saline or Compounds CDE daily from the mouse age of 38 days to 66 days.

Figure 15A:
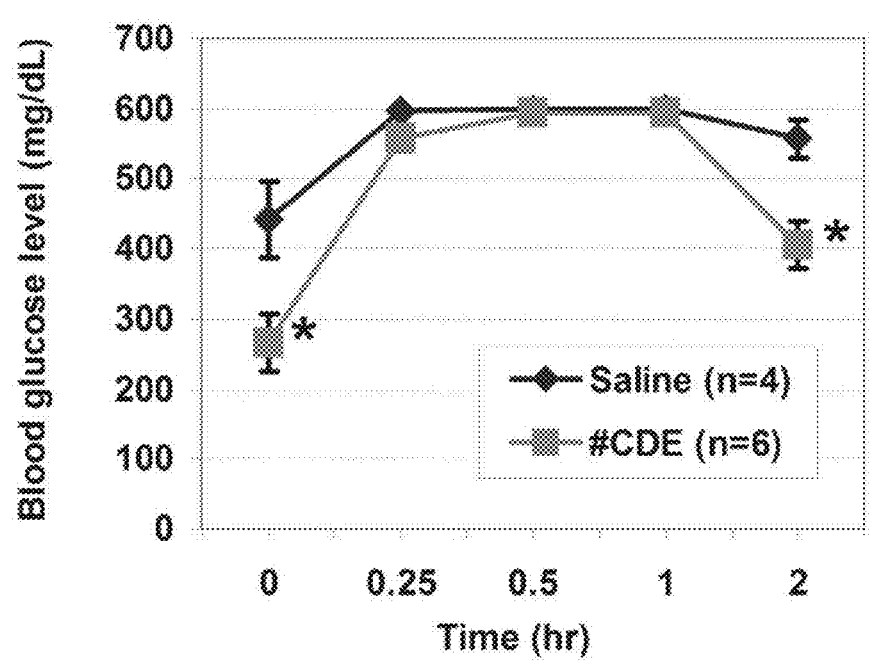
Figure 15B:
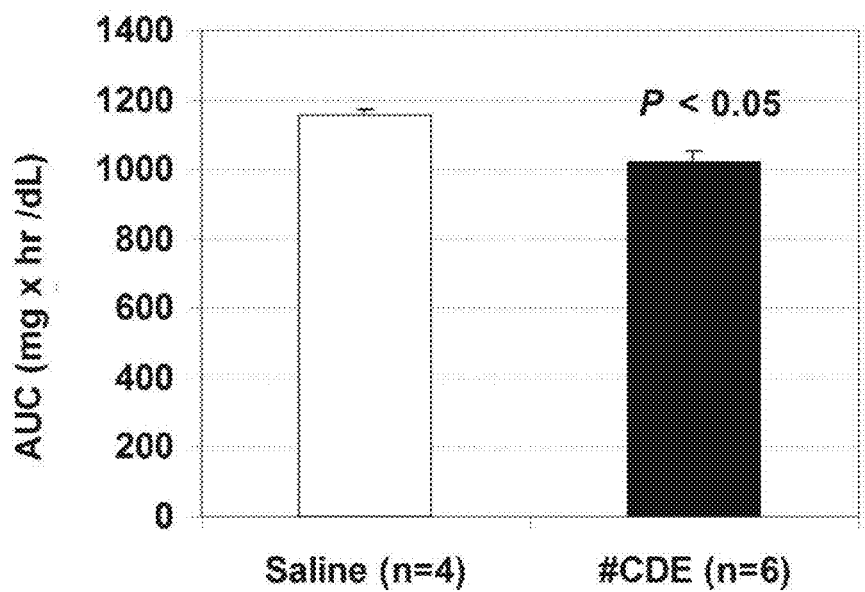

FIGS. 15A-15B show the effect of Compounds CDE on glucose tolerance in Lepr$^{db/db}$ mice after intraperitoneally injected with physiological saline or Compounds CDE every other day from the mouse age of 27 days to 3.5 months.

FIG. 15A is a graph showing the effect of Compounds CDE on blood glucose levels in saline- and Compounds CDE-treated Lepr$^{db/db}$ mice at zero time point (determined immediately before the injection of glucose) and various time points (0.25 hour, 0.5 hour, 1 hour and 2 hours) after the glucose injections. * P refers to at least <0.05 when compared to saline-treated group at the same time point.

FIG. 15B is a graph showing the quantitative analysis of the area under the curve (AUC) of the graph in FIG. 15A.

DETAILED DESCRIPTION

Definitions

As used herein, the terms "administration" and "administering" refer to the act of giving a drug, prodrug, or other agent, or therapeutic treatment (e.g., compositions of the present application) to a subject in vivo, in vitro or to ex vivo cells, tissues, and organs. The compounds and compositions of the present disclosure may be given to a subject by any route of administration known in the art. Exemplary routes of administration to the human body can be through the eyes (ophthalmic), mouth (oral), skin (topical or transdermal), nose (nasal), lungs (inhalant), oral mucosa (buccal), brain, ear, rectal, vaginal, or by injection. Routes of injection may be administered intravenously, subcutaneously, intratumorally, intraperitoneally, and the like.

The term "alkyl" refers to a branched or unbranched saturated hydrocarbon group of 1 to 24 carbon atoms, and preferably, at least three carbon atoms. In some embodiments, an "alkyl" group contains 1 to 16 carbon atoms (i.e., $C_{1-16}$ alkyl), specifically, in other embodiments, the alkyl comprises 3 to 16 atoms (i.e., $C_{3-16}$ alkyl). The alkyl group may be optionally substituted with an acyl, amino, amido, azido, carboxyl, alkyl, aryl, halo, guanidinyl, oxo, sulfanyl, sulfenyl, sulfonyl, heterocyclyl or hydroxyl group. Additional examples of an alkyl group include, but are not limited to methyl, ethyl, propyl, iso-propyl, butyl, iso-butyl, secondary-butyl, tertiary-butyl, pentyl, iso-pentyl, neo-pentyl, hexyl, iso-hexyl, 3-methylpentyl, 2,3-dimethylbutyl, neohexyl, heptyl, octyl, nonyl, decyl, undecyl, dodecyl, tridecyl, tetradecyl, pentadecyl, and hexadecyl.

In one embodiment of a $C_3$-$C_{16}$ alkyl, the alkyl is not a substituted alkyl. In other embodiments, the substituted alkyl does not have both a carboxyl group and an amino group. In further embodiments, the $C_3$-$C_{16}$ alkyl is not a substituted alkyl having both a carboxyl group and an amino group.

The term "alkali metal" refers to metallic salts that include, but are not limited to, appropriate alkali metal salts (e.g., Group IA) salts, alkaline earth metal salts (e.g., Group IIA), and other physiologically acceptable metals. Metallic salts can be made from aluminum, calcium, lithium, magnesium, potassium, sodium, zinc or combinations thereof.

The term "alkenyl" refers to a straight or branched carbon chain containing at least one carbon-carbon double bond. In some embodiments, "alkenyl" refers to a hydrocarbon containing 1, 2, 3, 4, 5, 6, 7, 8, 9 or 10 carbon atoms (i.e., $C_{1-10}$ alkenyl). Examples of an alkenyl group include, but are not limited to, ethene, propene, butene, pentene, hexene, heptene, octene, nonene and decene. The alkenyl group may be optionally substituted with an amino, alkyl, halo, or hydroxyl group.

The term "amido" refers to either a C-amido group, such as a —CONR'R" moiety or an N amido group, such as —NR'COR" moiety, wherein R' and R" may independently be hydrogen, alkyl, alkenyl, alkynyl, alkoxy, carbocyclic, heterocyclic, aryl, or aralkyl. A "sulfoamido" group includes the —NR—SO$_2$—R" moiety, wherein the R' and R" may be hydrogen, alkyl, aryl, or aralkyl.

The term "alkynyl" refers to a straight or branched carbon chain comprising at least one carbon-carbon triple bond. In exemplary embodiments, "alkynyl" refers to a hydrocarbon containing 2, 3, 4, 5, 6, 7, 8, 9 or 10 carbon atoms (i.e., $C_{2-10}$ alkynyl). Examples of an alkynyl group include, but are not limited to, ethyne, propyne, butyne, pentyne, hexyne, heptyne, octyne, nonyne and decyne. The alkynyl group may be optionally substituted with an amino, alkyl, halo, or hydroxyl group.

The term "aryl" refers to a carbocyclic aromatic system comprising one, two or three rings. The rings may be attached together in a pendant manner or may be fused together. The term "aryl" encompasses aromatic groups such as phenyl, naphthyl, tetrahydronaphthyl, tetralin, indane, indene, and biphenyl. The aryl group may optionally be substituted with an amino, alkyl, halo, hydroxyl, carbocyclic, heterocyclic, or another aryl group.

A "combination" as used herein refers to a plurality of components. The combination may comprise, consist essentially of, or consist of atoms, compounds, compositions, components, constituents, elements, moieties, molecules, or mixtures. A combination includes, but is not limited to, a mixture.

The term "fused" means that a second ring is present (i.e., attached or formed) by having two adjacent atoms in common (i.e., shared) with the first ring. The term "fused" is equivalent to the terms "condensed," "attached," and "bound," which may be used interchangeably.

The term "cycloalkyl" refers to a monocyclic saturated or partially saturated carbon ring, comprising a number of ring atoms. In some embodiments, "cycloalkyl" refers to a carbon ring containing 3-12 ring atoms (i.e., $C_{3-12}$ cycloalkyl). As used herein, a cycloalkyl encompasses monocyclo, bridged, spiro, fused, bicyclo and tricyclo ring structures. Examples of a cycloalkyl group include, but are not limited to, cyclopropyl, cyclobutyl, cyclopentyl, cyclopentenyl, cyclohexyl, cyclohexenyl, cycloheptyl, cycloheptenyl, norbornyl, decalin, adamantyl, and cyclooctyl. The cycloalkyl group may be optionally substituted with an amino, alkyl, halo, or hydroxyl group.

The term "aralkyl" refers to aryl-substituted alkyl moieties. Aralkyl groups may be "lower aralkyl" groups, where the aryl groups are attached to alkyl groups having one to six carbon atoms. Examples of aralkyl groups include benzyl, diphenylmethyl, triphenylmethyl, phenylethyl, and diphenylethyl. The terms "benzyl" and "phenylmethyl" are interchangeable. In some embodiments, the alkyl is a $C_3$-$C_{16}$ alkyl. In other embodiments, the alkyl is not a substituted alkyl having both a carboxyl group and an amino group.

The term "aryloxy" refers to an aryl group attached to an oxygen atom. The aryloxy group may optionally be substituted with a halo, hydroxyl, or alkyl group. Examples of such groups include, but are not limited to, phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy) phenoxy.

The term "alkoxy" refers to an oxy-containing group substituted with an alkyl or cycloalkyl group. Examples of an alkoxy group include, without limitation, methoxy, ethoxy, tert-butoxy, and cyclohexyloxy. "Lower alkoxy" groups have one to six carbon atoms, and include, but are not limited to, methoxy, ethoxy, propoxy, butoxy, isopropoxy, and tert-butoxy groups.

The term "aralkoxy" refers to an oxy-containing aralkyl group attached through an oxygen atom to other groups. "Lower aralkoxy" groups are phenyl groups attached to a lower alkoxy group. Examples of a lower aralkoxy group includes, but is not limited to, benzyloxy, 1-phenylethoxy, 3-trifluoromethoxybenzyloxy, 3-trifluoromethylbenzyloxy, 3,5-difluorobenyloxy, 3-bromobenzyloxy, 4-propylbenzyloxy, 2-fluoro-3-trifluoromethylbenzyloxy, and 2-phenylethoxy.

The term "acyl" refers to a —C(=O)R moiety, wherein R is hydrogen, alkyl, alkenyl, alkynyl, carbocyclic, heterocylic, aryl, or aralkyl. Preferably, R is hydrogen, alkyl, aryl, or aralkyl.

The term "carboxyl" refers to a —R'C(=O)OR" moiety, wherein R' and R" are independently hydrogen, alkyl, alkenyl, alkynyl, carbocyclic, heterocylic, heterocyloalkyl, aryl, ether, or aralkyl. R can additionally be a covalent bond. A "carboxyl" includes both carboxylic acids, and carboxylic acid esters.

The term "carboxylic acid" refers to a carboxyl group in which R' is hydrogen or a salt. Carboxylic acids include, but are not limited to, formic acid, acetic acid, propionic acid, butyric acid, valeric acid, 2-methyl propionic acid, oxiranecarboxylic acid, and cyclopropane carboxylic acid.

The term "carboxylic acid ester" or "ester" refers to a carboxyl group in which R" is alkyl, alkenyl, alkynyl, carbocyclic, heterocylic, aryl, or aralkyl. Examples of carboxylic acids include, but are not limited to, formic acid, acetic acid, propionic acid, butanoic acid, pentanoic acid, hexanoic acid, heptanoic acid, octanoic acid, nonanoic acid, decanoic acid, cyclopropanecarboxylic acid, cyclobutanecarboxylic acid, cyclopentanecarboxylic acid, cyclohexanecarboxylic acid, cycloheptanecarboxylic acid, cyclooctanecarboxylic acid, or cyclononanecarboxylic acid.

The term "carbonyl" refers to refers to a C=O moiety, also known as an "oxo" group.

The term "heterocycle" or "heterocyclyl" or "heterocyclic ring" refers to an aromatic or non-aromatic cyclic hydrocarbon with 3 to 12 carbon atoms. In exemplary embodiments, "heterocyclyl" refers to a cyclic hydrocarbon containing 3, 4, 5, or 6 ring atoms (i.e., $C_{3-6}$ heterocyclyl). The heterocycle may optionally be substituted, saturated, or unsaturated. Typically, at least one of the ring atoms is an Oxygen (O), Nitrogen (N), Sulfur (S), Phosphorous (P), or Selenium (Se). For example, in some embodiments, a ring N atom from the heterocyclyl is the bonding atom to a —C(O) moiety to form an amide, a carbamate, or a urea. Examples of a heterocyclic group include, but are not limited to, aziridine, oxirane, thiirane, azetidine, oxetane, thietane, pyrrolidine, imidazole, tetrahydrofuran, pyran, thiopyran, thiomorpholine, thiomorpholine S-oxide, oxazoline, tetrahydrothiophene, piperidine, tetrahydropyran, thiane, imidazolidine, oxodioxolenyl, oxazolidine, thiazolidine, dioxolane, dithiolane, piperazine, oxazine, dithiane, dioxane, pyridinyl, furanyl, benzofuranyl, isobenzofuranyl, pyrrolyl, thienyl, 1,2,3-triazolyl, 1,2,4-triazolyl, indolyl, imidazolyl, thiazolyl, thiadiazolyl, pyrimidinyl, oxazolyl, triazinyl, and tetrastyla. Exemplary heterocycles include benzimidazole, dihydrothiophene, dioxin, dioxane, dioxolane, dithiane, dithiazine, dithiazole, dithiolane, furan, indole, 3-H indazole, 3-H-indole, indolizine, isoindole, isothiazole, isoxazole, morpholine, oxazole, oxadiazole, oxathiazole, oxathiazolidine, oxazine, oxadiazine, piperazine, piperidine, purine, pyran, pyrazine, pyrazole, pyridine, pyrimidine, pyrimidine, pyridazine, pyrrole, pyrrolidine, tetrahydrofuran, tetrazine, thiadiazine, thiadiazole, thiatriazole, thiazine, thiazole, thiophene, triazine, and triazole. The heterocycle may be optionally substituted with an amino, alkyl, alkenyl, alkynyl, halo, hydroxyl, carbocyclic, thio, other heterocyclic, or aryl group.

The term "heteroaryl" refers to a cyclic hydrocarbon, where at least one of a plurality of ring atoms is an O, N, S, P or Se. The ring of the heteroaryl is characterized by delocalized [pi] electrons (aromaticity) shared among the ring members. Heteroaryl moieties as defined herein may have Carbon (C), N, S, P or Se bonding hands. For example, in some embodiments, a ring N atom from the heteroaryl is the bonding atom to a —C(O) moiety to form an amide, a carbamate, or an urea. In exemplary embodiments, "heteroaryl" refers to a cyclic comprising 5 or 6 ring atoms (i.e., $C_{5-6}$ heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "hydroxy" or "hydroxyl" refers to the substituent —OH.

The term "oxo" refers to the substituent =O.

The term "nitro" refers to $NO_2$.

The term "azido" refers to $N_3$.

The term "sulfur analog(s)" refers to an analog of a compound, wherein one or more selenium atoms have been replaced by one or more sulfur atoms.

The term "sulfanyl" refers to a —SR moiety, where R is hydrogen, alkyl, alkenyl, alkynyl, carbocyclic, heterocylic, aryl, or aralkyl.

The term "sulfenyl" refers to a —SOR' moiety, where R is hydrogen, alkyl, alkenyl, alkynyl, carbocyclic, heterocylic, aryl, or aralkyl.

The term "sulfonyl" refers to a —SOR' moiety, where R refers to hydrogen, alkyl, alkenyl, alkynyl, carbocyclic, heterocylic, aryl, or aralkyl.

The term "ketone" refers to a moiety containing at least one carbonyl group where the carbonyl carbon is bound to two other carbon atoms. In exemplary embodiments, a "ketone" refers to a carbonyl-containing moiety containing 3, 4, 5, 6, 7, 8, 9 or 10 carbon atoms (i.e., $C_{3-10}$ ketone). Examples of a ketone group include, but are not limited to, acetone, butanone, pentanone, hexanone, heptanone, octanone, nonanone, decanone, cyclobutanone, cyclopentanone, cyclohexanone, cycloheptanone, cyclooctanone, cyclononanone and cyclodecanone.

The term "amino" refers to a primary, secondary or tertiary group having the formula, —NR'R," wherein R' and R" are independently hydrogen, acyl, alkyl, alkyenyl, alkynyl, aralkyl, aryl, carboxyl, cycloalkyl, heterocyclic, or another amino group (as in the case of hydrazide). R' and R," together with the nitrogen atom to which they are attached, form a ring having 4 to 8 atoms. Thus, the term "amino," includes unsubstituted, monosubstituted (e.g., monoalkylamino or monoarylamino), and disubstituted (e.g., dialkylamino or aralkylamino) amino groups Amino groups include a —$NH_2$ moiety, methylamino, ethylamino, dimethylamino, diethylamino, methyl-ethylamino, pyrrolidin-1-yl or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, imidazolyl, isoindolyl, indolyl, indazolyl, purinyl, quinolizinyl. The ring containing the amino group may be optionally substituted with another amino, alkyl, alkenyl, alkynyl, halo, or hydroxyl group.

The term "amine" refers to a primary, secondary or tertiary amino group of the formula —NR'R," wherein R' and R" as used in this definition are independently hydrogen, acyl, alkyl, alkyenyl, alkynyl, aralkyl, aryl, carboxyl, cycloalkyl, heterocyclic, or other amino (in the case of hydrazide) or R' and R" together with the nitrogen atom to which they are attached, form a ring having 4-8 atoms. Thus, the term "amino", as used herein, includes unsubstituted, monosubstituted (e.g., monoalkylamino or monoarylamino), and disubstituted (e.g., dialkylamino or aralkylamino) amino groups. Amino groups include —$NH_2$, methylamino, ethylamino, dimethylamino, diethylamino, methyl-ethylamino, pyrrolidin-1-yl or piperidino, morpholino, etc. Other exemplary "amino" groups forming a ring, include, but are not limited to, pyrrolyl, imidazolyl, pyrazolyl, isothiazolyl, isoxazolyl, pyridyl, pyrazinyl, pyrimidinyl, pyridazinyl, indolizinyl, imidazolyl, isoindolyl, indolyl, indazolyl, purinyl, quinolizinyl. The ring containing the amino group may be optionally substituted with another amino, alkyl, alkenyl, alkynyl, halo, or hydroxyl group.

The term "alcohol" refers to "hydroxy," "hydroxyl," or any substituent comprising the —OH moiety.

The term "amino alcohol" refers to a functional group containing both an alcohol and an amine group. "Amino alcohols" also refer to amino acids having a carbon bound to an alcohol in place of the carboxylic acid group. In exemplary embodiments, an "amino alcohol" comprises an amine bound to the carbon adjacent to the alcohol-bearing carbon. In exemplary embodiments, "amino alcohol" refers to an amine and an alcohol-containing moiety containing 1, 2, 3, 4, 5, 6, 7, 8, 9, 10, 11 or 12 carbon atoms (i.e., $C_{1-12}$ amino alcohol). Examples of amino alcohols include, but are not limited to, ethanolamine, heptaminol, isoetarine, norepinephrine, propanolamine, sphingosine, methanolamine, 2-amino-4-mercaptobutan-1-ol, 2-amino-4-(methylthio)butan-1-ol, cysteinol, phenylglycinol, prolinol, 2-amino-3-phenyl-1-propanol, 2-amino-1-propanol, cyclohexylglycinol, 4-hydroxy-prolinol, leucinol, tert-leucinol, phenylalaninol, a-phenylglycinol, 2-pyrrolidinemethanol, tyrosinol, valinol, serinol, 2-dimethylaminoethanol, histidinol, isoleucinol, leucinol, methioninol, 1-methyl-2-pyrrolidinemethanol, threoninol, tryptophanol, alaninol, argininol, glycinol, glutaminol, 4-amino-5-hydroxypentanamide, 4-amino-5-hydroxypentanoic acid, 3-amino-4-hydroxybutanoic acid, lysinol, 3-amino-4-hydroxybutanamide, and 4-hydroxy-prolinol.

The term "amino acid" refers to a group containing a carboxylic acid and an amine bound to the carbon atom immediately adjacent to the carboxylate group, and includes both natural and synthetic amino acids. Examples of amino acids include, but are not limited to, arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan. In some embodiments, the carboxyl is substituted with H, a salt, ester, alkyl, or aralkyl. The amino group may also be substituted with H, acyl, alkyl, alkenyl, alkynyl, carboxyl, cycloalkyl, aralkyl, or heterocyclyl.

The term "ether" refers to the —R—O—R' moiety, wherein R' and R" are independently hydrogen, alkyl, alkenyl, alkynyl, carbocyclic, heterocyclic, aryl, or aralkyl. R can additionally be a covalent bond attached to a carbon.

The term "halogen" refers to a fluorine, chlorine, bromine or iodine atom.

The term "halide" refers to a functional group containing an atom bound to a fluorine, chlorine, bromine or iodine atom. Exemplary embodiments disclosed herein may include "alkyl halide," "alkenyl halide," "alkynyl halide," "cycloalkyl halide," "heterocyclyl halide," or "heteroaryl halide" groups. In exemplary embodiments, "alkyl halide" refers to a moiety containing a carbon-halogen bond containing 1, 2, 3, 4, 5, 6, 7, 8, 9 or 10 carbon atoms (i.e., $C_{1-10}$ alkyl halide). Examples of an alkyl halide group include, but are not limited to, fluoromethyl, fluoroethyl, chloromethyl, chloroethyl, bromomethyl, bromoethyl, iodomethyl and iodoethyl groups. Unless otherwise indicated, any carbon-containing group referred to herein can contain one or more carbon-halogen bonds. By way of non-limiting example, a $C_1$ alkyl group can be, but is not limited to, methyl, fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, chlorofluoromethyl, dichlorofluoromethyl, and difluorochloromethyl.

In the compounds described herein, heteroatoms are capable of bearing multiple different valencies. By way of non-limiting example, S, Se and N can be neutral or hold a positive charge. In addition, 0 can be neutral or hold a positive or negative charge.

Exemplary embodiments of the compounds and compositions of the present disclosure comprise Formulas (I), (II), and (III), which may encompass diastereomers and enantiomers of the illustrative compounds. Enantiomers are defined as one of a pair of molecular entities which are mirror images of each other and non-superimposable. Diastereomers or diastereoisomers are defined as stereoisomers other than enantiomers. Diastereomers or diastereoisomers are stereoisomers not related as mirror images. Diastereoisomers are characterized by differences in physical properties.

An embodiment of the present disclosure may comprise a compound according to Formula (I):

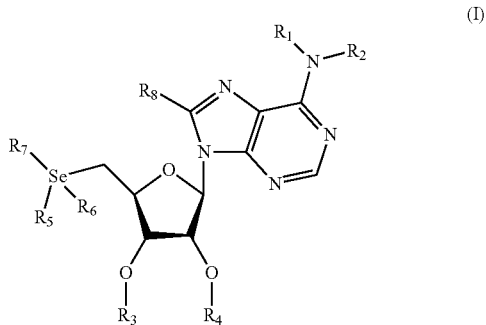

(I)

or a pharmaceutically acceptable salt, hydrate, or prodrug thereof.

$R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen.

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen.

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen.

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen.

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl.

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl.

$R_7$ is a $C_3$-$C_{16}$ alkyl, alkenyl, alkynyl, ketone, amino alcohol, amino acid, $OR^a$, Se—$R^b$, S—$R^b$, wherein $R^a$ for $OR^a$ is selected from the group consisting of H, alkyl, cycloalkyl, aryl, aralkyl, and heterocyclyl, wherein $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan; and $R_8$ is hydrogen, azido, alkyl, alkenyl, or alkynyl.

The term "Compound C" refers to 5'-Methylselenoadenosine, also known as (2R,4S,5 S)-2-(6-amino-9H-purin-9-yl)-5-((methyl selanyl)methyl)tetrahydrofuran-3,4-diol (CAS Registry Number 5135-40-0), and includes any pharmaceutically acceptable salts thereof.

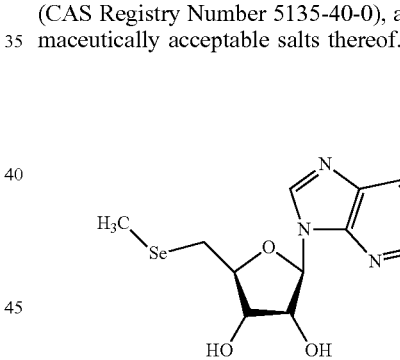

"Compound C"

Another embodiment of the present disclosure may comprise a compound according to Formula (II):

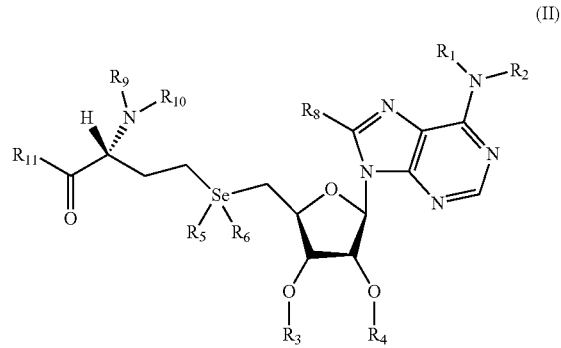

(II)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_8$ is hydrogen, azido, alkyl, alkenyl, or alkynyl;

$R_9$ is H, acyl, alkyl, alkenyl, alkynyl, aralkyl, carboxyl, cycloalkyl, C(O)$R^c$, C(O)O$R^c$, where $R^c$ is alkyl, cycloalkyl, aryl, aralkyl, or heterocyclyl; or $R_9$ together with $R_{10}$ form a heterocyclic ring having 4 to 8 ring members with at least one heteroatom selected from nitrogen;

$R_{10}$ is H, acyl, alkyl, alkenyl, alkynyl, aralkyl, carboxyl, cycloalkyl, C(O)$R^c$, C(O)O$R^c$, where $R^c$ is selected from alkyl, cycloalkyl, aryl, aralkyl, or heterocyclyl; or $R_9$ together with $R_{10}$ form a heterocyclic ring having 4 to 8 ring members with at least one heteroatom selected from nitrogen; and $R_{11}$ is OR, alkoxy, aralkoxy, or amino, where R is selected from alkyl, cycloalkyl, aryl, aralkyl, or heterocyclyl.

The term "Compound D" refers to 5'-Selenoadenosyl homocysteine; (2R)-2-amino-4-((((2S,3 S,5R)-5-(6-amino-9H-purin-9-yl)-3,4-dihydroxytetrahydrofuran-2-yl)methyl) selanyl)butanoic acid (CAS Registry Number 4053-91-2), and includes any pharmaceutically acceptable salts thereof.

"Compound D"

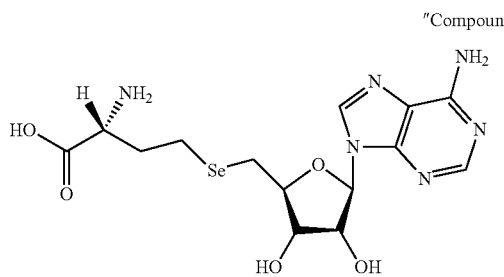

A further embodiment of the present disclosure may comprise a compound according to Formula (III):

(III)

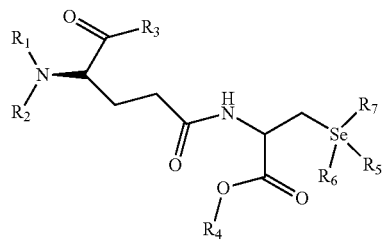

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is OH, OR, alkoxy, aralkoxy, or amino, where R is selected from alkyl, cycloalkyl, aryl, aralkyl, or heterocyclyl;

$R_4$ is alkyl, alkenyl, alkynyl, cycloalkyl, aryl, aralkyl, or heterocyclyl;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl; and $R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

The term "Compound E" refers to γ-L-glutamyl-Se-methyl-L-selenocysteine; also known as N5-(1-carboxy-2-(methylselanyl)ethyl)-L-glutamine, or any pharmaceutically acceptable salt thereof.

"Compound E"

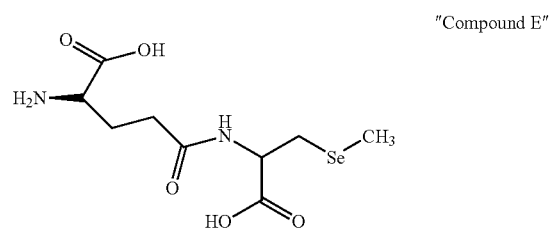

The terms "Compound CDE," "Compounds CDE, "Compound CDE combination" or "Compound CDE in combination" refers to a combination or mixture of Compound C, Compound D and Compound E, or pharmaceutically acceptable salts thereof.

The term "Compound H" refers to 5'-Methylthioadenosine; 5'-S-Methyl-5'-thioadenosine (CAS Registry No. 2457-80-9), or a pharmaceutically acceptable salt thereof.

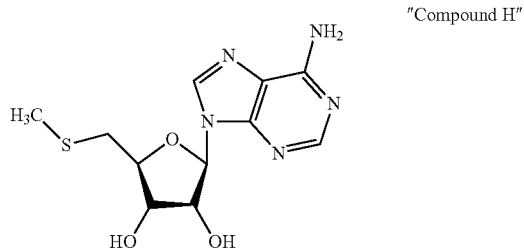

"Compound H"

The term "Compound I" refers to S-Adenosyl-L-homocysteine, also known as (S)-5'-(S)-(3-Amino-3-carboxypropyl)-5'-thioadenosine (CAS Registry No. 979-92-0), or a pharmaceutically acceptable salt thereof.

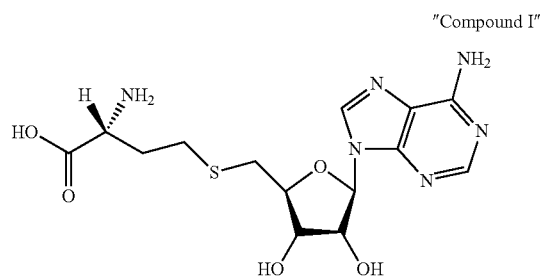

"Compound I"

The term "Compound J" refers to γ-L-glutamyl-methyl-L-cysteine, also known as Gamma-glutamyl-methyl-cysteine, or a pharmaceutically acceptable salt thereof.

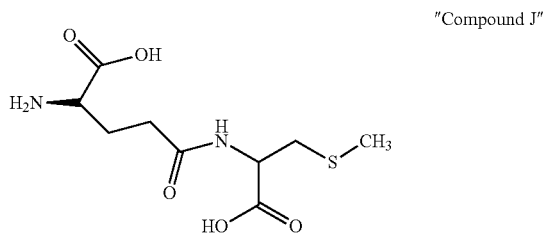

"Compound J"

The term "Compound HIJ" refers to a mixture of Compound H, Compound I and Compound J, or pharmaceutically acceptable salts thereof.

The terms "analog" and "derivative" are interchangeable, and refer to a natural or non-natural modification of at least one position of a given molecule. For example, a derivative of a given compound or molecule may be modified either by addition of a functional group or atom, removal of a functional group or atom or change of a functional group or atom to a different functional group or atom (including, but not limited to, isotopes).

The term "comprising" refers to a composition, compound, formulation, or method that is inclusive and does not exclude additional elements or method steps. The term "comprising" also refers to a composition, compound, formulation, or method embodiments of the present disclosure that is inclusive and does not exclude additional elements or method steps.

The term "consisting of" refers to a compound, composition, formulation, or method that excludes the presence of any additional component or method steps. The term "consisting of" also refers to a compound, composition, formulation, or method of the present disclosure that excludes the presence of any additional component or method steps.

The term "consisting essentially of" refers to a composition, compound, formulation or method that is inclusive of additional elements or method steps that do not materially affect the characteristic(s) of the composition, compound, formulation or method. The term "consisting essentially of" also refers to a composition, compound, formulation or method of the present disclosure that is inclusive of additional elements or method steps that do not materially affect the characteristic(s) of the composition, compound, formulation or method.

The term "compound(s)" refers to any one or more chemical entity, moiety, pharmaceutical, drug, and the like that can be used to treat, diagnose, or prevent a disease, illness, sickness, or disorder of bodily function. A compound can be determined to be therapeutic by using the screening methods of the present application.

The term "composition(s)" refers to the combination of one or more compounds with or without another agent, such as but not limited to a carrier agent. (e.g., one or more selenium containing compounds with a carrier, inert or active, making the composition especially suitable for diagnostic or therapeutic use in vitro, in vivo, or ex vivo.

The term "component" refers to a constituent part of a compound or a composition. For example, components of a composition can include a compound, a carrier, and any other agent present in the composition.

The term "effective amount" refers to the amount of a composition or compound sufficient to effect beneficial or desired results. An effective amount can be administered in one or more applications or dosages and is not intended to be limited to a particular formulation or administration route.

The term "hydrate" refers to a compound which is associated with water in the molecular form (i.e., in which the H—OH bond is not split), and may be represented, for example, by the formula $R \times H_2O$, where R is a compound disclosed herein. A given compound may form more than one hydrate including, for example, monohydrates ($R \times H_2O$), dihydrates ($R_2 \times H_2O$), trihydrates ($R_3 \times H_2O$), and the like.

The term "inhibitory" or "antagonistic" refers to the property of a compound that decreases, limits, inhibits, or blocks the action or function of another compound.

The term "isolated" refers to the separation of a material from at least one other material in a mixture or from materials that are naturally associated with the material. For example, a compound synthesized synthetically is separated from a starting material or an intermediate.

A "known therapeutic compound" refers to a therapeutic compound that has been shown (e.g., through animal trials or prior experience with administration to humans) to be effective in a treatment. In other words, a known therapeutic compound is not limited to a compound known or shown to be efficacious in the treatment of disease (e.g., neurodegenerative disease).

The term "mitochondrial potential" refers to a voltage difference across the inner mitochondrial membrane maintained by the net movement of positive charges across the membrane.

The term "modulates glucose metabolism" refers to a change in the state (e.g. activity or amount) from a known or determined state in a cell or living organism of a biochemical pathway that forms, converts or breaks down glucose or component thereof.

"Optional" or "optionally" refers to a circumstance in which the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution.

The term "organic selenium" or "selenoorganic compound" refers to any organic compound wherein selenium replaces sulfur. Thus, organic selenium can refer to any such compound biosynthesized by yeast or to free organic selenocompounds that are chemically synthesized, such as free selenomethionine.

The terms "patient" or "subject" are used interchangeably and refer to any member of Kingdom Animalia. A subject may be a mammal, such as a human, domesticated mammal (e.g., dog or cat), or a livestock mammal (e.g., cow/cattle or pig/swine).

The term "ppb" as used herein refers to parts per billion based on selenium for selenium-containing compounds or based on sulfur for sulfur-containing compounds. Examples of Selenium containing compounds are Compound C, Compound D, and Compound E. Examples of sulfur containing compounds are Compound H, Compound I, and Compound J. In order to convert ppb based on selenium to ppb of the compound containing selenium multiply the indicated ppb by the following factors: 4.35 for Compound C, 5.46 for Compound D, and 3.94 for Compound E. In order to convert ppb based on sulfur to ppb of the compound containing sulfur multiply the indicated ppb by the following factors: 9.28 for Compound H, 12.00 for Compound I, and 8.25 for Compound J.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a pharmaceutically acceptable carrier. The phrase "pharmaceutically acceptable carrier" refers to a pharmaceutically acceptable material, composition or control, such as a liquid or solid filler, diluent, excipient, solvent or encapsulating material, involved in carrying or transporting a selenium-containing compound, analog, or derivative from one organ or portion of the body to another organ or portion of the body. A carrier must be acceptable in the sense of being compatible with the other ingredients of the formulation and not injurious to the patient or subject.

Some examples of materials which may serve as pharmaceutically acceptable carriers include, but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleaste and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prodrug" refers to a pharmacologically active compound. More typically, a "prodrug" refers to an inactive compound that is converted into a pharmacologically active agent by a metabolic transformation. A prodrug of a compound or composition described herein is prepared by modifying functional groups present in the compound of any of the formula above in such a way that the modifications may be cleaved in vivo to release the parent compound. A prodrug may readily undergo in vivo chemical changes under physiological conditions (e.g., hydrolysis or enzyme catalysis) resulting in liberation of the pharmacologically active agent. Prodrugs include compounds of any of the formula described herein, wherein a hydroxy, amino, or carboxy group is bound to any group that may be cleaved in vivo to regenerate the free hydroxyl, amino or carboxy group, respectively. Examples of prodrugs include, but are not limited to, esters (e.g., acetate, formate, and benzoate derivatives) of compounds of any of the formula above or any other derivative, which upon being brought to the physiological pH or through enzyme action is converted to the active parent drug. Conventional procedures for the selection and preparation of suitable prodrug derivatives are described in the art (see, for example, Bundgaard. Design of Prodrugs. Elsevier, 1985).

The term "purified" or "substantially purified" refers to the removal of inactive or inhibitory components (e.g., contaminants) from a composition to the extent that 10% or less (e.g., 10% or less, 9% or less, 8% or less, 7% or less, 6% or less, 5% or less, 4% or less, 3% or less, 2% or less, or 1% or less) of the composition comprises inactive components, compounds, or pharmaceutically acceptable carriers.

The term "salts" can include pharmaceutically acceptable acid addition salts or addition salts of free bases. Examples of acids which may be employed to form pharmaceutically acceptable acid addition salts include, but are not limited to, salts derived from nontoxic inorganic acids such as nitric, phosphoric, sulfuric, or hydrobromic, hydroiodic, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, maleic, succinic, or citric acids. Non-limiting examples of such salts include napadisylate, besylate, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleaste, tartrate, methanesulfonate, and the like.

Also contemplated are salts of amino acids, such as, but not limited to arginate, gluconate, galacturonate, and other salts, such as, but not limited to those disclosed in Berge, et al. ("Pharmaceutical Salts", J. Pharma. Sci. 1977; 66:1-19).

The phrase "pharmaceutically acceptable salts" include, but is not limited to, salts well known to those skilled in the art. For example, mono-salts (e.g., alkali metal and ammonium salts) and poly-salts (e.g., di-salts or tri-salts) of the present invention. Pharmaceutically acceptable salts of compounds of the disclosure are prepared, for example, when an exchangeable group, such as hydrogen in the —OH, —NH—, or —P(=O)(OH)— moieties, is replaced with a pharmaceutically acceptable cation (e.g., a sodium, potassium, or ammonium ion) and can conveniently be prepared from a corresponding compound disclosed herein by, for example, reaction with a suitable base.

In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example, by reacting a sufficiently basic compound, such as an amine with a suitable acid affording a physiologically acceptable anion. Alkali metal salts (e.g., sodium, potassium or lithium) or alkaline earth metal salts (e.g., calcium) of carboxylic acids can also be made.

The terms "selenium-enriched yeast" and "selenized yeast" refer to any yeast (e.g., *Saccharomyces cerevisiae*) that is cultivated in a medium containing a selenium source, such as inorganic selenium salts. The amount of residual inorganic selenium salt in the finished product is generally quite low (e.g., less than 2%).

The term "substituted" in connection with a moiety refers to a further substituent which is attached at any acceptable location on the moiety. Unless otherwise indicated, moieties can bond through a carbon, nitrogen, oxygen, sulfur, or any other acceptable atom. Examples of substituents include, but are not limited to amines, alcohols, thiols, ethers, alkenes, alkynes, epoxides, aziridines, oxiranes, azetidines, dihydrofurans, pyrrolidines, pyrans, piperidines, aldehydes, ketones, esters, carboxylic acids, carboxylates, imines, imides, azides, azo groups, eneamines, alkyl halides, alkenyl halides, alkynyl halides, aryl halides, phosphines, phosphine oxides, phosphinites, phosphonites, phosphites, phosphonates, phosphates, sulfates, sulfoxides, sulfonyl groups, sulfoxyl groups, sulfonates, nitrates, nitrites, nitriles, nitro groups, nitroso groups, cyanates, thiocyanates, isothiocyanates, carbonates, acyl halides, peroxides, hydroperoxides, hemiacetals, hemiketals, acetals, ketals, orthoesters, orthocarbonate esters, sulfides, disulfides, sulfonic acids, sulfonic acids, thiones, thials, phosphodiesters, boronic acids, boronic esters, boronic acids and boronic esters.

The terms "treating," "treat," or "treatment" refer to a therapeutic treatment where the object is to slow down (e.g., lessen or postpone) the onset of an undesired physiological condition, to reduce symptoms of a present disorder or disease, or to obtain beneficial or desired results, such as partial or total restoration or inhibition in decline of a parameter, value, function, metric, or result that had or would become abnormal. Beneficial or desired results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease.

The term "reagent(s) capable of specifically detecting gene expression" refers to reagents capable of or sufficient to detect the expression of various genes described herein. Examples of suitable reagents include, but are not limited to, nucleic acid primers or probes capable of specifically hybridizing to mRNA or cDNA and antibodies (e.g., monoclonal or polyclonal antibodies).

The term "toxic" refers to any detrimental or harmful effects on a subject, a cell, or a tissue as compared to the same cell or tissue prior to the administration of the toxicant.

Compounds and Compositions

The present disclosure is directed to selenoorganic compounds, compositions, and methods of using the compounds and compositions. The compounds and compositions disclosed herein may replace insulin, enhance insulin activity, inhibit glucose production, or modulate glucose metabolism in various biological pathways. Compositions, compounds and methods of the present disclosure do not appear to adversely affect glucose metabolism in liver cells so they may also be used to treat or prevent Noninsulin-Dependent (Type II) Diabetes Mellitus.

One embodiment of the present disclosure is directed to a composition comprising, consisting essentially of, or consisting of a compound of Formula (I):

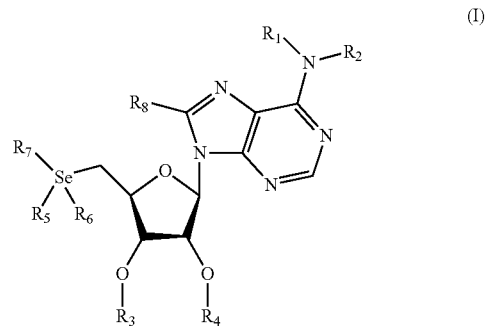

or a pharmaceutically acceptable salt, hydrate, or prodrug thereof.

$R_1$ is H, acyl, alkyl, alkenyl, alkynyl, aralkyl, carboxyl, cycloalkyl, C(O)R', or C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen.

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen.

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen.

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen.

$R_5$ is oxo, hydroxyl, alkyl, alkenyl, alkynyl, OR'', or is absent; where R'' is selected from alkyl, alkenyl, alkynyl, cycloalkyl, aryl, or aralkyl.

$R_6$ is oxo, hydroxyl, alkyl, alkenyl, alkynyl, OR'', or is absent; where R'' is selected from alkyl, alkenyl, alkynyl, cycloalkyl, aryl, or aralkyl.

$R_7$ is a $C_3$-$C_{16}$ alkyl, alkenyl, alkynyl, ketone, amino alcohol, amino acid, $OR^a$, Se—$R^b$, S—$R^b$, where $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, where $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan; and $R_8$ is hydrogen, azido, alkyl, alkenyl, or alkynyl.

An additional embodiment of the compositions described herein may comprise, consist essentially of, or consist of 5'-Methylselenoadenosine ("Compound C"), and any analogs, derivatives, and/or pharmaceutically acceptable salts thereof. Compound C is (2R,4S,5S)-2-(6-amino-9H-purin-9-yl)-5-((methylselanyl)methyl)tetrahydrofuran-3,4-diol (CAS Registry Number 5135-40-0), and includes any analogs, derivatives, and/or pharmaceutically acceptable salts thereof.

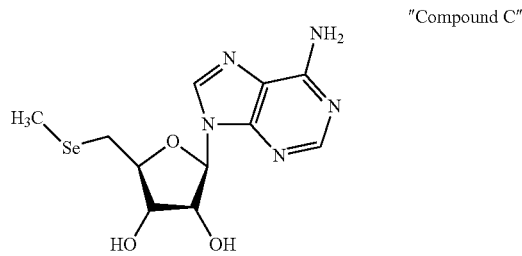

"Compound C"

A composition of the present disclosure may comprise, consist essentially of, or consist of a compound of Formula (I), Compound C, and combinations thereof. For example, one aspect of the present application provides compositions comprising a compound selected from the group consisting of 5'-Methylselenoadenosine, a compound of Formula (I), and combinations thereof. In further embodiments, one or more of these compounds can be synthetic, isolated, and/or purified.

In some embodiments, the composition comprises, consists essentially of, or consists of at least 5'-Methylselenoadenosine, and one other compound. In other embodiments, the other compound is a selenium-containing compound. In further embodiments, the composition comprises a ratio of 5'-Methylselenoadenosine to the other compound (e.g., a selenium-containing compound) of at least 1:1 to 100:1, 1:1 to 50:1, 1:1 to 10:1, 1:1 to 6:1, or 1:1 to 3:1.

In some embodiments, a composition is provided comprising, consisting essentially of, or consisting of a compound according to Formula (I), or a pharmaceutically acceptable salt, hydrate, or prodrug thereof, wherein $R_1$, $R_3$, $R_4$ and $R_8$ are each H; $R_2$ is H, acyl, alkyl, alkenyl, alkynyl, aralkyl, carboxyl, cycloalkyl, C(O)R', or C(O)OR', where R' is selected from alkyl, cycloalkyl, aryl, aralkyl, or heterocyclyl; $R_5$ and $R_6$ are each absent; and $R_7$ is a $C_3$-$C_{16}$ alkyl, alkenyl, alkynyl, ketone, amino alcohol, amino acid, $OR^a$, Se—$R^b$, S—$R^b$, where $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, where $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

In a specific embodiment, a composition is provided comprising, consisting essentially of, or consisting of at least about 0.033% (w/v) to at least about 0.1% (w/v) of a compound, or a pharmaceutically acceptable salt, hydrate, or prodrug thereof, according to Formula (I) or 5'-Methylselenoadenosine ("Compound C"). In another embodiment, the composition excludes 5'-Selenoadenosyl homocysteine and/or Gamma-L-glutamyl-Se-methyl-L-selenocysteine. In yet further embodiments, the composition excludes one or more of 5'-Methylthioadenosine, S-Adenosyl-L-homocysteine, and Gamma-glutamyl-methyl-cysteine. In some embodiments, compositions comprise a compound according to Formula (I), or 5'-Methylselenoadenosine ("Compound C"), or a pharmaceutically acceptable salt, hydrate, or prodrug thereof, with the proviso that one or more of 5'-Methylthioadenosine, Gamma-glutamyl-methyl-cysteine, or adenosyl homocysteine, homocysteine, or methionine are excluded.

In some embodiments, a composition is provided comprising a compound according to Formula (I), or a pharmaceutically acceptable salt, hydrate, or prodrug thereof, wherein $R_1$, $R_3$, $R_4$ and $R_8$ are each H; $R_2$ is H, acyl, alkyl, alkenyl, alkynyl, aralkyl, carboxyl, cycloalkyl, C(O)R', or C(O)OR', where R' is selected from alkyl, cycloalkyl, aryl, aralkyl, or heterocyclyl; $R_5$ and $R_6$ are each absent; and $R_7$ is alkyl selected from the group consisting of iso-propyl, butyl, iso-butyl, secondary-butyl, tertiary-butyl, pentyl, iso-pentyl, neo-pentyl, hexyl, iso-hexyl, 3-methylpentyl, 2,3-dimethylbutyl, neo-hexyl, heptyl, octyl, nonyl, decyl, undecyl, dodecyl, tridecyl, tetradecyl, pentadecyl, and hexadecyl, or amino acid.

In some embodiments, a composition is provided comprising, consisting essentially of, or consisting of a compound according to Formula (I), or 5'-Methylselenoadenosine ("Compound C") or a pharmaceutically acceptable salt, hydrate, or prodrug thereof, wherein $R_1$, $R_3$, $R_4$ and $R_8$ are each H; $R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; $R_5$ and $R_6$ are each absent; and $R_7$ is alkyl or amino acid; with the proviso that 5'-selenoadenosyl methionine, dehydroxy 5'-methylselenoadenosine, ethylselenoadenosine, seleno (hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, and seleno-adenosyl-Se(methyl)-selenoxide may each be excluded from the composition.

In some embodiments of the present disclosure, a composition is provided comprising, consisting essentially of, or consisting of a compound according to Formula (I), or a pharmaceutically acceptable salt, hydrate, or prodrug thereof, wherein $R_7$ is an alkyl selected from the group consisting of iso-propyl, butyl, iso-butyl, secondary-butyl, tertiary-butyl, pentyl, iso-pentyl, neo-pentyl, hexyl, iso-hexyl, 3-methylpentyl, 2,3-dimethylbutyl, neo-hexyl, heptyl, octyl, nonyl, decyl, undecyl, dodecyl, tridecyl, tetradecyl, pentadecyl, and hexadecyl, alkenyl, alkynyl, ketone, amino alcohol, an amino acid selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan, OR', Se—R', where R' is selected from an alkyl selected from the group consisting of iso-propyl, butyl, iso-butyl, secondary-butyl, tertiary-butyl, pentyl, iso-pentyl, neo-pentyl, hexyl, iso-hexyl, 3-methylpentyl, 2,3-dimethylbutyl, neo-hexyl, heptyl, octyl, nonyl, decyl, undecyl, dodecyl, tridecyl, tetradecyl, pentadecyl, and hexadecyl, cycloalkyl, aryl, aralkyl, or heterocyclyl; and $R_8$ is hydrogen, azido, alkyl, alkenyl, alkynyl.

In some embodiments, compositions of the present disclosure comprise, consist of, or consist essentially of a compound according to Formula (I), 5'-Methylselenoadenosine ("Compound C"), or a pharmaceutically acceptable salt, hydrate, or prodrug thereof, with the proviso that 5'-selenoadenosyl methionine, dehydroxy 5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, and seleno-adenosyl-Se(methyl)-selenoxide may each be excluded from the composition.

In other embodiments, a composition is provided comprising, consisting essentially of, or consisting of one or more compounds according to one or more of Formula (I) or 5'-Methylselenoadenosine ("Compound C"), wherein each of the following compounds is excluded from the composition in order to minimize selenium toxicity, remove inactive or inhibitory compounds, and/or maximize the therapeutic index of the composition, wherein the excluded compounds are γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, dehydroxy 5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, and seleno-adenosyl-Se(methyl)-selenoxide.

Another embodiment of the composition of the present disclosure comprises, consists essentially of, or consists of a compound according to Formula (II):

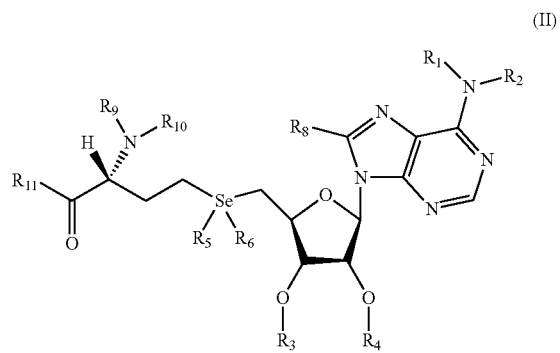

(II)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_8$ is hydrogen, azido, alkyl, alkenyl, or alkynyl;

$R_9$ is H, acyl, alkyl, alkenyl, alkynyl, aralkyl, carboxyl, cycloalkyl, C(O)R^c, or C(O)OR^c, where R^c is alkyl, cycloalkyl, aryl, aralkyl, or heterocyclyl; or $R_9$ together with $R_{10}$ form a heterocyclic ring having 4 to 8 ring members with at least one heteroatom selected from nitrogen;

$R_{10}$ is H, acyl, alkyl, alkenyl, alkynyl, aralkyl, carboxyl, cycloalkyl, C(O)R^c, or C(O)OR^c, where R^c is selected from alkyl, cycloalkyl, aryl, aralkyl, or heterocyclyl; or $R_9$ together with $R_{10}$ form a heterocyclic ring having 4 to 8 ring members with at least one heteroatom selected from nitrogen; and $R_{11}$ is OR, alkoxy, aralkoxy, or amino, where R is selected from alkyl, cycloalkyl, aryl, aralkyl, or heterocyclyl.

An additional embodiment of the compositions described herein comprises, consists essentially of, or consists of 5'-Selenoadenosyl homocysteine ("Compound D"), and includes any analogs, derivatives, and/or pharmaceutically acceptable salts thereof. Compound D is (2R)-2-amino-4-((((2S,3S,5R)-5-(6-amino-9H-purin-9-yl)-3,4-dihydroxytetrahydrofuran-2-yl)methyl) selanyl)butanoic acid (CAS Registry Number 4053-91-2), and includes any analogs, derivatives, and/or pharmaceutically acceptable salts thereof.

"Compound D"

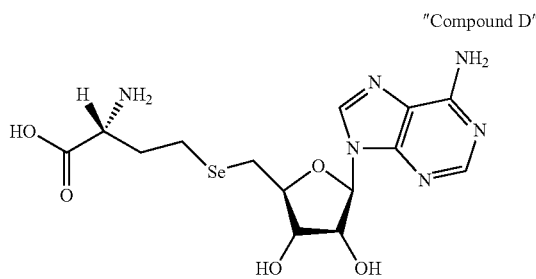

A composition of the present disclosure may comprise, consist essentially of, or consist of a compound of Formula (II), Compound D, and combinations thereof. For example, one aspect of the present application provides compositions comprising a compound selected from the group consisting of 5'-selenoadenosyl homocysteine, a compound of Formula (II), and combinations thereof. In further embodiments, one or more of these compounds can be synthetic, isolated, and/or purified.

In some embodiments of Formula (II), a composition comprises, consists essentially of, or consists of at least 5'-selenoadenosyl homocysteine ("Compound "D") and one other compound. In some embodiments, the composition comprises a ratio of 5'-selenoadenosyl homocysteine to one other selenium containing compound of at least 1:1 to 100:1, 1:1 to 50:1, 1:1 to 10:1, 1:1 to 6:1, or 1:1 to 3:1. In embodiments, the other compound is 5'-methylselenoadenosine. In embodiments, the other compound is γ-L-glutamyl-Se-methyl-L-selenocysteine.

In some embodiments, a composition is provided comprising, consisting essentially of, or consisting of a compound according to Formula (II), or a pharmaceutically acceptable salt, hydrate, or prodrug thereof, wherein $R_1$, $R_3$, $R_4$, $R_8$ and $R_9$ are each H; $R_2$ is H, acyl, alkyl, carboxyl, C(O)R', or C(O)OR', where R' is selected from alkyl, cycloalkyl, aryl, aralkyl, or heterocyclyl; $R_5$ and $R_6$ are absent; $R_{10}$ is H, acyl, alkyl, alkenyl, alkynyl, aralkyl, carboxyl, cycloalkyl, C(O)R$^c$, or C(O)OR$^c$, where R$^c$ is selected from alkyl, cycloalkyl, aryl, aralkyl, or heterocyclyl; and $R_{11}$ is OR, alkoxy, aralkoxy, or amino, where R is selected from alkyl, cycloalkyl, aryl, aralkyl, heterocyclyl, or a pharmaceutically acceptable salt, or inner salt.

In some embodiments, a composition is provided comprising, consisting essentially of, or consisting of a compound according to Formula (II), or a pharmaceutically acceptable salt, hydrate, or prodrug thereof, wherein $R_1$, $R_2$, $R_3$, $R_4$, $R_5$, $R_6$, $R_7$, $R_8$, $R_9$, $R_{10}$ are as defined above and wherein $R_{11}$ is OR, where R is selected from methyl, ethyl, propyl, isopropyl, butyl, sec-butyl, or tert-butyl.

In a specific aspect, a composition is provided comprising, consisting essentially of, or consisting of a compound according to Formula (II), or a pharmaceutically acceptable salt, hydrate, or prodrug thereof, 5'-selenoadenosyl homocysteine ("Compound "D"), or a pharmaceutically acceptable salt, hydrate, or prodrug thereof.

In some embodiments, compositions comprise, consist essentially of, or consist of a compound according to Formula (II), selenoadenosyl homocysteine, or a pharmaceutically acceptable salt, hydrate, or prodrug thereof; with the proviso that one or more of adenosyl homocysteine, 5'-selenoadenosyl methionine, allylselenoadenosyl homocysteine, and seleno-hydroxy adenosyl homocysteine may each be excluded from the composition. In embodiments, a composition excludes one or more compounds one or more of 5'-Methylthioadenosine, Gamma-glutamyl-methyl-cysteine, or adenosyl homocysteine, homocysteine or methionine.

A further embodiment of the composition of the present disclosure may comprise, consist essentially of, or consist of a compound according to Formula (III):

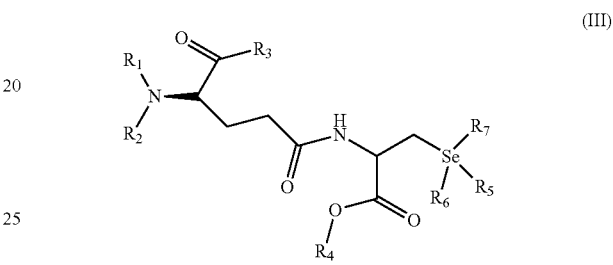

(III)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is OH, OR, alkoxy, aralkoxy, or amino, where R is selected from alkyl, cycloalkyl, aryl, aralkyl, or heterocyclyl;

$R_4$ is alkyl, alkenyl, alkynyl, cycloalkyl, aryl, aralkyl, or heterocyclyl;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl; and $R_7$ is a $C_3$-$C_{16}$ alkyl, alkenyl, alkynyl, ketone, amino alcohol, amino acid, OR$^a$, Se—R$^b$, S—R$^b$, wherein R$^a$ for OR$^a$ is selected from the group consisting of H, alkyl, cycloalkyl, aryl, aralkyl, and heterocyclyl, where R$^b$ for Se—R$^b$ is selected from the group consisting of H, $C_3$-$C_{16}$ alkyl, cycloalkyl, aryl, aralkyl, and heterocyclyl, wherein R$^b$ for S—R$^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

An additional embodiment of the compositions described herein may comprise, consist essentially of, or consist of Gamma (γ)-L-glutamyl-Se-methyl-L-selenocysteine ("Compound E"), and includes any analogs, derivatives, and/or pharmaceutically acceptable salts thereof. Compound E is N5-(1-carboxy-2-(methylselanyl)ethyl)-L-glutamine, and includes any analogs, derivatives, and/or pharmaceutically acceptable salts thereof.

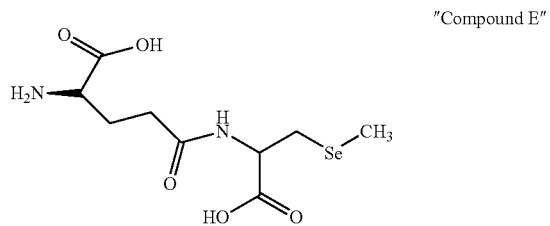

"Compound E"

A composition of the present disclosure may comprise, consist essentially of, or consist of a compound of Formula (III), Compound E, and combinations thereof. For example, one aspect of the present application provides compositions comprising a compound selected from the group consisting of Gamma (γ)-L-glutamyl-Se-methyl-L-selenocysteine, a compound of Formula (III), and combinations thereof. In further embodiments, one or more of these compounds can be synthetic, isolated, and/or purified.

One aspect of the present application provides compositions comprising a compound selected from the group consisting of Gamma-L-glutamyl-Se-methyl-L-selenocysteine, a compound of Formula (III) and combinations thereof. In further embodiments, one or more of these compounds can be isolated and/or purified. In embodiments, a composition comprises at least 0.033% (w/v) of one of the compounds.

In embodiments, a composition comprises at least Gamma-L-glutamyl-Se-methyl-L-selenocysteine and one other compound. In some embodiments, the composition comprises a ratio of Gamma-L-glutamyl-Se-methyl-L-selenocysteine to one other selenium containing compound of at least 1:1 to 100:1, 1:1 to 50:1, 1:1 to 10:1, 1:1 to 6:1, or 1:1 to 3:1. In embodiments, the other compound is 5'-methyl selenoadenosine. In embodiments, the other compound is Gamma (γ)-L-glutamyl-methyl-L-cysteine.

In a specific aspect, a composition is provided comprising a compound according to Formula (III), or a pharmaceutically acceptable salt, hydrate, or prodrug thereof, Gamma-L-glutamyl-Se-methyl-L-selenocysteine ("Compound E"), or a pharmaceutically acceptable salt, hydrate, or prodrug thereof in a ratio to one other selenium containing compound in the composition of at least 1:1.

In some embodiments, a composition comprises a compound according to Formula (III), Gamma-L-glutamyl-Se-methyl-L-selenocysteine, or a pharmaceutically acceptable salt, hydrate, or prodrug thereof, with the proviso that one or more of γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, γ-glutamoyl selenocysteine-γ-glutamoyl cysteine, γ-glutamoylcysteine-2,3-DHP-selenocysteine, di-γ-glutamoylselenocysteine and selenoglutathione-γ-glutamoylcysteine may each be excluded from the composition.

In some embodiments, a composition comprises a compound according to Formula (III), Gamma-L-glutamyl-Se-methyl-L-selenocysteine, or a pharmaceutically acceptable salt, hydrate, or prodrug thereof, with the proviso that one or more of 5'-Methylthioadenosine, Gamma-glutamyl-methyl-cysteine, or adenosyl homocysteine, homocysteine or methionine are excluded.

Another aspect of the present application provides analogs or derivatives of the biologically active selenium-containing compounds described herein, e.g., Formulas (I), (II), and (III). Analogs and/or derivatives of the selenium-containing compounds can be prepared synthetically. For example, one embodiment of Formulas (I), (II), and (III) comprises any analog, derivative or pharmaceutically acceptable salts thereof. Another embodiment of the present composition comprises a compound of Formulas (I), (II), and (III), and combinations thereof.

Additional embodiments of the composition of the present disclosure may comprise, consist essentially of, or consist of mixtures of the compounds described herein. For example, one embodiment of the present composition is "Compounds CDE." Compounds CDE comprises a mixture of Compound C, Compound D and Compound E, and any analogs, derivatives, and/or pharmaceutically acceptable salts thereof. Compounds CE comprises a mixture of Compound C and Compound E, and any analogs, derivatives, and/or pharmaceutically acceptable salts thereof. Compounds DE comprises a mixture of Compound D and Compound E, and any analogs, derivatives, and/or pharmaceutically acceptable salts thereof.

In some embodiments, a composition of the present application comprises, consists essentially of, or consists of at least about 0.033% (w/v) to at least about 0.1% (w/v) of one of the compounds: Compound C, Compound D, Compound E, Compounds CDE, Formula (I), Formula (II), Formula (III), or mixtures thereof. For example, a composition may comprise at least 0.033% (w/v), at least 0.05% (w/v), at least 0.1% (w/v), at least about 0.033% (w/v), at least about 0.05% (w/v), at least about 0.1% (w/v), at least about 0.033% (w/v) to at least about 0.1% (w/v) or at least about 0.05% (w/v) to at least about 0.1% (w/v) of Compound C, Compound D, Compound E, a compound according to Formula (I), Formula (II), Formula (III), Compounds CDE, or mixtures thereof.

For example, in some embodiments, the composition comprises at least about 0.033% (w/v) to at least about 0.035% (w/v), at least about 0.033% to at least about 0.040% (w/v), at least about 0.033% to at least about 0.045% (w/v), at least about 0.033% to at least about 0.050% (w/v), at least about 0.033% to at least about 0.055% (w/v), at least about 0.033% to at least about 0.060% (w/v), at least about 0.033% to at least about 0.065% (w/v), at least about 0.033% to at least about 0.070% (w/v), at least about 0.033% to at least about 0.075% (w/v), at least about 0.033% to at least about 0.080% (w/v), at least about 0.033% to at least about 0.085% (w/v), at least about 0.033% to at least about 0.090% (w/v), at least about 0.033% to at least about 0.095% (w/v), or at least about 0.033% to at least about 0.1% (w/v) of one compound of Formula (I), Formula (II), Formula (III), Compound C, Compound D, Compound E, Compounds CDE, or mixtures thereof, and all percent range values in between.

For example, in some embodiments, the composition comprises at least about 0.05% to at least about 0.060% (w/v), at least about 0.05% to at least about 0.065% (w/v), at least about 0.05% to at least about 0.070% (w/v), at least about 0.05% to at least about 0.075% (w/v), at least about 0.05% to at least about 0.080% (w/v), at least about 0.05% to at least about 0.085% (w/v), at least about 0.05% to at least about 0.090% (w/v), at least about 0.05% to at least about 0.095% (w/v), or at least about 0.05% to at least about 0.1% (w/v) of one compound of Formula (I), Formula (II), Formula (III), Compound C, Compound D, Compound E, Compounds CDE, or mixtures thereof, and all percent range values in between.

In other embodiments, the composition comprises about 0.033% (w/v) to about 99.9% (w/v), about 0.033% to about 90% (w/v), about 0.033% to about 80% (w/v), about 0.033% to about 70% (w/v), about 0.033% to about 60% (w/v), about 0.033% to about 50% (w/v), about 0.033% to about 40% (w/v), about 0.033% to about 30% (w/v), about 0.033% to about 20% (w/v), about 0.033% to about 10% (w/v), about 0.033% to about 5% (w/v), or about 0.033% to about 1% (w/v) of one compound of Formula (I), Formula (II), Formula (III), Compound C, Compound D, Compound E, Compounds CDE, or mixtures thereof, and all percent range values in between.

In other embodiments, the composition comprises about 0.05% (w/v) to about 99.9% (w/v), about 0.05% to about 90% (w/v), about 0.05% to about 80% (w/v), about 0.05% to about 70% (w/v), about 0.05% to about 60% (w/v), about 0.05% to about 50% (w/v), about 0.05% to about 40% (w/v), about 0.05% to about 30% (w/v), about 0.05% to about 20% (w/v), about 0.05% to about 10% (w/v), about 0.05% to about 5% (w/v), or about 0.05% to about 1% (w/v) of one compound of Formula (I), Formula (II), Formula (III), Compound C, Compound D, Compound E, Compounds CDE, or mixtures thereof, and all percent range values in between.

In further embodiments, the composition comprises about 0.1% (w/v) to about 99.9% (w/v), about 0.1% to about 90% (w/v), about 0.1% to about 80% (w/v), about 0.1% to about 70% (w/v), about 0.1% to about 60% (w/v), about 0.1% to about 50% (w/v), about 0.1% to about 40% (w/v), about 0.1% to about 30% (w/v), about 0.1% to about 20% (w/v), about 0.1% to about 10% (w/v), about 0.1% to about 5% (w/v), or about 0.1% to about 1% (w/v) of one compound of Formula (I), Formula (II), Formula (III), Compound C, Compound D, Compound E, Compounds CDE, or mixtures thereof, and all percent range values in between.

In other embodiments, a composition comprises at least about 0.033% (w/v) to at least about 0.1% (w/v) or at least about 0.05% (w/v) to at least about 0.1% (w/v) of a compound of Formula (I), Formula (II), Formula (III), Compound C, Compound D, Compound E, Compounds CDE, or a mixture thereof.

In embodiments, a composition comprises at least 5'-Methylselenoadenosine and one other compound. In some embodiments, the composition comprises a ratio of 5'-Methylselenoadenosine to one other selenium containing compound of at least 1:1 to 100:1, 1:1 to 50:1, 1:1 to 10:1, 1:1 to 6:1, or 1:1 to 3:1. In embodiments, the other compound is 5'-selenoadenosyl homocysteine. In other embodiments, the other compound is L-glutamyl-Se-methyl-L-selenocysteine.

In other embodiments, compositions may exclude one or more of 5'-Methylthioadenosine ("Compound H"), S-Adenosyl-L-homocysteine ("Compound I"), Gamma-glutamyl-methyl-cysteine ("Compound J"), Gamma-L-glutamyl-Se-methyl-L-selenocysteine, Se-adenosylhomocysteine, or glutamyl selenocysteine, because one or more of these compounds may be unnecessary to the composition or inhibitory to other compounds in the composition.

One aspect of the present application provides compositions comprising at least two compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III) and combinations thereof. In further embodiments, one or more of these compounds can be synthetic, isolated and/or purified.

One aspect of the present application is directed to 5'-Methylselenoadenosine ("Compound C"), Se-Adenosyl-L-homocysteine ("Compound D"), L-glutamyl-Se-methyl-L-selenocysteine ("Compound E") and analogs thereof. Some embodiments include a composition comprising a compound of Formula (I), Formula (II) and/or Formula (III) and mixtures thereof, and a carrier.

In other embodiments, the composition comprises at least three different compounds selected from the group consisting of: 5'-Methylselenoadenosine, Se-Adenosyl-L-homocysteine, Gamma-glutamyl-methylseleno-cysteine, a compound of Formula (I), a compound of Formula (II), and a compound of Formula (III) and mixtures thereof. In yet further embodiments, the composition comprises at least about 0.033% (w/v) of at least one of these compounds. In other embodiments, the composition comprises at least about 0.05% (w/v) for each of two of these compounds. In yet another embodiment, the composition comprises at least about 0.033% (w/v) for each of three of these compounds.

In further embodiments, one or more of these compounds of Formula (I), Formula (II) and Formula (III) can be synthetic, isolated and/or purified. In embodiments, compositions comprising compounds of Formula (I), Formula (II) and Formula (III) further comprise a carrier such as water, physiological saline, physiological buffer including surfactants and stabilizing amino acids.

In some embodiments, a composition is provided comprising one or more compounds according to one or more of Formula (I), Formula (II) Formula (III), Compound C, Compound D, Compound E, Compounds CDE, or mixtures thereof, wherein one or more of each of the following compounds is excluded from the composition in order to minimize selenium toxicity, remove inactive or inhibitory compounds, and/or maximize the therapeutic index of the composition, wherein the excluded compounds are γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, dehydroxy 5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selenoxide and seleno-adenosyl-Se(methyl)-selenoxide.

In some embodiments, a composition comprises at least two different compounds selected from the group consisting of: 5'-Methylselenoadenosine, Se-Adenosyl-L-homocysteine, Gamma-glutamyl-methylseleno-cysteine, a compound of Formula (I), a compound of Formula (II) and a compound of Formula (III) and mixtures thereof; and a carrier. In other embodiments, a composition comprises at least two different compounds selected from the group consisting of: 5'-Methylselenoadenosine, Se-Adenosyl-L-homocysteine, Gamma-glutamyl-methylseleno-cysteine; and a carrier. In embodiments, the composition comprises 5'-Methylselenoadenosine and Gamma-glutamyl-methylseleno-cysteine. In embodiments, each of the two compounds is present in the composition at least about 0.033% (w/v).

In other embodiments, a composition comprises at least three different compounds selected from the group consisting of: 5'-Methylselenoadenosine, Se-Adenosyl-L-homocysteine, Gamma-glutamyl-methylseleno-cysteine, a compound of Formula (I), a compound of Formula (II) and a compound of Formula (III) and mixtures thereof; and a carrier. In other embodiments, a composition comprises at least three different compounds selected from the group consisting of: 5'-Methylselenoadenosine, Se-Adenosyl-L-homocysteine, Gamma-glutamyl-methylseleno-cysteine; and a carrier. In embodiments, each of the three compounds is present in the composition at least about 0.033% (w/v).

In some embodiments, any of the compounds of the present application described herein can be modified with a prodrug to prolong half-life. Prodrugs may also be helpful to protect the compound against oxidation, to target the compound to a tissue, or to allow the compound to pass the blood brain barrier.

In some embodiments, a prodrug comprises a selenoglycoside. Glycosides include monosaccharides, disaccharides, and oligosaccharides. Saccharides can include ribose, glucose, galactose, or mannose. For example, a galactose conjugated to a selenium moiety could target the compound to the liver.

In other embodiments, a prodrug comprises a selenazolidine. These compounds provide for slow release of the compound.

In yet a further embodiment, a prodrug comprises conjugation of a selenoorganic compound to a vitamin, such as Vitamin C or Vitamin E These prodrug conjugates have improved protective effects.

In yet other embodiments, a prodrug may be a cytochrome P450 activated prodrug, such as cyclic phosphates or phosphonates. Other embodiments of cytochrome P450 activated prodrugs improve bioavailability. In particular, nucleosides have been modified with these molecules and provide for targeting of molecules to the liver. Exemplary prodrugs include HepDirect prodrugs. Other embodiments of cytochrome P450 activated prodrug improve bioavailability and are described in Huttunen et al, Current Medicinal Chemistry 2008 15:2346.

In embodiments, any of the compounds of Formula (I), Formula (II), Formula (III), Compound C, Compound D, Compound E, or Compounds CDE, can be modified to reduce oxidation of selenium. In embodiments, compounds can form a dimer through linkage between selenium atoms.

In embodiments, any of the of the compounds of Formula (I), Formula (II), Formula (III), Compound C, Compound D, Compound E, or Compounds CDE can be modified by linkage to a tissue targeting agent or other agent for increasing half-life of the compound. Tissue targeting agents may include any agent known in the art, including, but not limited to, antibodies specific for binding to a tissue specific antigen, a transferrin receptor, or a prodrug as described herein.

In some embodiments, a composition of the invention is formulated to cross the blood brain barrier. Compositions of the invention can be combined with an implant material suitable for delivery to the brain, such as a polymeric biodegradable implant or carrier. Such polymeric carriers include, but are not limited to, polyethylene glycol, poly lactides, polyglycolides, polyorthoesters, polyvinyl pyrrolidone, and poly vinyl alcohols, and ethylene-co-vinyl acetate.

In other embodiments, the compounds can be linked to or combined with a nanoparticle carrier to deliver compositions to the brain and to provide for other tissue targeting. Other nanoparticles include phospholipids, chitosan, lactic acid, and dextran.

Microspheres and liposomes are additional carriers that may be used in the present disclosure. For example, microspheres and liposomes may include, but are not limited to, poly(lactic-co-glycolic) acid or PLGA carriers. In other embodiments, carrier delivery of compositions to the brain or other body tissues can be targeted by using liposomes or microspheres comprising an antibody, a transferrin receptor, or a prodrug as a targeting agent. Tissue targeting may also involve receptor mediated transport, such as with the insulin receptor or the transferrin receptor. These receptors can be integrated into liposomes or microspheres that also include the compositions as described herein.

Lipid prodrugs are also suitable for use with the compounds of the invention. By non-limiting example, certain lipid prodrugs are described in Hostetler et al., (1997 Biochem. Pharm. 53:1815-1822) and Hostetler et al., 1996 Antiviral Research 31:59-67), both of which are incorporated in their entirety herein by reference. Additional examples of suitable prodrug technology is described in WO 90/00555; WO 96/39831; WO 03/095665A2; U.S. Pat. Nos. 5,411,947; 5,463,092; 6,312,662; 6,716,825; and U.S. Published Patent Application Nos. 2003/0229225 and 2003/0225277 each of which is incorporated in their entirety herein by reference. Such prodrugs may also possess the ability to target the drug compound to a particular tissue within the patient, e.g., liver, as described by Erion et al., (2004 J. Am. Chem. Soc. 126:5154-5163; Erion et al., Am. Soc. Pharm. & Exper. Ther. DOI:10.1124/jept.104.75903 (2004); WO 01/18013 A1; U.S. Pat. No. 6,752,981), each of which is incorporated in their entirety herein by reference.

Such prodrugs may also possess the ability to target the drug compound to a particular tissue within the patient, e.g., liver, as described by Erion et al., (2004 J. Am. Chem. Soc. 126:5154-5163; Erion et al., Am. Soc. Pharm. & Exper. Ther. DOI:10.1124/jept.104.75903 (2004); WO 01/18013 A1; U.S. Pat. No. 6,752,981), each of which is incorporated in their entirety herein by reference. By way of non-limiting example, other prodrugs suitable for use with the compounds of the invention are described in WO 03/090690; U.S. Pat. No. 6,903,081; U.S. Patent Application No. 2005/0171060A1; U.S. Patent Application No. 2002/0004594A1; and by Harris et al., (2002 Antiviral Chem & Chemo. 12: 293-300; Knaggs et al., 2000 Bioorganic & Med. Chem. Letters 10: 2075-2078) each of which is incorporated in their entirety herein by reference.

In some embodiments, a composition is provided comprising one or more compounds each according to Formula (I). In some aspects, the composition comprises 5'-methylselenoadenosine, or a pharmaceutically acceptable salt, hydrate, or prodrug thereof; and 5'-selenoadenosyl homocysteine, or a pharmaceutically acceptable salt, hydrate, or prodrug thereof.

In some embodiments, a composition is provided comprising one or more compounds each according to Formula (I) and Formula (III). In some aspects, the composition comprises 5'-methylselenoadenosine, or a pharmaceutically acceptable salt, hydrate, or prodrug thereof; 5'-selenoadenosyl homocysteine, or a pharmaceutically acceptable salt, hydrate, or prodrug thereof; and gamma-L-glutamyl-Se-methyl-L-selenocysteine, or a pharmaceutically acceptable salt, hydrate, or prodrug thereof.

In some embodiments, the composition comprises 5'-methylselenoadenosine, or a pharmaceutically acceptable salt, hydrate, or prodrug thereof; and gamma-L-glutamyl- Se-methyl-L-selenocysteine, or a pharmaceutically acceptable salt, hydrate, or prodrug thereof.

In some embodiments, a composition is provided comprising one or more compounds each according to Formula (I) and Formula (II). In some embodiments, a composition is provided comprising one or more compounds each according to Formula (II) and (III).

In embodiments, any of the compositions described herein can further comprise a different therapeutic agent for modulating glucose metabolism or treating diabetes.

In some embodiments, the different therapeutic agent is insulin or an analog thereof. Insulin analogs include fast acting insulin analogs and long acting insulin analogs. Insulin analogs can have one or more amino acid changes. Fast acting insulin analogs include Aspart, Glulisine and LisPro. Long acting insulins include NPH insulin, Insulin detemir, Degludec insulin or Insulin glargine.

In an embodiment, the composition further comprises a different therapeutic agent for modulating glucose metabolism or treating diabetes. In some embodiments, the different therapeutic agent is insulin or an analog thereof. In some embodiments, the different therapeutic agent is an insulin sensitizer, an insulin secretagogue or an incretin mimetic. Other exemplary therapeutic agents effective in the present composition may be used to treat diabetes include metformins, sulfonylureas, meglitinides, D-phenylalanine derivatives, thiazolidinediones, DPP-4 inhibitors, alpha glucosidase inhibitors, bile acid sequestrants and combinations thereof.

According to another aspect of the present invention, a pharmaceutical composition comprises a therapeutically-effective amount of one or more compounds of the present invention or a pharmaceutically acceptable salt, ester or prodrug thereof, together with a pharmaceutically acceptable diluent or carrier. Exemplary diluents and carriers of the present invention are described in detail in the Definitions section of this application. For example, in some embodiments, carriers can include water, physiological saline, and aqueous buffered solutions containing surfactants or stabilizing amino acids, such as histidine or glycine. In one embodiment of the present application, the pharmaceutically acceptable carrier is pharmaceutically inert.

In some embodiments of the present application, compositions and/or formulations comprising selenium can be administered to a subject alone, or in combination with other forms of selenium, drugs, small molecules, or in pharmaceutical compositions where it is mixed with excipient(s) or other pharmaceutically acceptable carriers. In other embodiments, compositions of the present application can be formulated using pharmaceutically acceptable carriers well known in the art in dosages suitable for oral administration. The carriers may enable the pharmaceutical compositions to be formulated as tablets, pills, capsules, liquids, gels, syrups, slurries, suspensions and the like, or for oral or nasal ingestion by a patient to be treated. In addition, compositions comprising one or more compounds including, but not limited to, 5'-Methylselenoadenosine, a compound of Formula (I), and combinations thereof can be administered to a subject (e.g., a patient) intravenously in a pharmaceutically acceptable carrier, such as physiological saline.

The compositions may be formulated for any route of administration, in particular for oral, rectal, transdermal, subcutaneous, intravenous, intramuscular or intranasal administration. The compositions may be formulated in any conventional form, for example, as tablets, capsules, caplets, solutions, suspensions, dispersions, syrups, sprays, gels, suppositories, patches and emulsions.

As is well known in the medical arts, dosages for any one subject may depend upon many factors, including the patient's size, body surface area, age, the particular compound to be administered, sex, time and route of administration, general health and interaction with other drugs being concurrently administered. Depending on the target sought to be altered by treatment, pharmaceutical compositions may be formulated and administered systemically or locally.

Techniques known in the art for formulation and administration of therapeutic compounds are sufficient to administer the compounds and compositions of the present invention and may be found in the latest edition of "Remington's Pharmaceutical Sciences" (Mack Publishing Co, Easton Pa.). The compositions of the present disclosure may be formulated for any route of administration, in particular for oral, rectal, transdermal, subcutaneous, intravenous, intramuscular or intranasal administration. Suitable routes of administration may, for example, include oral or transmucosal administration; as well as parenteral delivery, including intramuscular, subcutaneous, intramedullary, intrathecal, intraventricular, intravenous, intraperitoneal, or intranasal administration.

For injection, a composition of the present application (e.g., a selenium-containing composition) may be formulated in aqueous solutions, such as in physiologically compatible buffers such as Hanks' solution, Ringer's solution, or physiologically buffered saline. For tissue, organ, or cellular administration, penetrants appropriate to the particular barrier to be permeated are used in the formulation. Such penetrants are generally known in the art.

Pharmaceutical compositions suitable for use in the present application include compositions wherein the active ingredients (e.g., 5'-Methylselenoadenosine, Se-Adenosyl-L-homocysteine, Gamma-glutamyl-methylseleno-cysteine, a compound of Formula (I), a compound of Formula (II), a compound of Formula (III) and mixtures thereof) are contained in an effective amount to achieve the intended purpose. For example, in a preferred embodiment, an effective amount of a pharmaceutical composition comprises an amount of a compound selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III) and mixtures thereof. Determination of effective amounts is well within the capability of those skilled in the art, especially in light of the disclosure provided herein.

Some selenium-containing compounds have been prepared synthetically, purified and screened in a bioactivity assay. Not all components and compounds found in selenized yeast or a water extract thereof have biological activity when obtained from such yeast and in fact, may be toxic to cells.

The compositions of the present disclosure may be formulated for any route of administration, in particular for oral, rectal, transdermal, subcutaneous, intravenous, intramuscular or intranasal administration. Suitable routes of administration may, for example, include oral or transmucosal administration; as well as parenteral delivery, including intramuscular, subcutaneous, intramedullary, intrathecal, intraventricular, intravenous, intraperitoneal, or intranasal administration.

For injection, a composition of the present application (e.g., a selenium-containing composition) may be formulated in aqueous solutions, such as in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In embodiments, compositions containing or synthetically formulated compounds may comprise an equal amount of each selenium-containing component, for example, a ratio of at least 1:1:1 of Gamma-glutamyl-methylseleno-cysteine to 5'-Methylselenoadenosine to Se-Adenosyl-L-homocysteine. In other embodiments, a composition may comprise at least two components in ratios of 1:1 to 100:1, 1:1 to 50:1, 1:1 to 10:1, 1:1 to 6:1, or 1:1 to 3:1.

Compositions comprising one or more compounds including 5'-Methylselenoadenosine, Se-Adenosyl-L-homocysteine, Gamma-glutamyl-methylseleno-cysteine, a compound of Formula (I), a compound of Formula (II), a compound of Formula (III) and combinations thereof can be administered to a subject (e.g., a patient) intravenously in a pharmaceutically acceptable carrier such as physiological saline. Standard methods for intracellular delivery of compounds can be used (e.g., delivery via liposome). Such methods are well known to those of ordinary skill in the art.

Compositions comprising selenium are useful for intravenous administration as well as parenteral administration, such as intravenous, subcutaneous, intramuscular and intraperitoneal. For injection, a composition comprising selenium (e.g., a pharmaceutical composition) of the present application may be formulated in aqueous solutions, preferably in physiologically compatible buffers such as Hanks' solution, Ringer's solution or physiologically buffered saline. For tissue or cellular administration, penetrants appropriate to the particular barrier to be permeated are used in the formulation. Such penetrants are generally known in the art.

In some embodiments, pharmaceutical formulations can contain a disintegrant, gelatinized starch and a coating. In embodiments, disintegrants include crosslinked polyvinyl pyrrolidone, gums, starches including gelatinized starch and cellulose products. In embodiments, coatings include polyvinyl alcohol, cellulose derivatives and methacryllic acid derivatives.

In some embodiments of the present application, compositions and/or formulations comprising selenium can be administered to a subject alone, or in combination with other forms of selenium, drugs, small molecules, or in pharmaceutical compositions where it is mixed with excipient(s) or other pharmaceutically acceptable carriers. In embodiments, the compositions may include one or more amino acids or seleno amino acids, such as methionine, cysteine or selenocysteine in order to minimize toxicity. In one embodiment of the present application, the pharmaceutically acceptable carrier is pharmaceutically inert. In another embodiment of the present application, compositions comprising selenium may be administered alone to individuals subject to, at risk of, or suffering from a disease or condition associated with glucose metabolism.

The compositions may also be formulated in any conventional form, for example, as tablets, capsules, caplets, solutions, suspensions, dispersions, syrups, sprays, gels, suppositories, patches and emulsions. Compositions of the present application, particularly compositions comprising 5'-Methylselenoadenosine, a compound of Formula (I), and combinations thereof, may also be added to nutritional drinks or food products (e.g., ENSURE, POWERBAR, or the like), a multi-vitamin, nutritional products, etc. to aid daily consumption.

Methods of Using Compounds and Compositions

Compounds and compositions of the present disclosure exhibit tissue specificity regarding gene expression of genes relating to biological processes and transcriptional activation/inactivation. For example, the present application relates to methods of using the compounds and compositions described herein to replace insulin, enhance insulin activity, enhance glucose sensitivity, inhibit glucose production, or modulate glucose metabolism in various biological pathways of a subject. Thus, compositions and compounds comprising selenium may be administered alone or in combinations to an individual subject to, at risk of, or suffering from a disease or condition associated with aberration of the genes described herein. For example, the methods of the present application may find use in diagnosing or treating (e.g., prophylactically or therapeutically) a subject with a condition associated with Noninsulin-dependent (Type II) diabetes mellitus (DM).

In one embodiment of the present disclosure, a method of replacing insulin in a subject comprises administering a composition to the subject, the composition comprising at least three different compounds selected from the group consisting of: 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In another embodiment, an effective amount of the composition replaces insulin in liver cells of the subject as compared to liver cells of the subject not treated with the composition. In some embodiments, the composition comprises at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In embodiments, the composition comprises at least 0.05% (w/v) for each of the two compounds. In other embodiments, the composition comprises at least 0.033% (w/v) for each of the three compounds.

In another embodiment, a method of enhancing insulin activity in a subject comprises administering a composition to the subject, the composition comprising at least three different compounds selected from the group consisting of: 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In another embodiment, an effective amount of the composition enhances insulin activity in liver cells of the subject as compared to liver cells of the subject not treated with the composition. In some embodiments, the composition comprises at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In embodiments, the composition comprises at least 0.05% (w/v) for each of the two compounds. In other embodiments, the composition comprises at least 0.033% (w/v) for each of the three compounds. An additional embodiment of the method of enhancing insulin activity in a subject, further comprises administering insulin or an analog or derivative thereof.

In yet another embodiments, a method of inhibiting glucose production in a subject comprises administering a composition to the subject, the composition comprising at least three different compounds selected from the group consisting of: 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In another embodiment, an effective amount of the composition inhibits glucose production in liver cells of the subject as compared to liver cells of the subject not treated with the composition. In some embodiments, the composition comprises at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In embodiments, the composition comprises at least 0.05% (w/v) for each of the two compounds. In other embodiments, the composition comprises at least 0.033% (w/v) for each of the three compounds.

In another embodiment, a method of increasing FOXO3 and/or FOXO 4 phosphorylation in a subject comprises administering a composition to the subject comprising at least two compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In another embodiment, an effective amount of the composition increases FOXO3 and FOXO4 phosphorylation in liver cells of the subject as compared to liver cells of the subject not treated with the composition. In some embodiments, the composition comprises at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In embodiments, the composition comprises at least 0.05% (w/v) for each of the two compounds. In other embodiments, the composition comprises at least 0.033% (w/v) for each of the three compounds.

In embodiments, a method of modulating glucose metabolism in a subject comprises: administering an effective amount of a composition to the subject, the composition comprising at least two different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III). In another embodiment, an effective amount of the composition modulates glucose metabolism in liver cells of the subject as compared to liver cells of the subject not treated with the composition. In some embodiments, the composition comprises at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In embodiments, the composition comprises at least 0.05% (w/v) for each of the two compounds. In other embodiments, the composition comprises at least 0.033% (w/v) for each of the three compounds.

In embodiments, a method of increasing glucose sensitivity in a subject comprises administering a composition to the subject, the composition comprising at least two different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In another embodiment, an effective amount of the composition increased glucose sensitivity in liver cells of the subject as compared to liver cells of the subject not treated with the composition. In some embodiments, the composition comprises at least three different compounds selected from the group consisting of 5'-Methylselenoadenosine, Se-Adenosyl-L-homocysteine, Gamma-glutamyl-methylseleno-cysteine, a compound of Formula (I), Formula (II), a compound of Formula (III), and combinations thereof. In embodiments, the composition comprises at least 0.05% (w/v) for each of the two compounds. In other embodiments, the composition comprises at least 0.033% (w/v) for each of the three compounds.

In embodiments, a method of treating diabetes in a subject comprises administering a composition to the subject, the composition comprising at least two different compounds selected from the group consisting of: 5'-Methylselenoadenosine, Se-Adenosyl-L-homocysteine, Gamma-glutamyl-methylseleno-cysteine, a compound of Formula (I), a compound of Formula (II), a compound of Formula (III) and combinations thereof. In another embodiment, an effective amount of the composition treats diabetes in liver cells of the subject as compared to liver cells of the subject not treated with the composition. In some embodiments, the composition comprises at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In embodiments, the composition comprises at least 0.05% (w/v) for each of the two compounds. In other embodiments, the composition comprises at least 0.033% (w/v) for each of the three compounds.

In some embodiments, a method or use is provided for inhibiting expression of G6PC in a subject comprising administering a composition to the subject, the composition comprising at least two compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In another embodiment, an effective amount of the composition inhibits G6PC gene expression in liver cells of the subject as compared to liver cells of the subject not treated with the composition. In some embodiments, the composition comprises at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In embodiments, the composition comprises at least 0.05% (w/v) for each of the two compounds. In other embodiments, the composition comprises at least 0.033% (w/v) for each of the three compounds.

In some method embodiments, a decrease in G6PC ranges from an approximately 50% increase or decrease to a 500% increase or decrease as compared to a cell of identical type not treated with the compound. The magnitude of the G6PC response depends on the cell type, the specific compound, and the time in contact with the cell.

In other embodiments, a method or use is provided for increasing expression of insulin receptor (INSR) in a subject comprising administering a composition to the subject, the composition comprising at least two compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III) and combinations thereof. In another embodiment, an effective amount of the composition increases expression of insulin receptor in liver cells of the subject as compared to liver cells of the subject not treated with the composition. In some embodiments, the composition comprises at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In embodiments, the composition comprises at least 0.05% (w/v) for each of the two compounds. In other embodiments, the composition comprises at least 0.033% (w/v) for each of the three compounds.

In embodiments, a method or use is provided for increasing expression of insulin-like growth factor receptor (IGF1R) in a subject comprising administering a composition to the subject, the composition comprising at least two compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III) and combinations thereof. In another embodiment, an effective amount of the composition increases expression of insulin-like growth factor receptor in liver cells of the subject as compared to liver cells of the subject not treated with the composition. In some embodiments, the composition comprises at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III), and combinations thereof. In embodiments, the composition comprises at least 0.05% (w/v) for each of the two compounds. In other embodiments, the composition comprises at least 0.033% (w/v) for each of the three compounds.

In any one of the methods described herein, the composition can comprise 5'-Methylselenoadenosine, Se-Adenosyl-L-homocysteine, Gamma-glutamyl-methylseleno-cysteine or mixtures thereof. In any one of the methods described herein, the composition can comprise at least about 0.1% (w/v) of 5'-Methylselenoadenosine.

In any one of the methods described herein, the composition can be in a dried or capsular form. In any one of the methods described herein, the composition can further comprise insulin or an analog or derivative thereof. In any one of the methods described herein, the composition can further comprise an insulin sensitizer, an insulin secretagogue, or an incretin mimetic.

In any one of the methods described herein, the composition may exclude one or more of 5'-Methylthioadenosine, S-Adenosyl-L-homocysteine or Gamma-glutamyl-methyl-cysteine. In any one of the methods described herein, the composition can be administered orally.

In any one of the methods described herein, the composition can be administered to one or more liver cells of the subject. In some embodiments, any of the methods as described herein further comprise administering insulin or analog thereof or further comprise administering a different therapeutic agent for modulating glucose metabolism or treating diabetes.

In embodiments of the methods of the present application, a use is provided for a composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), and a compound of Formula (III) for replacing insulin or enhancing insulin activity in a subject. In embodiments, the use further comprises insulin or an analog thereof. In embodiments, the use further comprises a different therapeutic agent for modulating glucose metabolism or treating diabetes. In other embodiments of the present application, a use is provided for a composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), a compound of Formula (III) and combinations thereof for inhibiting G6PC in liver.

Selenium containing compounds affect gene expression in liver cells differently than neuronal cells. In contrast to the effect that compounds and compositions have on liver cells as described herein, the same or a similar composition can affect neuronal cells in an opposite way. For example, a composition as described herein, decreases the phosphorylation of FOXO3 and/or FOXO4 in neuronal cells, rather than increases FOXO3 or FOXO4 expression as specified in the methods of the present disclosure.

In additional embodiments of the method of the present disclosure, the effective amount of compounds and compositions as described herein is an amount effective to inhibit expression of G6PC, decrease glucose production in liver cells, or increase FOXO phosphorylation in a liver cell without being toxic to the cells. The effective amounts of compounds selected do not show toxicity for any of the exemplified cells including mouse skeletal, human neuronal, or mouse liver cells. In addition, the composition comprising the compounds described herein do not adversely affect glucose metabolism in liver cells.

Methods of determining gene expression in a cell of a subject are known to those of skill in the art, and may include hybridization with primers and/or probes, such as on an array or by PCR methods. Arrays and/or primers for determining gene expression are commercially available. Primers and arrays or microarrays may be readily designed using publicly available sequences for the genes described herein, such as G6PC, FOXO3, FOXO4, INSR, and IGF1R. For example, Exemplary sequences for G6PC are found at NM_000151.3, GI:393537030, Gene ID: 2538; FOXO3 are found at NM_001455.3, GI:146260266, Gene ID: 2309; FOXO4 are found at NM_001170931.1, GI:283436082, Gene ID: 4303; INSR are found at NM_000208.2, GI:119395735, Gene ID: 3643; and IGF1R are found at XM_011521513.1, GI:767983996, Gene ID: 3480. Modulation of gene expression in liver cells can be determined as described herein using a number of assays on a sample taken from a subject treated in accord with the compositions described herein.

As is well known in the medical or research arts, dosages for any one subject may depend upon many factors, including, but not limited to, the patient's size, body surface area, age, the particular compound to be administered, sex, timing, and route of administration, general health, and interaction with other drugs being concurrently administered. In embodiments, the dose of the present composition may be adjusted depending on efficacy or the presence of overt signs of selenium toxicosis are observed in the subject. Selenium toxicosis may be indicated by symptoms including, but not limited to, garlicky breath, hair loss, or flaky nails.

In some embodiments, the dose of the present composition is administered at least once daily for a period of time to achieve a steady state of elemental selenium in the blood. In yet other embodiments, the dose of the present composition may be administered while the subject is experiencing symptoms of a disease or disorder.

EXAMPLES

The following examples provide illustrative examples or embodiments of the compositions, compounds, and methods of the present disclosure. Illustrative embodiments of the compounds, composition, and methods of the present disclosure are provided herein by way of examples. While the concepts and technology of the present disclosure are susceptible to various modifications and alternative forms, specific embodiments thereof have been shown by way of example in the figures and will be described here in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

It will be appreciated that the technology described herein has broad applications. The foregoing embodiments were chosen and described in order to illustrate principles of the technology as well as some practical applications. While certain embodiments have been described and/or exemplified herein, it is contemplated that considerable variation and modification thereof are possible.

Example 1

Synthesis and Characterization of 5'-Methylselenoadenosine ("Compound C")

The synthesis scheme and methodology to produce Compound C was:

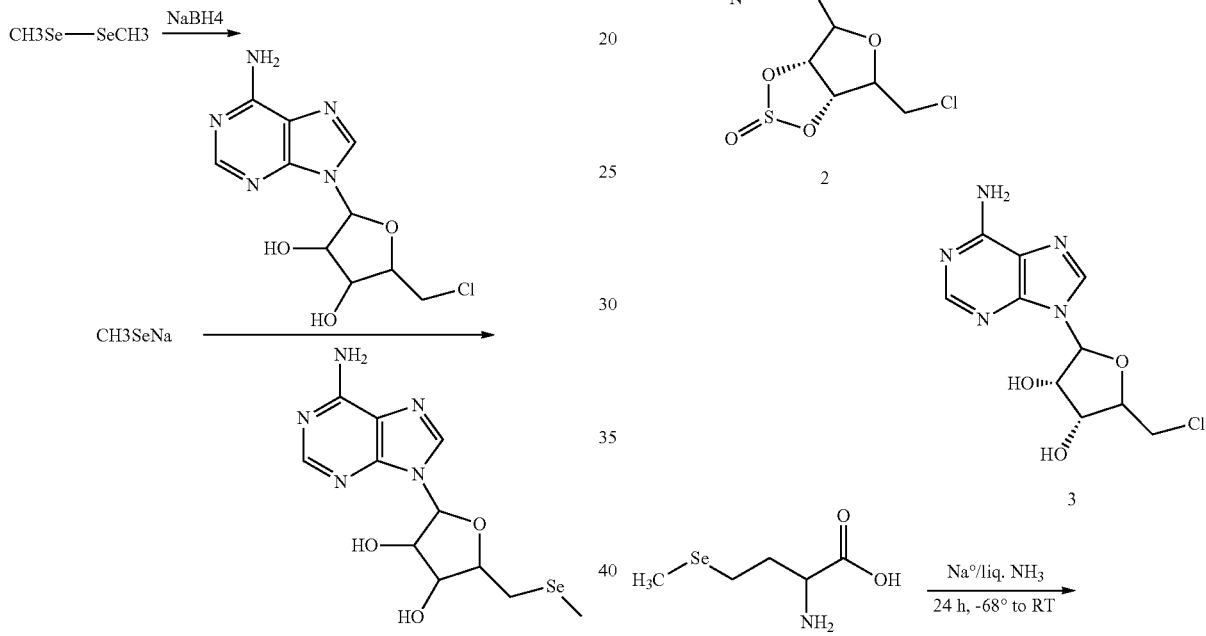

Sodium borohydride (227 mg, 6.0 mM, under Ar°) was placed in a 200 mL round-bottom flask containing 20 mL of anhydrous ethyl alcohol, equipped in a magnetic stirrer and located in an ice cooling bath. Dimethyldiselenide (190 uL, 376 mg, 2.0 mM), was added to the flask with cooling, stirring and under Ar flow. After formation of a yellowish solution, solid 5'-chloro-5'-deoxyadenosine (1.143 g, 4.0 mM) was added. 100 mL of ethyl alcohol was added to dissolve the precipitate. The mixture was stirred at room temperature for the following four days. Mass Spectrometry was used to monitor the approximately 75% conversion that was accomplished after five days. The solvents were evaporated, and 3.22 g of the product (with approximately 20% of starting material (SM)) was collected and purified by the reverse phase (C-8) preparative chromatography. A yield of 1.1 g of pure product was collected, which had its molecular weight confirmed by mass spectrometry.

Example 2

Synthesis and Characterization of Se-Adenosyl-L-homocysteine ("Compound D")

The synthesis scheme and methodology to produce Compound D is shown below in steps 1-6:

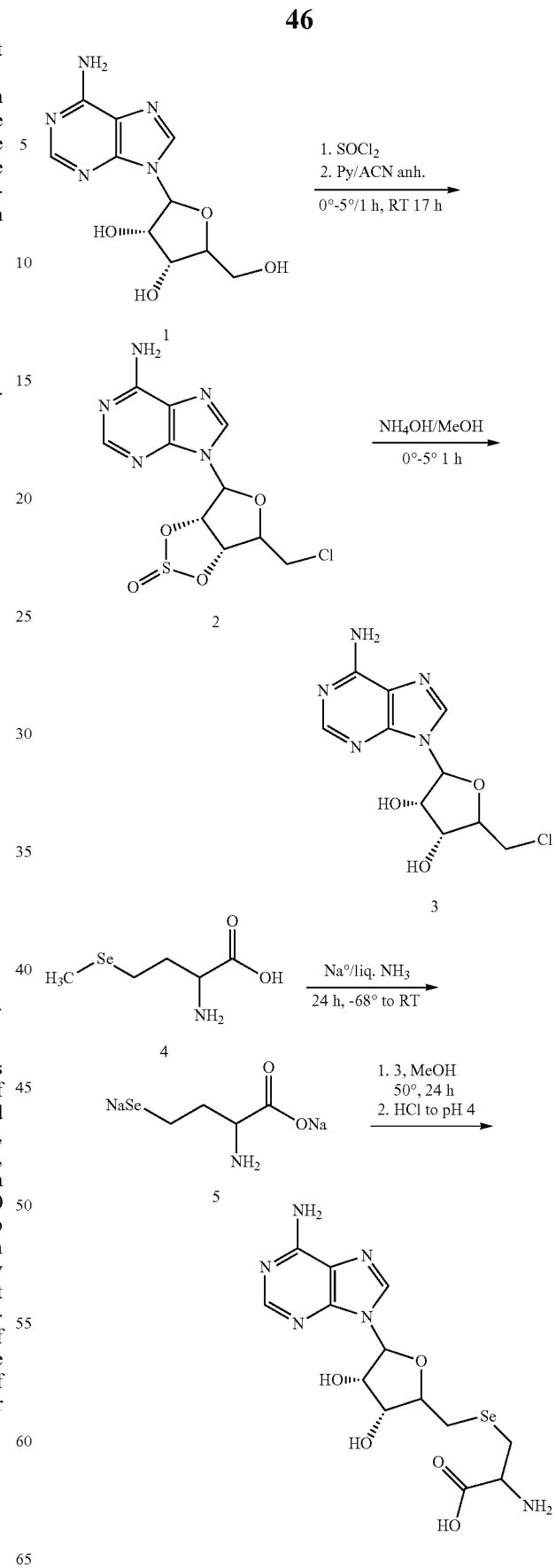

5'5'-Chloro-S'-deoxyadenosine (639-62)

Eighty-nine (89) grams (0.366 mole, 1 eq.) adenosine, 59.3 mL (58, 1.833 mole, 2 eq.) anhydrous pyridine and 1 L anhydrous acetonitrile were placed in an oven dried, 2 L, 4 neck flask, equipped in a dropping funnel, a stirrer, gas inlet/outlet and a thermometer. The reaction set was placed in an ice/salt bath and agitation was initiated. When the temperature of the solution dropped below 3° C., thionyl chloride was added slowly. The temperature of the reaction mixture was maintained below 5° C. during thionyl chloride addition and for 4 h more (at this time the solution is yellow with white-yellow precipitate on the bottom). The reaction was left overnight at ambient temperature.

The next morning the voluminous precipitate was filtered off using sintered glass filter and washed on the filter with 300 ML volume of dry acetonitrile. During this time, the precipitate color changed into white. The wet precipitate was then transferred back into the 2 L reaction flask containing a mixture of 800 ML of methanol and 160 ML of water. Eighty milliliters (80 ML) of concentrated ammonium hydroxide solution was added drop-by-drop to the reaction flask with mechanical stirring and cooling with a water bath. The mixture was agitated for 45 min at ambient temperature and a white precipitate formed, which was separated from the liquid by vacuum filtration.

The filtrate was concentrated to dryness using a vacuum rotary-evaporator while the precipitate was crystallized from approximately 560 ML hot water. The precipitate was cooled in an ice-water bath, and the first crop of the crystals was filtered off and freeze-dried. The filtrate was used as a solvent in the crystallization of solids, which resulted from the rotary evaporation of the first filtrate to obtain the second crop of the product. The second crop of the product was freeze-dried for two days. Both crops of crystals were finally dried for two days over phosphorous pentoxide in a vacuum dessicator. Eighty-four (84) grams of white crystals, with a 80.5% yield were obtained. MS(286-M+H), mp.187° C. Selenoadenosylhomocysteine (655-40).

L-selenomethionine (9.806 gram, 50 mM, 1 eq.) was charged into a 2 L, three-neck flask equipped in a thermometer, a large cooling finger (with bubble-meter at the outlet), ammonia gas inlet (reaching bottom of the flask) and a magnetic stirring bar and placed in a 2.5 L duar vessel containing $CO_2$-Acetone cooling bath. Ar° was passed through the flask before adding solid $CO_2$ to the acetone bath and the cooling finger. When the temperature inside the flask dropped below −35° C. the flow of anhydrous ammonia (gas) was started and when liquid ammonia levels reached the volume of 800 ML the gas flow was stopped.

Small pieces of metallic sodium were added to a well stirred solution until blue-violet coloration of the solution persisted for approximately 30 sec. A total of 2.645 gram (115 mM, 2.3 eq.) of sodium was added within 45 min Agitation and cooling were maintained for 30 min more. At this time all of the components were in the solution. Anhydrous 5'-chloro-5'-deoxyadenosine (14.856 gram, 52 mM, 1.04 eq.) was added in a single portion and the reaction mixture was left with stirring and very slow Ar° flow overnight.

The next morning, 350 ML of anhydrous methanol was added to the white solids which were present in the flask. The flask was placed in an oil bath, a reflux condenser was installed, Ar° gas flow was maintained, and an oil bath was heated to 50° C. for the subsequent 24 hours. One milliliter (1 ML) of the solution was acidified to pH 3.5 with a few drops of 0.1N HCl, and the sample was analyzed for the presence of substrates using mass spectrometry.

If below 5%, the mixture can be acidified with 1N HCl to pH 3.5, filtered from salts, concentrated to dryness using vacuum rotary-evaporator and the crude product can be purified by crystallization from water-ethanol mixture. The first crop of Selenoadenosylhomocysteine crystals yielded 15.98 gram of product with a 74% yield. Yet, approximately 95% of the product was clean, and could be used in biological studies without further purification.

Example 3

Synthesis and Characterization of Gamma-Glutamyl-Methylseleno-Cysteine ("Compound E")

The synthesis scheme and methodology to produce Compound E is shown below with steps 1-4:

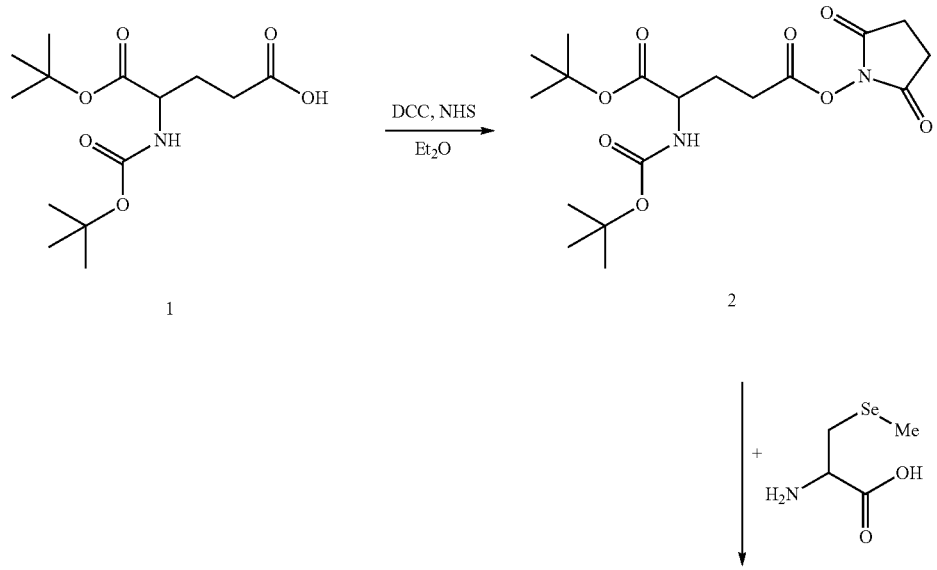

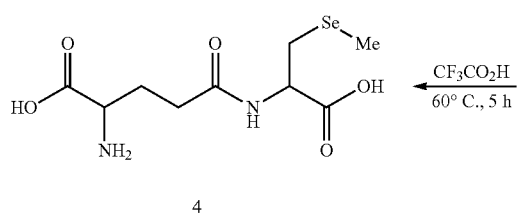 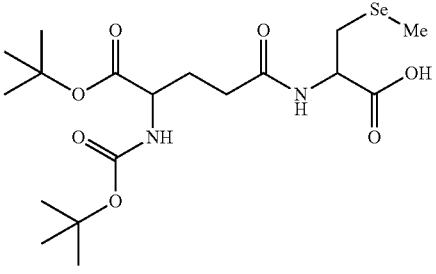

4 3

Synthesis of N-Boc-(O-tBu)-L-Glu-OSe (655-90)

N-Boc-(O-tBu)-L-Glu-OH (303 mg, 1.0 Mmol), N-hydroxysuccinimide (121 mg, 1.05 Mmol) and dicyclohexyl carbodiimide (227 mg, 1.1 Mmol) were suspended/dissolved in 15 ML of anhydrous ethyl ether and 10 uL of dimethylethylbenzylamine was added from a syringe into the reaction mixture. Stirring at ambient temperature (22° C.) was maintained for 48 h. The mixture was filtered and the precipitate was washed 10×10 mL of ethyl ether. The filtrate was concentrated and dried under high vacuum yielding white crystalline product (570 mg, ~90% yield). MS (M+Na$^+$)=423.17.

Synthesis of N-Boc-(O-tBu)-L-Glu-MeSe-Cys-OH (655-90)

N-Boc-(O-tBu)-L-Glu-OSe(570 mg, 0.9 Mmol), methylselenocysteine (175 mg, 0.8 Mmol), triethylamine (152 mg, 209 µL, 1.5 Mmol) were added into a mixture of 6 mL of 1,4-Dioxane and 2 mL of water. Magnetic stirring of the reaction mixture was maintained for 100 h. After this time 1.21M HCl (1.65 mL) was added and the post-reaction mixture was extracted with three rounds (3×) of 20 mL of ethyl ether. The extract was concentrated to dryness using a vacuum rotary-evaporator yielding 649 mg of waxy product that was submitted to preparative HPLC. Two hundred eighty-three milligrams (283 mg) of the product were collected having a 75.6% yield. Mass spectrum confirmed the molecular weight of the product, and the presence of a single Se atom in it. Calculated mass for $C_{18}H_{32}N_2O_7Se$=468.42; These results found 469.24 m/e (M+H$^+$) and 491.24 m/e (M+Na$^+$).

Synthesis of Y-Glutamyl-methylselenocysteine (655-92)

A mixture of 283 mg (0.6 Mmol) of N-Boc-(O-tBu)-L-Glu-MeSe-Cys-OH, 2 mL of thioanisol, and 5 mL of trifluoroacetic acid were heated with magnetic stirring in an oil bath for 6 hours and at 63° C. The mixture was left over night at ambient temperature (22° C.). The reaction mixture was added drop-by-drop into 20 ML of a vigorously stirred ethyl ether. The precipitate that formed was washed with two rounds (2×) of 20 ML of ethyl ether. The product yielded 138.3 mg of creamy precipitate, which was then purified by preparative HPLC.

Example 4

Synthetic individual selenoorganic compounds, combinations of the individual selenoorganic compounds, and their sulfur analogs were tested in cell culture (in vitro) for effects on cell survival or viability and gene expression in the examples described herein. In particular, the cells tested were mouse AML-12 liver cells.

Materials and Methods

Cell Lines and Compounds

The mouse liver cell line AML-12 and human neuroblast IMR-32 cells were purchased from the American Type Culture Collection (ATCC, Manassas, Va.). AML-12 cells were amplified in Dulbecco's modified Eagle's medium and Ham's F12 (DMEM/F12) media supplemented with 10% fetal bovine serum (FBS), 40 ng/ml dexamethasone (Dex, Sigma) and 1×ITS (containing 0.01 mg/ml bovine insulin, 0.0055 mg/ml human transferrin, 5 ng/ml sodium selenium) solution (Sigma). IMR-32 cells were cultured in Eagle's Minimum Essential Medium (EMEM) supplemented with 10% FBS.

Compound C (5'-Methylselenoadenosine), Compound D (Se-Adenosyl-L-homocysteine), and Compound E (Gamma-glutamyl-methylseleno-cysteine), and their sulfur analogs, Compound H (5'-Methylthioadenosine), Compound I (S-Adenosyl-L-homocysteine), and Compound J (Gamma-glutamyl-methyl-cysteine) were either synthesized or obtained from commercial sources (where available). The purities of all tested compounds were verified to be ≥99%, as determined by Mass-Spectrometry. Three batches of the above synthesized compounds were used in the following experiments.

The ppb values shown in the examples herein refer to ppb of selenium in selenium containing compounds or ppb sulfur in sulfur containing compounds in order to ensure equivalent amounts of selenium or sulfur were being tested in the experiments.

In order to convert ppb based on selenium to ppb of the compound, the % of Se in a compound is calculated by dividing the atomic weight of selenium by the molecular weight of the compound and multiplying the dividend by 100. In order to convert ppb based on sulfur to ppb of the compound the % of S in a compound is calculated by dividing the atomic weight of sulfur by the molecular weight of the compound and multiplying the dividend by 100.

For example, dividing the atomic weight of Selenium of 78.96 by the molecular weight of Compound C of 344 and multiplying the result by 100, results in a % of selenium in Compound C of 23%. Likewise, for Compound D, dividing the atomic weight of Selenium of 78.96 by the molecular weight of Compound D of 432 and multiplying the result by 100, results in a % of selenium in Compound D of 18%. For Compound E, dividing the atomic weight of Selenium of 78.96 by the molecular weight of Compound E of 311 and multiplying the result by 100, results in a % of selenium in Compound E of 25%.

These % Se values are used to derive factors for converting ppb of selenium to ppb of the compound. These factors are: 4.35 for Compound C, 5.46 for Compound D, and 3.94 for Compound E. In order to convert ppb based on selenium to ppb of the compound multiply the indicated ppb of selenium by the factor for each compound as shown in the Table below. For example, 150 ppb of Compound C in the experiments below refers to 150 ppb of selenium and is equivalent to 653 ppb of Compound C.

For the sulfur compounds, dividing the atomic weight of Sulfur of 32 by the molecular weight of Compound H of 297, and multiplying the result by 100, results in a % of sulfur in Compound H of 11%. Likewise, for Compound I, dividing the atomic weight of Sulfur of 32 by the molecular weight of Compound I of 384 and multiplying the result by 100, results in a % of sulfur in Compound I of 8%. For Compound J, dividing the atomic weight of Sulfur of 32 by the molecular weight of Compound J of 264 and multiplying the result by 100, results in a % of sulfur in Compound J of 12%.

These % S values are used to derive factors for converting ppb of sulfur to ppb of the compound. These factors are: 9.28 for Compound H, 12.00 for Compound I, and 8.25 for Compound J. In order to convert ppb based on sulfur to ppb of the compound multiply the indicated ppb of sulfur by the factor for each compound as shown in the Table below. For example, 150 ppb of Compound H as described in the experiments below refers to 150 ppb of sulfur and is equivalent to 1392 ppb of Compound H.

| ppb Selenium Delivered by the Compound | Equivalent ppb Compound C | Equivalent ppb Compound D | Equivalent ppb Compound E |
| --- | --- | --- | --- |
| 100 | 435 | 546 | 394 |
| 150 | 653 | 819 | 591 |
| 200 | 870 | 1092 | 788 |
| 300 | 1305 | 1638 | 1182 |
| 450 | 1958 | 2457 | 1773 |
| 600 | 2610 | 3276 | 2364 |
| 900 | 3915 | 4914 | 3546 |

| ppb Sulfur Delivered by the Compound | Equivalent ppb Compound H | Equivalent ppb Compound I | Equivalent ppb Compound J |
| --- | --- | --- | --- |
| 100 | 928 | 1200 | 825 |
| 150 | 1392 | 1800 | 1238 |
| 200 | 1856 | 2400 | 1650 |
| 300 | 2784 | 3600 | 2475 |
| 450 | 4176 | 5400 | 3712 |
| 600 | 5568 | 7200 | 4950 |
| 900 | 8352 | 10800 | 7425 |

Cell Viability Assay

Cell viability in cultured AML-12 was determined using Promega's CellTiter96® AQueous One Solution Cell Proliferation Assay kits, according to the manufacturer's protocol and instructions. In brief, AML-12 ($1\times10^4$ cells/well) were seeded on 96-well clear plates (VWR) and cultured in DMEM/F12 media containing 10% FBS, 1×ITS and 40 ng/ml Dex overnight. Cells were than treated with control (water) or compounds in ITS-free DMEM/F12 media containing 10% FBS and 40 ng/ml Dex for 48 hours.

The cultured cells were incubated with AQueous One solution (100 ul/per well) at 37° C. for 1 hour, and the absorbance of OD490 nm in each sample was determined by the Bio-Tek microplate reader. Cell viability in culture cells were determined by the subtraction of OD490 nm in cultured cells with the OD490 nm in plain culture media (without seeding of cells). Eight samples per each treatment were examined for the above analysis. Data are presented as Mean±SEM of eight samples.

Cell Treatments for RNA and Protein Analysis

For RNA analysis of insulin receptor (Insr), insulin like growth factor receptor (Igf1r), and Glucose-6-Phosphatase (G6pc), AML-12 cells were amplified in ITS, Dex and FBS-containing DMEM/F12 media, and cultured on 24-well ($6.7\times10^4$ cells/well) plates in 10% FBS ITS-free DMEM/F12 media with or without Dex overnight. These cells were treated with control (water) or various compounds (diluted in 10% FBS ITS-free DMEM/F12 media with or without Dex) for 6 hours, 24 hours, or 48 hours.

In some experiments, the AML-12 cells were washed twice with PBS after the compound treatments for 24 hours, and then incubated with selenium compounds (150 or 300 ppb of each compound) in the presence or absence of insulin (10 or 100 nM), 0.1 mM 8-CPT (Sigma), or 0.5 µM Dex in serum-free, glucose/phenol red-free DMEM media supplemented with 20 mM lactose and 2 mM pyruvate, and 15 mM HEPES (glucose-production media) for another 6 hours. After treatments, cell media were collected and subjected to glucose assays using Abcam glucose assay kit according to the manufacturer's protocol. Cells lysed and collected for RNA isolation and PCR analysis of G6pc, Insr and Igf1r.

For the studies of protein expression, AML-12 cells were amplified in ITS, Dex and FBS-containing DMEM/F12 media, and cultured on 6-well ($3.33\times10^5$ cells/well) plates in 10% FBS ITS-free DMEM/F12 media with or without Dex overnight. These cells were treated with control (water) or various compounds in either serum containing (10% FBS ITS-free DMEM/F12 media supplemented with Dex) or serum-free (ITS/Dex-free DMEM/F12 media) for 6 hours and 24 hours. In addition, human neuroblast IMR-32 cells were cultured in 10% FBS EMEM media and then treated with control (water), selenium compounds and their sulfur analogs in the same serum-containing media for 6 hours and 24 hours.

RNA Isolation and Real-Time PCR Analysis

Total RNA from these cells was isolated using Trizol (Invitrogen) according to the manufacturer's protocol, and then incubated with DNase I to remove any potential contaminated genomic DNA. RNA samples were subjected to real-time PCR analysis using the Applied-Bioscience's RT kit and predesigned Taqman probes (Invitrogen), as described previously (Lan et al EMBO J 2003). Three to six samples were analyzed in each treatment group. Data were normalized by Actin B (Actb) mRNA levels in each sample and are presented as mean±SEM of 3-6 samples.

Protein Preparation and Western Blot Analysis

AML-12 liver cells or IMR-32 neuronal cells were seeded on 6-well plates, and then treated with vehicle and various compounds for 6 hours and 24 hours, as described herein. After treatments, cells were rinsed with ice-cold PBS and lysed in the ice-cold RIPA buffer containing complete proteinase and phosphatase inhibitors (Thermo-Fisher Scientific, Waltham, Mass.) on ice for 30 min Cell lysates were collected using a cell scraper and transfer pipette, and then centrifuged at 12000×g for 30 min at 4° C. to remove the DNA pellet and obtain the protein extract. Protein levels in the supernatant of these cell lysates were determined using the Pierce Micro-BCA protein assay kit (Thermo Scientific-Piece Biotechnology, Rockford, Ill.) according to the manufacturer's protocol.

For Western blot analysis, five micrograms of total proteins from control- and compound(s)-treated cells were subjected to SDS-PAGE gel separation, and then transferred to PVDF membranes, as described previously (Reddy, Liu et al. 2008 Science). Membranes were blocked in a phosphate-buffered saline (PBS) containing 5% (w/v) of bovine serum albumin (Sigma, St. Louis, Mo.), and incubated with specific primary antibodies. The membranes were then incubated with HRP-conjugated anti-mouse or anti-rabbit secondary antibodies (1:5000 dilution, Cell Signaling, Inc.).

All primary antibodies except Actb (Li-COR, Lincoln, Nebr.), Elf2bε and pElf2bε (Abcam, Cambridge, Mass.) were purchased from Cell Signaling Inc. Positive signals on the membrane blots were detected using the Amersham's enhanced chemiluminescence Western Blotting Prime Detection reagents (GE healthcare Lifescience, Pittsburgh, Pa.). Images of luminescence signals on the membrane blots were captured using the LI-COR Odyssey Fc Image system (Lincoln, Nebr.). The same membrane blot was stripped and re-blotted with another antibody as described in the GE WB ECL-prime-detection protocol (GE healthcare Lifescience, Pittsburgh, Pa.). Protein band densities in the Western blots were determined using the Li-COR Image studio software or NIH ImageJ software and then normalized by Actb level in each sample. Data are presented as mean±SEM of three samples per each group.

Statistical Analysis

Where applicable, a Student's t-test was used to determine the statistical significance of difference between saline-treated and Compounds CDE-treated groups with a p value less than 0.05.

Results and Discussion:

Effect of Compounds CDE on Viability of AML-12 Cells

To test whether there is any toxic effect of selenium compounds on the survival of AML-12 cells, cell viability assays were performed on liver cells. AML-12 cells were treated with a water control or 150 ppb of individual Compound C, Compound D, Compound E, Compound H, Compound I and Compound J; combinations of Compounds I and J ("Compound IJ"); combinations of Compound D and Compound E ("Compound DE"); and combinations of Compound C, Compound D, and Compound E ("Compounds CDE") for 48 hours.

Figure 1:
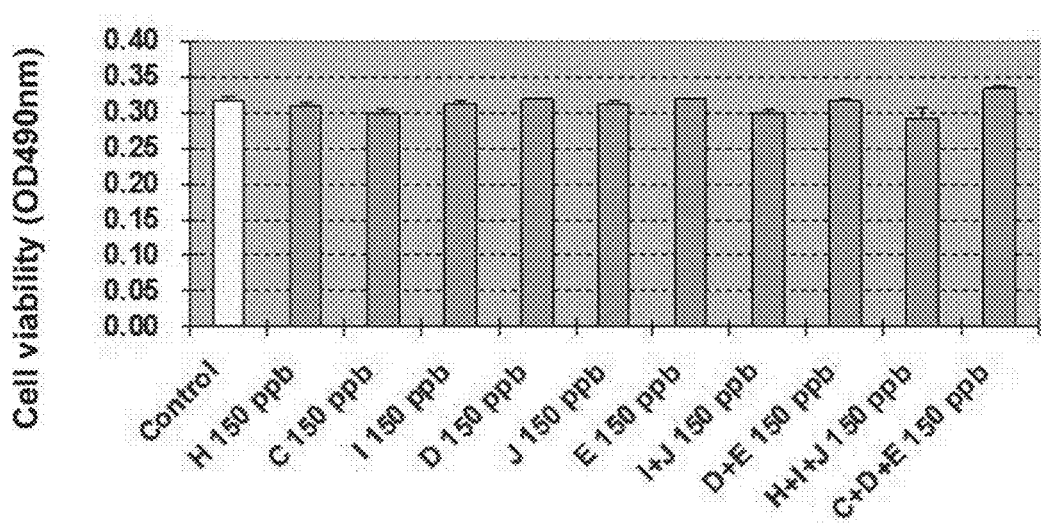
FIG. 1 is a graph showing the effect of 150 ppb of each of individual compounds and various combinations of Compound C, Compound D, Compound E, Compound H, Compound I, and Compound J on cell viability in AML-12 liver cells as indicated by OD490.

No compound treatment, including both single compounds and compound combinations, caused a significant decrease of cell viability (indicated by OD490 nm) in AML-12 cells when compared to the control group (FIG. 1). These results demonstrated that selenium Compounds CDE did not have any negative effect on the survival or viability of AML-12 cells.

Inhibition of G6pc mRNA Expression by Compounds CDE in AML-12 Cells Cultured in FBS- and Dex-Containing Media without ITS Liver is the main organ to produce glucose for maintaining normal glucose levels in the blood stream. Glucose-6-Phosphatase Catalytic subunit (G6pc) is an essential enzyme for gluconeogenesis in the liver. To explore the potential function of Compounds CDE in the liver, G6pc expression was examined by QRT-PCR analysis in AML-12 cells cultured under various conditions described herein.

It is recommended that AML-12 cells should be cultured or amplified in media containing serum-, Insulin-Transferrin-Sodium selenite supplement (ITS) and Dexamethasone (Dex). To rule out the possibility that insulin and sodium selenite in ITS could interfere with the action of the tested selenium compounds in AML-12 cells, the G6pc expression in AML-12 cells cultured in ITS-free media but containing FBS and Dex was investigated. In brief, AML-12 cells were cultured/amplified in complete amplification media (10% FBS, ITS- and Dex-containing DMEM/F12), seeded on culture plates, and cultured in ITS-free FBS- and Dex-containing media overnight. These cells were treated with control (water), selenium individual compounds: Compound C, Compound D, Compound E at the dose of 150 ppb of each compound, and sulfur individual compounds: Compound H, Compound I, Compound J. A combination of Compounds CDE, and a combination of Compounds HIJ were also tested on the cells for 48 hours. After these treatments, cells were collected and subjected to QRT-PCR analysis.

Figure 2A:
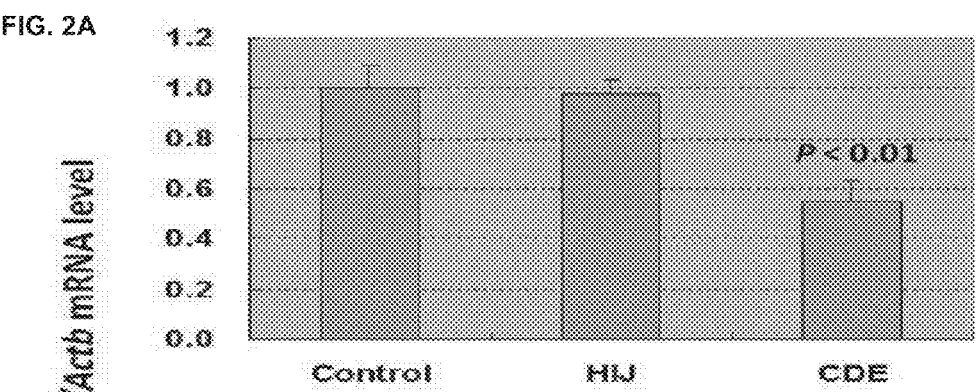
FIGS. 2A-2B show the effect of various combinations of Compound C, Compound D, Compound E, Compound H, Compound I and Compound J and the individual compounds on mRNA expression levels of the G6pc gene in AML-12 liver cells.
Figure 2B:
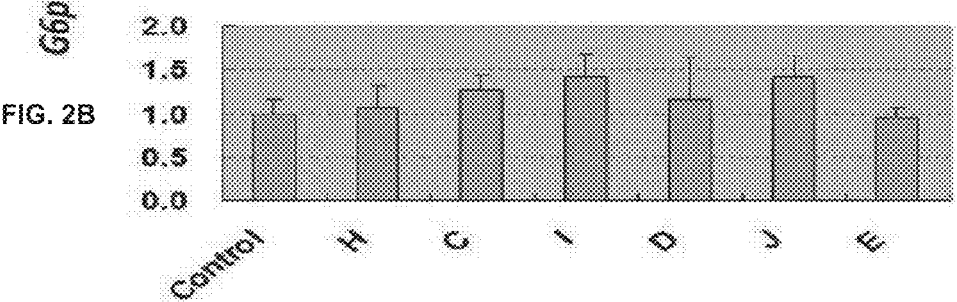

As shown in FIG. 2A, treatment of AML-12 liver cells with the Compounds CDE combination, but not the Compounds HIJ sulfur analog combination, caused a very significant (approximately 50%) decrease in G6pc expression in liver cells under the experimental conditions. In addition, G6pc expression was further examined in AML-12 cells after treatment with all of the individual compounds (see FIG. 2B). No significant alteration (e.g., increase or decrease) in G6pc expression was observed. Data are presented as mean±SEM of 4 samples.

The effect of decreased G6pc expression in response to the Compounds CDE combination was observed in three repeat experiments using different batches of cells (data not shown). This effect was not due to the potential toxic effects of selenium compounds on cell survival since Compounds CDE did not affect the viability of AML-12 cells under the same experimental conditions (see FIG. 1). These results demonstrate that Compounds CDE in combination, but not individual compounds or their sulfur analogs, can inhibit G6pc expression in AML-12 cells in the presence of FBS and Dex in culture media.

A Combination of Compounds CDE Inhibits G6pc Expression in AML12 Cells in ITS- and Dex-Free Media with FBS for 24 Hours Followed by Serum-Free Media for 6 Hours It has been reported that Dex can regulate G6pc expression in the liver. The effects of Compounds CDE in AML-12 cells under ITS/Dex-free culture conditions was investigated. Liver AML-12 cells cultured under serum-free conditions for 24 hours and 48 hours displayed some abnormal cell morphology. However, no gross morphological changes in AML-12 cells after culture in serum-free media for 6 hours was observed (data not shown). Thus, AML-12 cells were pretreated with Compounds CDE in serum-containing but ITS/Dex-free media for 24 hours followed by retreatment of these compounds in serum/ITS/Dex-free media for 6 hours to further investigate the effects of Compound CDE on G6pc expression.

In brief, AML-12 cells were treated with either 150 or 300 ppb Compounds CDE combination (diluted in 10% FBS but ITS/Dex-free media) for 24 hours. The cells were then washed twice with PBS to remove residual FBS, and incubated with the same doses of these selenium compounds in the presence or absence of 10 or 100 nM insulin (diluted in FBS/ITS/Dex-free media) for 6 hours. Insulin alone treatments were included for the comparison of the efficacy of the effects of Compounds CDE and the potential additive or synergistic actions between Compounds CDE and insulin.

Figure 3:
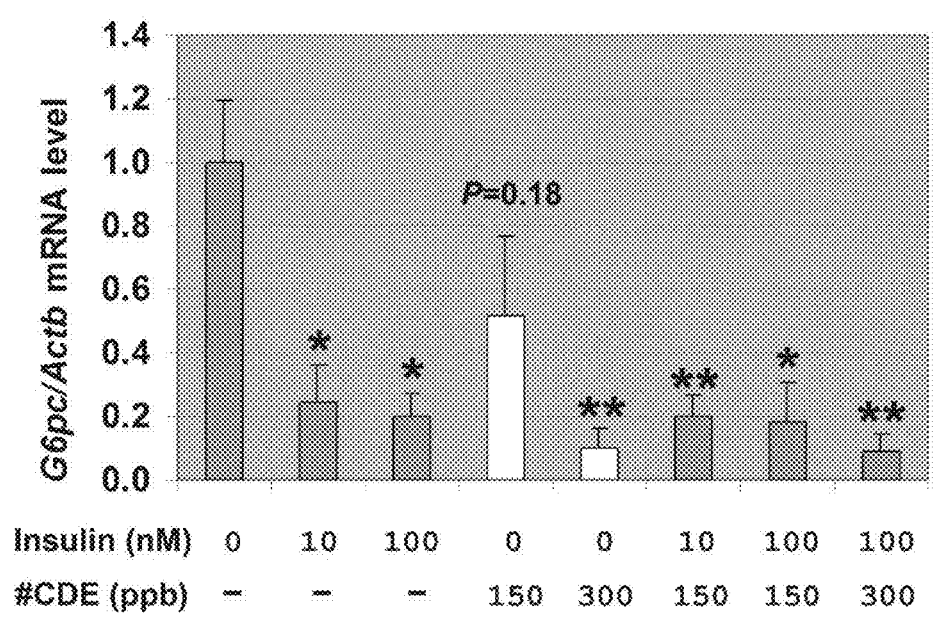
FIG. 3 is a bar graph showing the effects of insulin, Compounds CDE, and combinations of both insulin and Compounds CDE on relative G6pc mRNA expression levels in AML-12 cells. *, $P<0.05$, ** $P<0.01$ when compared to control group (without insulin and Compounds CDE treatment group).

As shown in FIG. 3, treatments of both doses of insulin (10 and 100 nM) significantly inhibited G6pc expression, which is expected. Treatment of Compounds CDE alone at the dose of 150 ppb caused a trend of reduction in G6pc expression (FIG. 3). More dramatically, Compounds CDE treatments at the dose of 300 ppb caused a robust and significant reduction in G6pc expression in these AML12 liver cells, with the efficacy at least comparable to 100 nM insulin (FIG. 3). In addition, the tested combination of insulin treatment with 150 or 300 ppb Compounds CDE also resulted in a significant reduction in G6pc mRNA expression, when compared to the control (FIG. 3). The results clearly demonstrate that Compounds CDE can mimic insulin to inhibit G6pc expression in AML-12 cells and the effective dose of 300 ppb Compounds CDE is comparable to 100 nM insulin.

Inhibition of G6pc Expression and Improvement of Insulin Action in the Regulation of G6pc Expression by Compounds CDE in AML-12 Cells Cultured Under Simulated Diabetic Conditions (Stimulated by Both cAMP and Dex)

To further investigate the effects of Compounds CDE on G6pc expression, G6pc mRNA expression in AML-12 cells cotreated with cell-permeable 8-(4-chlorophenylthio) cAMP (8-CPT) and Dexamethasone (Dex) were examined Cyclic AMP (8-CPT) and Dex are well known stimuli of G6pc expression and glucose production in the liver, which mimics diabetic conditions in vivo. In brief, AML-12 liver cells were pretreated with water (control) or 150 ppb or 300 ppb of Compounds CDE combination in 10% FBS but ITS/Dex-free media for 24 hours.

This initial treatment was followed by retreatment of these selenium compounds in the presence or absence of 10 nM or 100 nM insulin, 0.1 mM 8-CPT, and 0.5 µM Dex in serum-free media for 6 hours. After these treatments, cells were collected and subjected to QRT-PCR analysis. Data are presented in FIG. 4 as mean±SEM of four samples per each group. Different letters (a vs b, a' vs b' vs c', a" vs b" vs c") in FIG. 4 mean a significant difference between those two groups.

Figure 4:
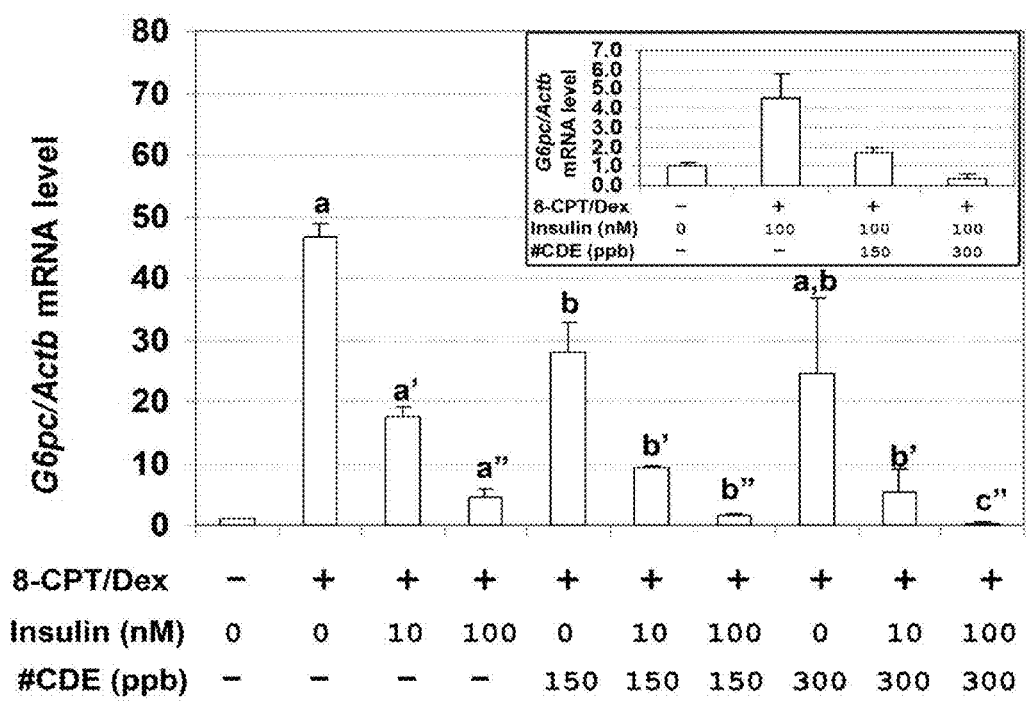
FIG. 4 is a bar graph showing the effects of insulin, Compounds CDE, and combinations of both insulin and Compounds CDE on relative G6pc mRNA expression levels in AML-12 cells cotreated with 8-CPT/Dex. The inset figure is a bar graph with a high magnification showing relative G6pc mRNA expression levels in AML-12 cells treated with water alone (control), a combination of 8-CPT/Dex and insulin, and combinations of 8-CPT/Dex, insulin, and Compounds CDE.

As shown in FIG. 4, AML-12 liver cells treated with 8-CPT/Dex showed a great increase in the expression of G6pc mRNA. Treatment with both doses of insulin significantly decreased 8-CPT/Dex-induced G6pc expression in AML-12 cells (when compared to 8-CPT/Dex group in the bar graph in FIG. 4). More importantly, Compounds CDE at the dose of 150 ppb also significantly attenuated 8-CPT/Dex-induced G6pc expression. The mean levels of G6pc expression were further reduced in AML-12 cells after treatments of 8-CPT/Dex and the combination of Compounds CDE at a higher dose (300 ppb), even though the P value was greater than 0.05 (when compared to 8-CPT/Dex group) due to the high variation of G6pc expression in this treatment group. Regardless, these studies demonstrated that, like insulin, Compounds CDE alone at the tested doses can inhibit 8-CPT/Dex-induced G6pc expression (about a 40-48% reduction when compared to the 8-CPT/Dex group).

In addition, treatment of Compounds CDE at 150 ppb dose in combination with 10 nM insulin, along with 8-CPT/Dex, further inhibited G6pc expression in AML-12 cells when compared to the 10 nM insulin and 8-CPT/Dex group (indicated by a' vs b' in the bar graph in FIG. 4). Also, the average levels of G6pc mRNA levels were lower in AML-12 cells after treatment with 10 nM insulin, 8-CPT/Dec and a higher dose of Compounds CDE (10 nM insulin/8-CPT/Dex/300 ppb Compounds CDE group vs 10 nM insulin/8-CPT/Dex/150 ppb Compounds CDE group). However, there was no statistical difference between these two groups.

More dramatically, as shown in the inset bar graph, treatment with Compounds CDE at 300 ppb in combination with 100 nM insulin along with 8-CPT/Dex further significantly inhibited G6pc expression in AML-12 cells when compared to the 100 nM insulin and 8-CPT/Dex group (indicated by a" vs b" vs c" in the bar graph in FIG. 4). Furthermore, G6pc mRNA levels in AML-12 cells after treatments of 100 nM insulin, 8-CPT/Dex and 300 ppb of Compounds CDE were significantly lower than those in 100 nM insulin/8-CPT/Dex/150 ppb Compounds CDE group (see inset graph in FIG. 4).

Together, these results demonstrate that the combination of insulin and Compounds CDE was even more effective than insulin alone or Compounds CDE alone in inhibiting increased expression of G6pc due to 8-CPT/Dex treatment.

Glucose analysis was also performed on the cultured media of AML-12 cells after the above treatments. Unfortunately, the levels of glucose produced by AML-12 cells, even after 8-CPT/Dex stimulation, were too low to be detected by the sensitive fluorescence glucose assay (Abcam) (data not shown).

In summary, these results on AML-12 cells cultured under the above described culture conditions demonstrated that Compounds CDE can mimic insulin to inhibit G6pc expression under both normal and the in vitro model of pathological or diabetic condition (e.g., treatment of cells with 8-CPT/Dex), In addition, Compounds CDE can improve insulin action to inhibit G6pc expression in AML-12 cells cultured under simulated diabetic conditions. These results provide molecular evidence that Compounds CDE has the potential to inhibit excess glucose production in Type I and/or Type II Diabetics.

Upregulation of the Expression of Insr and Igf1r in AML-12 Cells after Treatment with the Compounds CDE Insulin receptor (Insr) and insulin-like growth factor 1 receptor 1 (Igf1r) are essential for insulin and IGF1 action to control G6pc expression, and subsequently glucose production in the liver. To examine whether the Compounds CDE combination can modulate insulin or IGF1 sensitivity in the liver cells in a receptor-dependent manner, the expression of the insulin and IGF1 receptors by QRT-PCR analysis was determined.

Figure 5A:
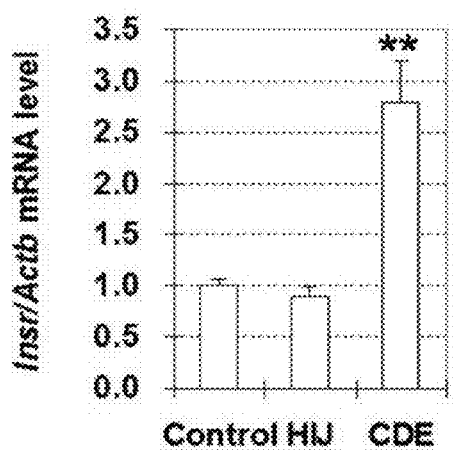
FIGS. 5A-5D show the effect of Compounds CDE and Compounds HIJ on relative mRNA expression levels of Insr and Igf1r genes in AML-12 liver cells.
Figure 5B:
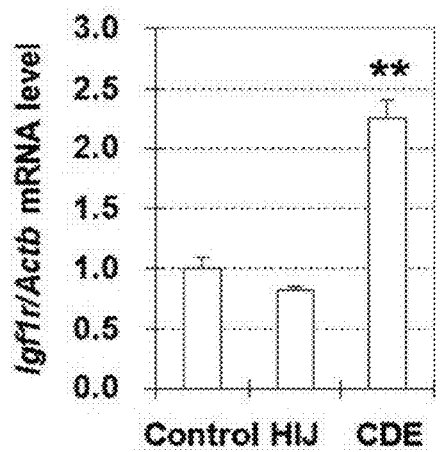

AML-12 cells were first treated with a water control (control, n=4), selenium Compounds CDE, and their sulfur analogs Compounds HIJ (n=4) in FBS-/Dex-containing but ITS-free media for 24 hours and then subjected to QRT-PCR analysis of Insr and Igf1r. As shown in FIG. 5A, Insr mRNA level was robustly increased by 2.78-fold following Compounds CDE treatment. Similarly, Igf1r expression was also significantly stimulated by the Compounds CDE by about a 2.2-fold increase (see FIG. 5B). However, sulfur analogs Compounds HIJ did not affect Insr and Igf1r expression in AML-12 cells (see FIGS. 5A and 5B).

To further validate that Compounds CDE can enhance Insr and Igf1r expression, AML-12 cells were treated with two doses of Compounds CDE in FBS-containing but ITS/Dex-free media for 24 hours. The cells were then retreated with the same doses of Compounds CDE in the presence or absence of 8-CPT/Dex in FBS/ITS/Dex-free media for 6 hours. In addition, these cells were treated with insulin for 6 hours to see if there was any difference between insulin and Compounds CDE in controlling Insr and Igf1r expression.

Figure 5C:
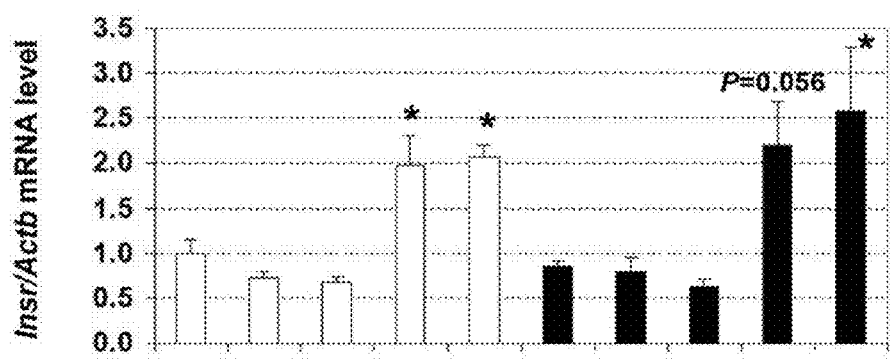
Figure 5D:
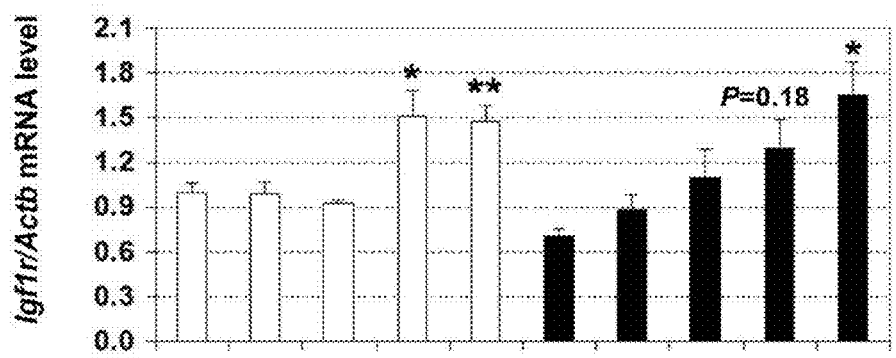

As shown in FIGS. 5C and 5D, treatments of Compounds CDE at both 150 ppb and 300 ppb doses, significantly enhanced Insr and Igf1r expression in AML-12 cells without cotreatments of 8-CPT/Dex, when compared to the control (i.e., 0 ppb CDE/no insulin and no 8-CPT/Dex group. However, Insulin alone did not increase Insr and Igf1r expression in AML-12 cells (see FIGS. 5B and 5C). Similarly, treatments of Compounds CDE at the dose of 300 ppb, but not insulin, also significantly enhanced Insr and Igf1r expression in AML-12 cells cotreated with 8-CPT/Dex (see black bars in FIGS. 5C and 5D).

These results demonstrate that Compounds CDE can stimulate Insr and Igf1r expression in AML-12 cells under the tested conditions. In addition, these data show that there exists a difference between insulin and Compounds CDE action in regulating gene expression in AML-12 cells. Also, the results suggest that Compounds CDE may be useful for treatment of Type I and Type II diabetics by improving insulin sensitivity.

Together, the above gene expression studies (FIGS. 2A-2B, 3, 4) demonstrate that Compounds CDE, but not the individual compounds or their sulfur analogs, can mimic insulin to significantly attenuate G6pc expression, thereby representing a novel way to reduce hepatic glucose output. These data also provide molecular evidence that Compounds CDE can act in a similar way as insulin does in the inhibition of G6pc expression in mouse liver cells even in the presence of a stimulant of glucose production, such as 8-CPT/Dex (FIGS. 3-4).

In addition, Compounds CDE in combination also improves insulin action to further inhibit G6pc expression in 8-CPT/Dex-stimulated AML-12 cells (FIG. 4). Compounds CDE in combination can stimulate Insr and Igf1r expression (FIGS. 5A-5D) that also contributes to reduced G6pc expression for glucose production in the liver together with enhanced insulin/Igf1 sensitivity and glucose trafficking. Moreover, Compounds CDE in combination did not have toxic effects on the viability of liver cells (FIG. 1). In short, these results demonstrate that Compounds CDE in combination mimic insulin to inhibit G6pc expression and also improves insulin action in the process, likely through the stimulation of Insr and/or Igf1r expression, in mouse liver AML-12 cells with no toxic effects on cell survival or viability.

Example 5

Compounds CDE Target Foxo3 and Foxo4 Phosphorylation in AML-12 Cells

The Forkhead transcription factor family subclass 0 (FOXO) plays a critical role in metabolism, gluconeogenesis, and insulin sensitivity in the liver. Intracellular activity of FOXO genes is tightly regulated by post-translational modification. In particular, phosphorylation of FOXOs excludes it from the nucleus, thereby blocking its access to its target genes. In insulin-resistant or diabetic individuals, there is no signal to exclude FOXOs from the nucleus, so it remains present in the nucleus and stimulates the transcription of G6pc. Increased expression of G6pc drives gluconeogenesis, leading to hyperglycemia. Insulin-like growth factors (IGFs) also can modulate insulin action to control FOXO-mediated G6pc expression for glucose production in the liver.

As described earlier, AML-12 liver cells demonstrated that Compounds CDE in combination can mimic insulin action to inhibit G6pc expression and can improve insulin action in the process. Since FOXOs are major signaling molecules for gluconeogenesis and insulin sensitivity in the liver, the question of whether Compounds CDE, like insulin, will target FOXOs and other related signaling molecules in AML-12 cells was examined Compounds CDE Target Foxo3 and Foxo4 Phosphorylation in AML12 Cells Cultured in Serum-Containing Media To determine if the combination of Compounds CDE can regulate FOXO phosphorylation in the liver, AML-12 cells were treated with control, and 150 ppb of selenium Compounds CDE, and their sulfur analogs, 150 ppb of Compounds HIJ, in serum- and Dex-containing media but without ITS for 6 hours. Treated cells were subjected to Western blot analysis. Quantitative data of protein expression in Western blots are presented as mean±SEM of 3 samples. Different letters in the bar graphs means a significant difference between those two groups (P<0.05).

Figure 6A:
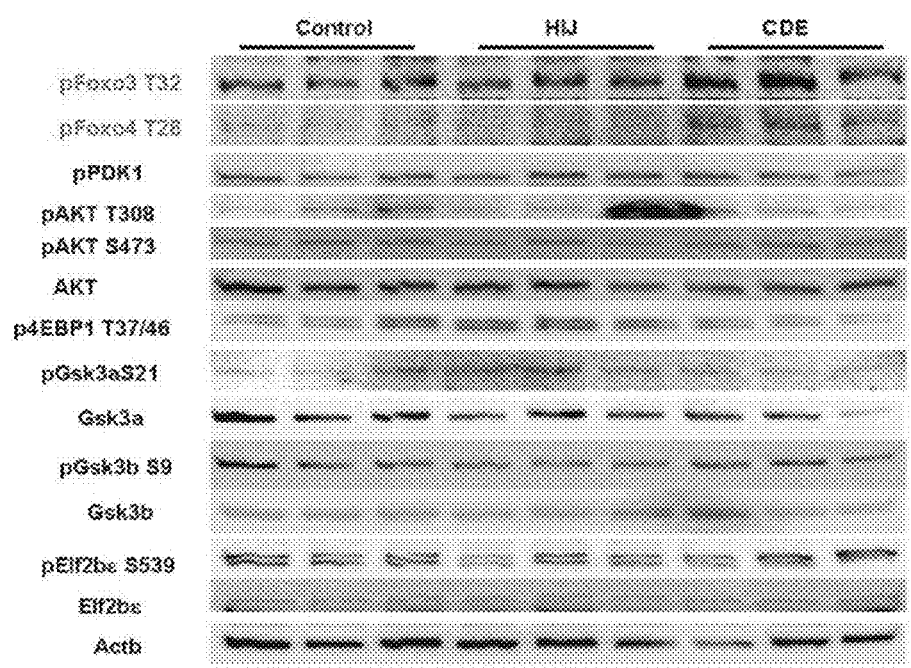
FIGS. 6A-6C show the effect of Compounds CDE and Compounds HIJ on protein levels of phosphorylated Foxo3 at threonine 32 (pFoxo3T32) and phosphorylated Foxo4 at threonine 28 (pFoxo4T28) in AML-12 cells cultured in serum-containing media.
Figure 6B:
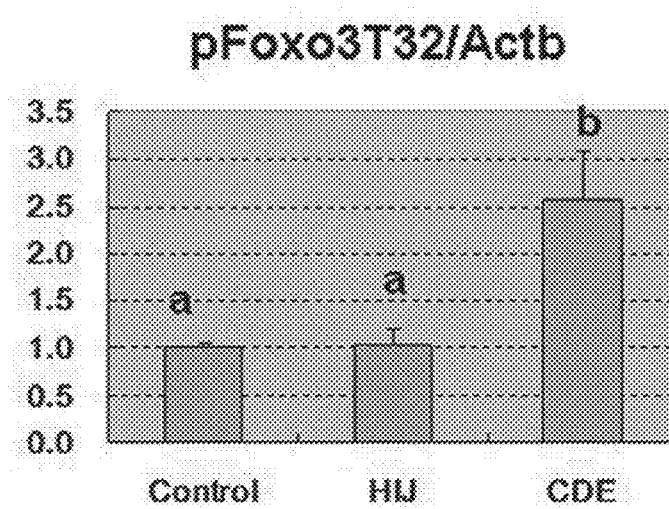
Figure 6C:
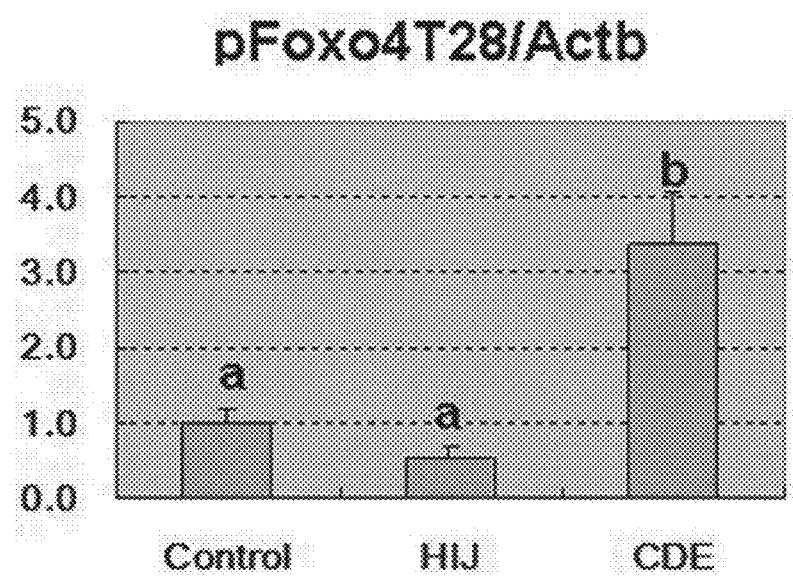

FIG. 6A shows protein expression of various signaling molecules including phosphorylated Foxo3T32 (Threonine 32; pFoxo3T32), phosphorylated Foxo T28 (Threonine 28; pFoxo4T28), phosphorylated PDK1 (pPDK1), phosphorylated AKT T308 (Threonine 308; pAKTT308), phosphorylated AKT 5473 (Serine 473; pAKTS473), AKT, phosphorylated Gsk3a S21 (Serine 21; pGsk3bS21), phosphorylated Gsk3b S9 (Serine 9; pGsk3bS9), Gsk3a, Gsk3b, phosphorylated 4EBP1 T37/46 (Threonine 37 and Threonine 46; p4EBP1T37T46), phosphorylated Elf2bεS539 (Serine 530; pElf2bεS530) and Elf2bε in AML-12 cells after treatment with water, and 150 ppb of Compounds HIJ and 150 ppb of Compounds CDE diluted in serum- and Dex-containing media (but without ITS) for 6 hours. It was found that phosphorylated forms of Foxo3 (e.g., pFoxo3 at Threonine 32, pFoxo3T32) and Foxo4 (e.g., pFoxo4 at Threonine 28, pFoxo4T28) proteins were found to be visibly elevated in AML-12 cells after treatment with Compounds CDE, but not Compounds HIJ, for 6 hours (FIG. 6A). Quantitative analysis showed there was approximately a 2.5-fold increase of pFoxo3T32 and about a 3.2-fold increase of pFoxo4T28 in Compounds CDE-treated AML-12 cells (FIGS. 6B and 6C). We also tested several phosphorylated Foxo1 (pFoxo1) antibodies, but failed to detect a specific pFoxo1 protein band on Western blots by these antibodies (data not shown). The results suggest that pFoxo1 expression in AML-12 cells is likely very low.

QRT-PCR analysis of Foxo1, Foxo3, and Foxo4 protein levels in AML-12 cells after the same treatment described above were performed. There was no observation of any significant change of Foxo1, 3, or 4 mRNA expression (data not shown) and the observed increase of phosphorylated Foxo3 and Foxo4 (see FIGS. 6A-6C) is not due to the potential increase of Foxo3/4 protein expression in AML-12 cells by Compounds CDE. In fact, total Foxo3 and Foxo4 protein levels were not affected by Compounds CDE in AML-12 cells cultured in serum-free condition (see FIG. 7A).

In addition, individual Compound C, Compound D and Compound E each at 150 ppb dose in AML-12 cells were tested to determine the effect on Foxo3/4 phosphorylation at the same culture condition (in serum-containing media) for 6 hours and 24 hours. No change of pFoxo3T32 and pFoxo4T28 protein levels after treatment with individual Compound C, Compound D or Compound E treatment was observed (data not shown), indicating that there exists a synergistic effect among Compound C, Compound D and Compound E in combination which leads to phosphorylation of Foxo3 and Foxo4 in AML-12 cells.

Together, these results demonstrate that Compounds CDE, but not the individual compounds or their sulfur analogs, can enhance Foxo3 and Foxo4 phosphorylation in AML-12 cells when cultured in serum-containing media. As phosphorylation of FOXOs results in nuclear exclusion of these transcription factors, these results suggest that Compounds CDE will function as Foxo3 and Foxo4 inactivators in AML-12 liver cells.

Since phosphatidylinositol 3-kinase (PI3K)/phosphoinositide-dependent protein kinase 1 (PDK1)/Protein Kinase B (AKT) is the major signaling pathway upstream of FOXOs for the insulin-mediated control of glucose production in the liver, it was assessed whether there was any change in the levels of phosphorylated PDK1 (pPDK1) and AKT (pAKT) in these compound-treated AML-12 cells. Surprisingly at the tested 6 hours of treatment, Compounds CDE did not affect the phosphorylation of PDK1 and AKT, or total AKT levels (FIG. 6A). This could be due to the potential transient effects of Compounds CDE on the activation of PDK1 and AKT which occurs in AML-12 cells at earlier time points (before the tested 6 hour time point examined).

In addition, levels of two other downstream signaling molecules, phosphorylated GSk3a and GSK3b, which are directly controlled by AKT, were not observed to have any change in their protein levels (FIG. 6A). The levels of phosphorylated 4EBP1 (a downstream molecular target of AKT/mTOR signaling) and pelf2Bϵ S539 (a downstream molecular target of Gsk3) that are key for insulin-driven protein synthesis or translation were also not affected (see FIG. 6A). These results provide additional direct molecular evidence that Compounds CDE did not have a toxic effect on AML-12 cell proliferation or survival as described earlier (FIG. 1).

Together, these results suggest that Compounds CDE did not affect several AKT-direct or -indirect downstream signaling molecules such as Gsk3a, Gsk3b, p4EBP1 and pElf2bϵ 5539, except the above described Foxo3 and Foxo4 in AML-12 cells in the presence of serum in culture media. In other words, Compounds CDE can selectively inactivate FOXOs by enhancing their phosphorylation in AML-12 liver cells.

Compounds CDE Target Foxo3/4 Phosphorylation in AML-12 Cells Cultured in Serum-Free Conditions As mentioned earlier, AML-12 cells can be cultured in serum-free media for a short time period of time (i.e., 6 hours) without obvious morphological defects (data not shown). Thus, the protein levels of phosphorylated Foxo3 and Foxo4 proteins in AML-12 cells cultured under serum-free conditions was examined.

In brief, AML-12 cells were treated with control (water), Compounds CDE (150 ppb of selenium of each compound), Compounds CE (150 ppb of selenium of each compound) or Compounds DE (150 ppb of selenium of each compound) in serum-free, ITS-free, and Dex-free media for 6 hours and subjected to Western blot analysis and quantitative analysis. Quantitative data were normalized by Actb protein level and are presented as mean±SEM of 3 samples. Different letters in the bar graphs of FIGS. 7B and 7C means a significant difference between those two groups (P<0.05).

Figure 7A:
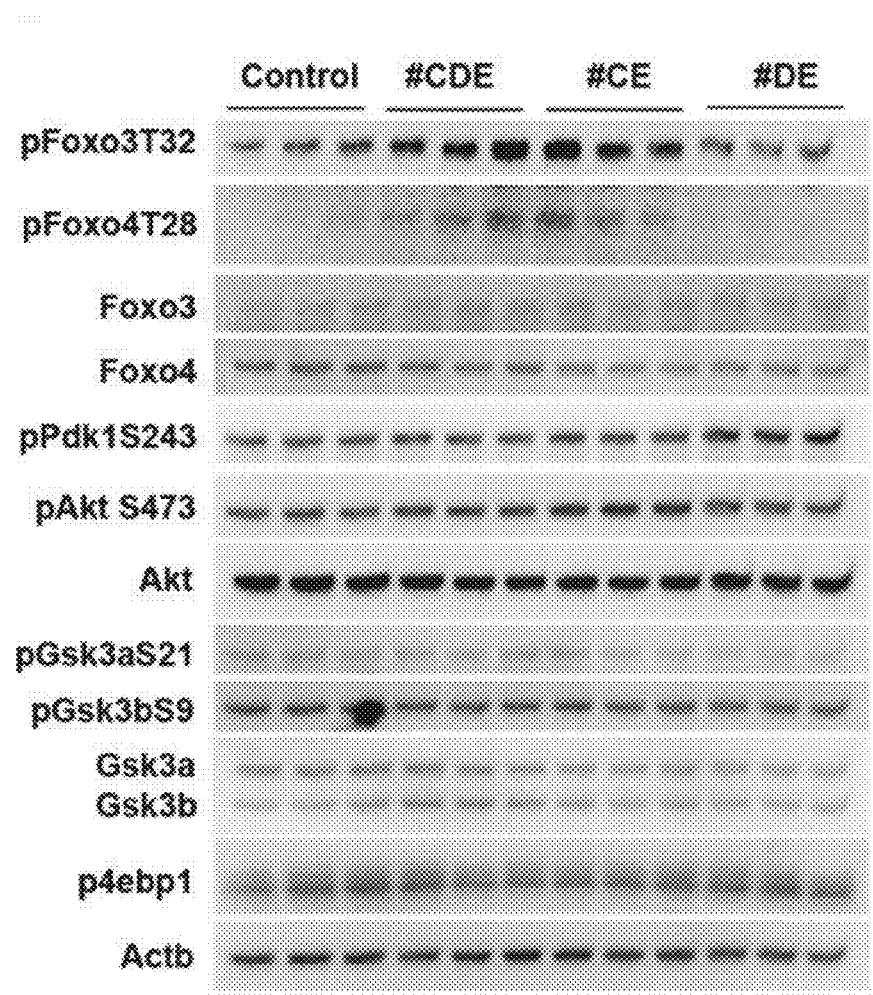
FIGS. 7A-7C show the effect of Compounds CDE, Compounds CE, and Compounds DE on protein levels of pFoxo3T32 and pFoxo4T28 in AML-12 cells cultured in serum-free media.

As shown in FIG. 7A, the phosphorylated protein levels of Foxo3 (pFoxo3 at Threonine 32) and Foxo4 (pFoxo4 at Threonine 28) were found to be elevated in AML-12 cells after treatment with Compounds CDE and Compounds CE, but not Compounds DE, for 6 hours in serum-free medium. There was no obvious change of total Foxo3 and Foxo4 protein levels after the treatments with the selenium compounds (FIG. 7A). No specific band of pFoxo1 was detected using several specific pFoxo1 antibodies on these protein samples (data not shown).

Quantitative analysis showed that there was approximately a 1.8-fold increase of pFoxo3T32 (FIG. 7B) and about a 6-fold increase of pFoxo4T28 (FIG. 7C) levels in Compounds CDE-treated and Compounds CE-treated AML-12 cells. All other tested molecules such as pPdk1, pAkt, pGsk3a, pGsk3b, and p4ebp1 were not obviously altered by Compounds CDE (see FIG. 7A). The above results obtained from AML-12 cells cultured in serum-free condition by Compounds CDE are consistent with the findings from AML-12 cells cultured in serum-containing media (FIGS. 6A-6C). The enhancement of Foxo3 and Foxo4 phosphorylation by Compounds CDE in AML-12 cells is totally independent of FBS, growth factors or insulin, since insulin or FBS were not added to the culture medium of the cells in this experiment. In other words, Compounds CDE can bypass insulin or growth factors to inactivate Foxo3 and Foxo4 in liver cells.

Figure 7B:
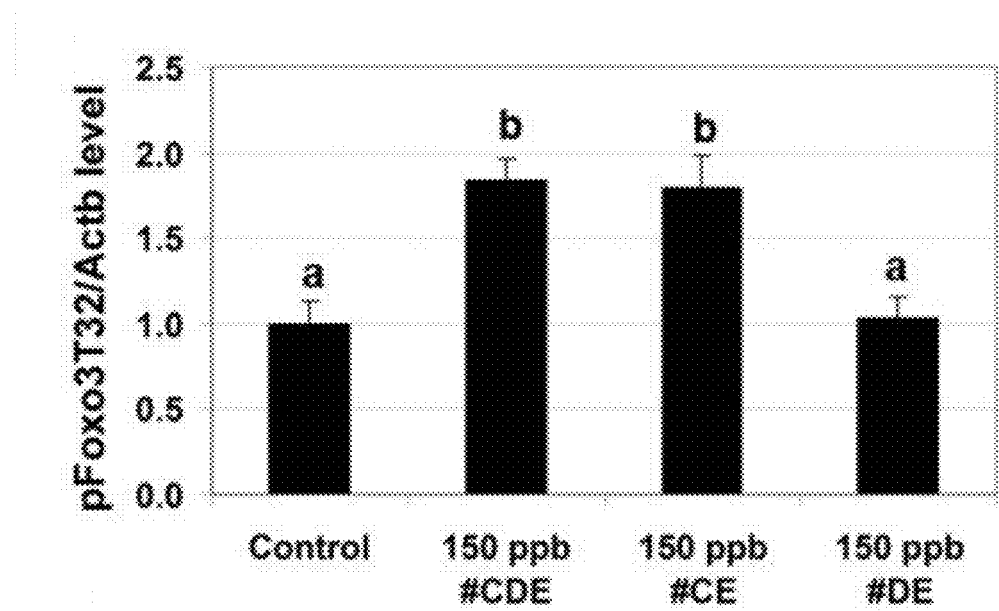
Figure 7C:
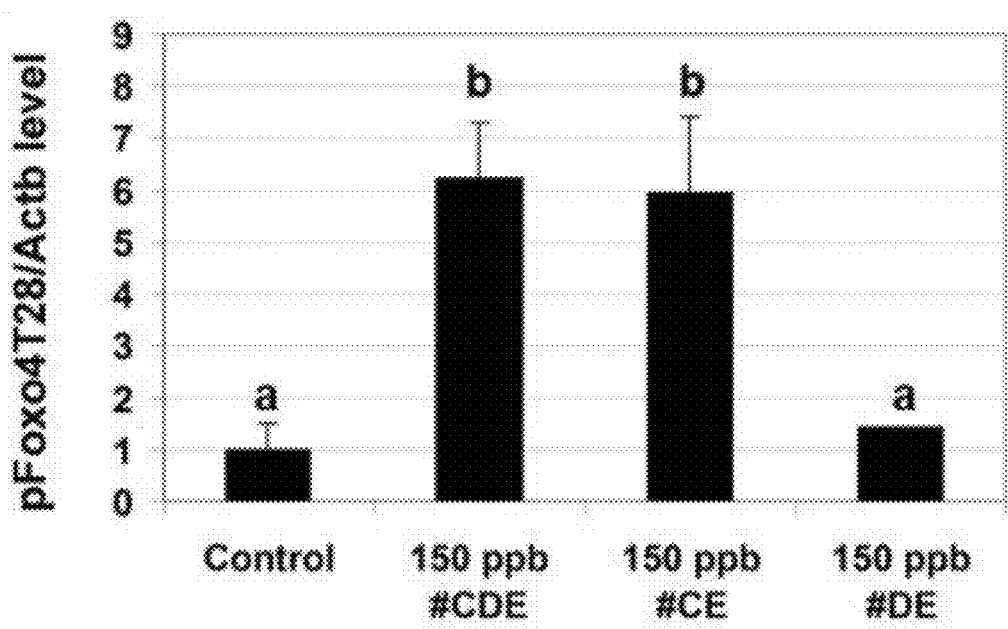

In short, these results demonstrate that Compounds CDE can specifically target Foxo3 and Foxo4 phosphorylation in AML-12 cells cultured in both serum-containing (FIGS. 6A-6C) and serum-free media (FIGS. 7A-7C). Therefore, it can be concluded from these studies that Compound CDE are novel FOXO inactivators and the inactivation of these FOXO molecules by Compounds CDE is insulin-, FBS- and other growth factor-independent in mouse liver cells.

Figure 8:
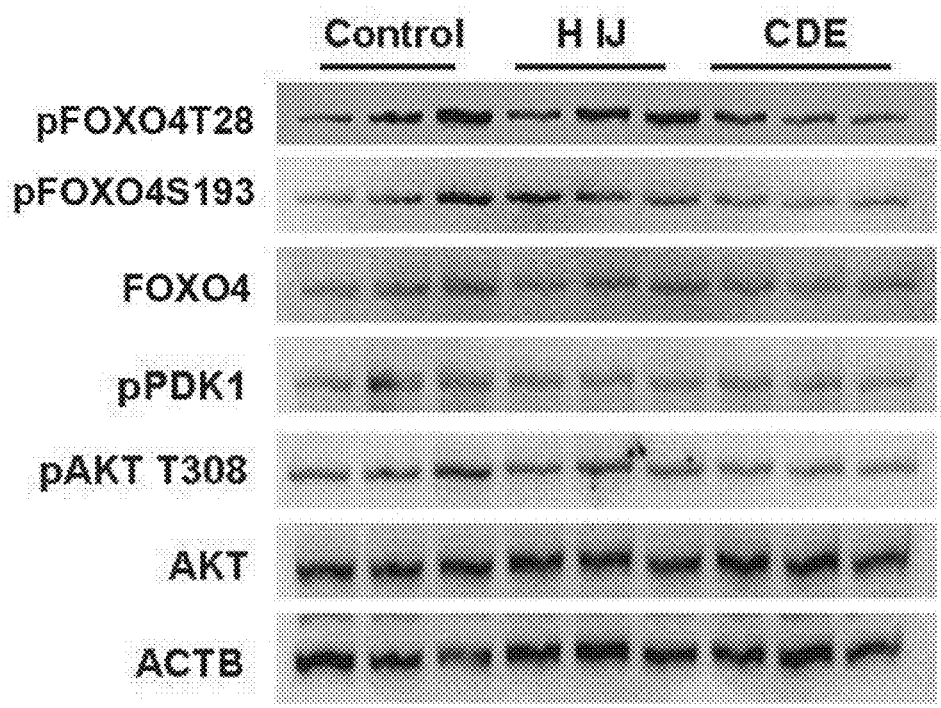
FIG. 8 is a Western blot showing the effect of a control or 150 ppb of Compounds CDE and 150 ppb of Compounds HIJ on protein levels of pFOXO4T28, pFOXO4S193 and other signaling molecules in human IMR-32 neuronal cells.

To test if the observed increase of FOXO4 phosphorylation in the AML-12 liver cells is a general effect of the Compounds CDE combination in mammalian cells, we examined pFOXO4 levels in a non-liver IMR-32 neuronal cell line in that tests were performed at the same time and under the same experimental conditions as the AML-12 liver cells. As shown in FIG. 8, increased FOXO4 phosphorylation was not observed in Compounds CDE-treated IMR-32 neuronal cells. The protein levels of phosphorylated FOXO1 and FOXO3 were also examined and found that phosphorylated FOXO3 were barely detected and phosphorylated FOXO1 were undetected in IMR-32 cells by their specific antibodies (data not shown). Regardless, the absence of increased phosphorylation of FOXO4 in IMR-32 cells by Compounds CDE (FIG. 8) indicates that Compounds CDE in combination likely have no toxic effects on neuronal cells. Thus, we can conclude that enhanced FOXO phosphorylation by Compounds CDE is likely liver-cell specific.

Taken together, these results suggest that the Compounds CDE, but not the individual compounds or their sulfur analogs, will function as novel liver cell-specific FOXO inactivators and that the inactivation of these FOXO molecules in mouse liver cells by Compounds CDE is independent of insulin and any other growth factors.

Previous data described herein demonstrated that Compounds CDE can mimic insulin action to inhibit G6pc expression and improve insulin action to further inhibit G6PC expression in AML-12 cells (FIGS. 3-4). The latter (FIG. 4), as discussed earlier, could be also attributed to enhanced Insr and Igf1r expression (FIGS. 5A-5D). All these events are likely due to the insulin/growth factor/FBS-independent inactivation of Foxo3 and Foxo4 by Compounds CDE (FIGS. 6A-6B, 7A-7C), since G6pc is a well-known FOXO target gene in human liver while Insr and Igf1r are two potential Foxo3/4 target genes due to the presence of many Foxo binding motifs in their gene promoters (data not shown) Enhanced Insr and Igf1r expression by Compounds CDE (FIGS. 5A-5D) will further enhance the action of insulin or improve the insulin sensitivity to further stimulate Foxo3/4 phosphorylation to inhibit G6pc expression.

Regardless, these results suggest that the combination of Compounds CDE can specifically act as a potent insulin-independent or other growth factor-independent FOXO inactivator in AML-12 liver cells to reduce G6pc expression and likely lower hepatic glucose output. In addition, administration of Compounds CDE likely will lessen the physiological consequences of a liver cell becoming insulin-resistant, in the context of controlling G6pc expression to lower hepatic glucose output. Bypassing insulin to enhance Foxo phosphorylation by Compounds CDE, while still being able to control glucose homeostasis through the regulation of FOXO-mediated G6pc expression, opens up many therapeutic possibilities for the treatment of diabetes in general. As a consequence, diabetes treatment becomes less dependent on the unilateral administration of exogenous insulin or, the correct functioning of insulin receptors.

Example 6

The Compounds CDE in Combination Improve Insulin Action in the Inhibition of G6pc Expression and Glucose Production and Bypass Insulin to Regulate Pdk1/Akt/Foxo1/3/4 Signaling in Primary Mouse Hepatocytes without being Toxic to Cells A combination of three synthetic selenoorganic compounds, Compounds CDE, were tested in combination in cell culture of primary mouse hepatocytes for effects on glucose production, G6pc expression and Foxo1/3/4 phosphorylation.

Materials and Methods
Primary Mouse Hepatocyte Isolation and Compounds

Primary mouse hepatocytes were purchased from Triangle Research Labs, LLC (Research Triangle Park, North Carolina). These primary mouse hepatocytes were isolated from adult healthy normal C57BL6 mice, cultured on collagen-coated 12-well or 24 well-plates for 24 hours in Triangle Research Labs (TRL) and then shipped to our laboratory for the experiments.

Compound C (5'-Methylselenoadenosine), D (Se-Adenosyl-L-homocysteine) and E (Gamma-glutamyl-methyl-seleno-cysteine), were synthesized in the Chemistry Laboratory of Alltech, Inc. The purities of all tested compounds were verified to be ≥99%, as determined by Mass-Spectrometry.

Cell Culture and Treatments

Primary mouse hepatocytes, grown on 12- or 24-well collagen-coated culture plates, were received from Triangle Research Lab (TRL) on day 3 after the fresh isolation of hepatocytes from mice and cultured in hepatocyte maintenance medium (TRL) in a 5% $CO_2$ incubator at 37° C. to allow the hepatocytes to acclimate for 8 hours or overnight, according the TRL recommended procedure (Research Triangle Park, NC).

The overnight-acclimated hepatocytes were washed twice with PBS (to remove any residual FBS and other additives in the TRL hepatocyte maintenance medium, pretreated with control (water) or selenium Compounds CDE (150 or 300 ppb of each selenium compound) in DMEM/F12 media supplemented with 10% fetal bovine serum (FBS) for 24 hr. These cells were then washed twice with PBS and incubated with the same dose of selenium Compounds CDE (150 or 300 ppb) in the presence or absence of insulin (10 or 100 nM, Sigma), 0.1 mM 8-CPT (Sigma) or 0.5 µM Dex (Sigma) in serum-free and glucose-free DMEM media (Invitrogen) supplemented with 20 mM lactose (Sigma) and 2 mM pyruvate (Sigma) and 15 mM HEPES (Sigma) for another 6 hours. After treatments, cell media were collected and subjected to glucose assay and toxicological studies of lactate dehydrogenase (LDH) and cells were collected for RNA and protein analysis.

For the studies of Compounds CDE on primary mouse hepatocytes under totally serum-free culture conditions, hepatocytes were acclimated in hepatocyte maintenance medium (TRL) for 8 hours, washed twice with PBS (to remove any residual FBS and other additives in the culture dish) and then starved in serum-free DMEM/F12 media overnight. Some of these serum-starved hepatocytes were treated with control (water), selenium compounds (150 or 300 ppb of each compound) in the presence or absence of insulin (10 or 100 nM), 0.1 mM 8-CPT (Sigma) or 0.5 µM Dex (Sigma) in serum-free and glucose/phenol red-free DMEM media supplemented with 20 mM lactose and 2 mM pyruvate and 15 mM HEPES for 6 hours. After 6 hours treatment, culture media were collected for glucose analysis and toxicological studies monitoring LDH activity and cultured cells were isolated for protein analysis. In addition, some serum-starved hepatocytes were treated with Compounds CDE (300 ppb of each compound) in plain DMEM/F12 media for 0, 5, 30, 60, 120 and 180 min and cells were collected for the time-course protein analysis of various signaling molecules.

RNA Isolation and Real-Time PCR Analysis

Total RNA from these cells was isolated using Trizol (Invitrogen) according to the Manufacturer's protocol and then incubated with DNase I to remove any potential contaminated genomic DNA. Then RNA samples were subjected to real-time PCR analysis using the Applied-Bioscience's RT kit and predesigned Taqman probes (Invitrogen), as described previously (Lan et al EMBO J 2003). Three to four samples were analyzed in each treatment group. Data were normalized by Actb mRNA level in each sample and are presented as mean±SEM of 3-4 samples.

Protein Preparation and Western Blot Analysis

After the above described treatments, primary mouse hepatocytes were rinsed with ice-cold PBS and lysed in the ice-cold RIPA buffer containing complete proteinase and phosphatase inhibitors (Thermo-Fisher Scientific, Waltham, Mass.) on ice for 30 min Cell lysates were collected using a cell scraper and transfer pipette and then centrifuged at 12000×g for 30 min at 4° C. to remove the DNA pellet and obtain the protein extract. Protein levels in the supernatant of these cell lysates were determined using the Pierce Micro-BCA protein assay kit (Thermo Scientific-Piece Biotechnology, Rockford, Ill.) according to the manufacturer's protocol.

For Western blot analysis, five micrograms of total proteins from control- and compound(s)-treated cells were subjected to SDS-PAGE gel separation and then transferred to PVDF membranes, as described previously (Reddy et al. 2008 Science). Membranes were blocked in a phosphate-buffered saline (PBS) containing 5% (w/v) of bovine serum albumin (Sigma, St. Louis, Mo.) and incubated with specific primary antibodies followed by the incubation with HRP-conjugated anti-mouse or anti-rabbit secondary antibodies (1:5000 dilution, Cell Signaling Inc.). All primary antibodies except Actb (Li-COR, Lincoln, Nebr.) were purchased from Cell Signaling Inc. Positive signals on the membrane blots were detected using the Amersham's enhanced chemiluminescence Western Blotting Prime Detection reagents (GE Healthcare Lifescience, Pittsburgh, Pa.). Images of these luminescence signals on the membrane blots were captured using the LI-COR Odyssey Fc Image system (Lincoln, Nebr.). The same membrane blot was stripped and re-blotted with another antibody as described in the GE WB ECL-prime-detection protocol (GE healthcare Lifescience, Pittsburgh, Pa.). Protein band densities in the Western blots were determined using the NIH ImageJ software and then normalized by Actb level in each sample. Data are presented as mean±SEM of three samples per each group.

Analysis of Glucose Production

Cell culture media from the above described treatments were collected and centrifuged at 300×g for 5 minutes to remove any potential dislodged hepatocytes and subjected to glucose analysis using a colormetric glucose assay kit (Abcam) according to the manufacturer protocol. The absorbance at OD570 nm in the samples and various concentrations of glucose standards were determined by the Bio-Tek microplate reader, and glucose concentration in the medium of each sample was obtained from the glucose standard curve, and then normalized by its protein level in attached cells which were determined using the Pierce Micro-BCA protein assay kit (Thermo Scientific-Piece Biotechnology, Rockford, Ill.) according to the manufacturer's protocol. Glucose levels in each treatment group were divided by the mean level in control group (without the treatments of Compounds CDE, insulin, 8-CPT and Dex) to obtain the relative glucose level. Data are presented as Mean±SEM of 3-4 samples.

Toxicological Studies by Examining LDH Level in Culture Media

Similar to the above glucose assay, cell culture media from the above described treatments were collected and centrifuged at 300×g for 5 minutes to remove any potential dislodged hepatocytes and subjected to LDH analysis using a colormetric glucose assay kit (Abcam) according to the manufacturer protocol. In brief, the absorbance at OD450 nm in LDH standards and the culture medium samples after incubation with LDH substrates for every two minutes up to 40 minutes were determined by the Bio-Tek microplate reader. LDH concentration in the medium of each sample was obtained by subtracting the OD450 reading within the linear range of absorbance followed by using the LDH standard curve, according to the manufacturer protocol. The obtained LDH level in the medium of each sample was then normalized by its protein level in attached cells. The LDH levels in each treatment group were further normalized by the mean value of control group (without the treatments of Compounds CDE, insulin, 8-CPT and Dex) to obtain the relative LDH level in each group. Data are presented as Mean±SEM of 3-4 samples.

Statistical Analysis

If applicable, a Student's t-test was performed to determine the statistical difference between two groups. P-value less than 0.05 was considered significant.

Results and Discussion

Compounds CDE in Combination Inhibit Glucose Production and G6pc Expression in Primary Mouse Hepatocytes Previous studies described herein in AML-12 cells demonstrate that Compounds CDE can mimic insulin to inhibit G6pc expression (FIGS. 3-4) but have no toxic effects on AML-12 cell viability (FIG. 1). However, whether Compounds CDE can control glucose production in AML-12 cells was not established, as the levels of glucose in culture media produced by AML-12 cells were too low to be detected by a sensitive fluorescence glucose assay kit (Abcam, data not shown). Thus, primary mouse hepatocytes were used to investigate if Compounds CDE can mimic insulin to inhibit glucose production and to further confirm the inhibited effects of Compounds CDE on G6pc expression but no toxic effects on cell survival observed in AML-12 cells.

Figure 9A:
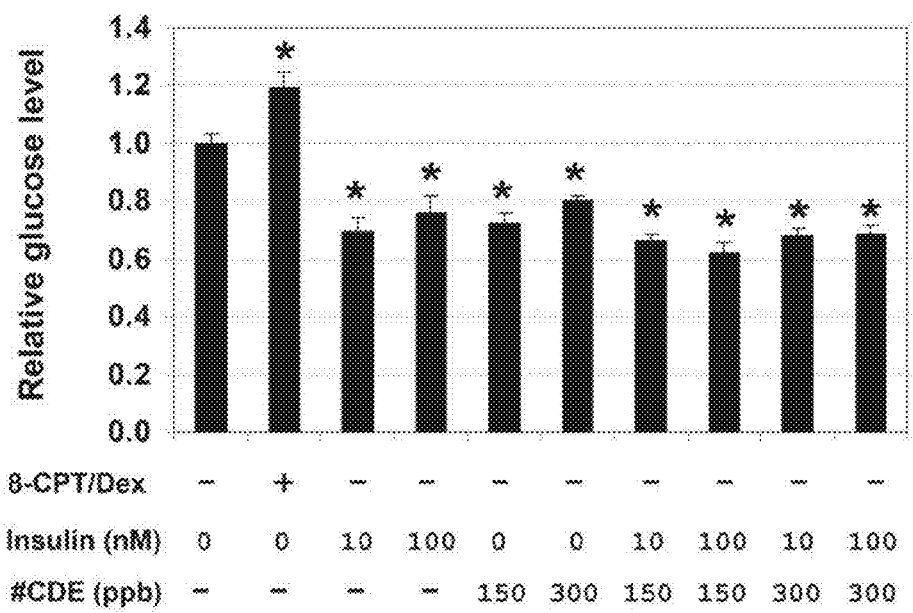
FIGS. 9A-9C show the effect of Compounds CDE on glucose production, G6pc mRNA expression, and extracellular lactate dehydrogenase (LDH) activity in primary mouse hepatocytes.
Figure 9B:
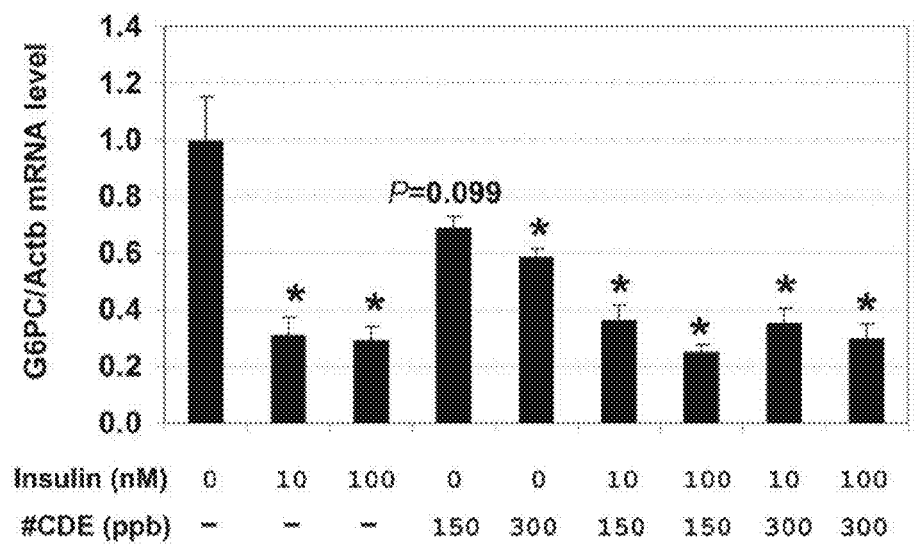
Figure 9C:
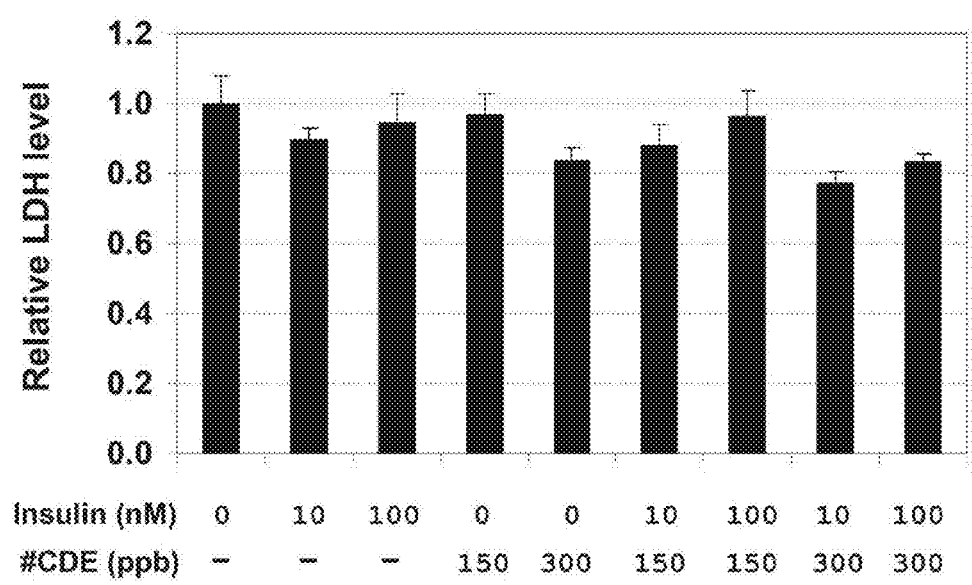

Similar to the studies on AML-12 cells, primary mouse hepatocytes were pretreated with a control (water) or 150 ppb and 300 ppb doses of selenium Compounds CDE in serum-containing DMEM/F12 media for 24 hours. This treatment was followed by retreatments with these selenium compounds in the presence or absence of insulin (10 and 100 nM) or insulin alone for 6 hours. In addition a cell-permeable cAMP, 8-CPT and Dex were also added to some control-pretreated hepatocytes for 6 hours to validate whether the primary mouse hepatocytes were functioning in response to these well-known stimuli of glucose production in liver cells. After the above described treatments, cell culture media were collected for glucose assay and toxicological analysis (by measuring LDH levels). Attached cells were subjected to protein analysis to determine protein levels in each well reflecting the total cells in the sample. Then glucose levels obtained in culture medium were normalized by protein levels in each sample. Data are presented as mean±SEM of 4 samples. In FIGS. 9A-9B, the * P<0.05 vs vehicle treatment group (the first bar in the graphs). In FIG. 9C, no significant increase in all treatment groups vs control treatment group (the first bar in the graph).

As shown in FIG. 9A, treatments of 8-CPT/Dex caused a significant increase of glucose production in primary hepatocytes, indicating that these primary hepatocytes were biologically functional even after having been processed, shipped and cultured for 5 days since their initial isolation from mouse livers. To further support this finding, treatment with insulin alone at 10 nM and 100 nM doses caused a significant decrease of glucose production (about a 25-30% decrease when compared to the water-treated control group; see FIG. 9A).

More importantly, treatments with Compounds CDE at both doses (150 ppb and 300 ppb) significantly reduced the glucose production at about a 20-28% decrease when compared to the water-treated control group (see FIG. 9A). Cotreatments of Compound CDE with insulin also significantly inhibited glucose production by about 32-38% decrease in tested treatments when compared to control group (see FIG. 9A).

It should be emphasized here that the extent of the decrease of glucose production by Compounds CDE at both test doses were comparable to insulin (10 or 100 nM), suggesting that Compounds CDE at the tested doses are as effective as insulin at the concentration of 100 nM to inhibit glucose production. Our data also indicate that the maximum attainable decrease of glucose production by insulin, Compounds CDE or both is about 20-38% in these hepatocytes. Regardless, our data demonstrate that Compounds CDE can mimic insulin to inhibit glucose production in primary mouse hepatocytes.

G6pc is essential for glucose production in the liver. Thus we examined G6pc expression in the same batch of hepatocytes after the same treatments. In brief, a duplicate set of primary hepatocytes were pretreated with control (water) or selenium Compounds CDE at the doses of 150 and 300 ppb in serum-containing DMEM/F12 media, followed by retreatments with these selenium compounds in the presence or absence of insulin (10 and 100 nM) for 6 hours. After these treatments, hepatocytes were collected and subject to RNA isolation followed by QRT-PCR analysis of G6pc and Actb.

As shown in FIG. 9B, insulin alone or in the presence of both doses of Compounds CDE significantly inhibited G6pc expression. Compounds CDE at 150 ppb also caused a decrease of G6pc expression (about 31% decrease, FIG. 9B), even though it was not statistically significant likely due to the limited number of samples. However, a significant decrease (42% decrease) of G6pc mRNA levels was observed in hepatocytes after treatment with Compounds CDE alone at 300 ppb (FIG. 9B). These results demonstrate that Compounds CDE also can mimic insulin, albeit slightly less efficiently than insulin at the dose of 100 nM, to inhibit G6pc expression in primary mouse hepatocytes. These findings are consistent with the inhibition of G6pc expression in AML12 cells (FIG. 3) and attenuated glucose production by Compounds CDE in primary mouse hepatocytes described above (FIG. 9A).

Lactate Dehydrogenase (LDH) is widely used in drug development for studying of compound toxicity in liver cells. An increase of LDH level in culture media (after normalized by protein levels in cultured cells) by compound treatments suggests that the compound will be toxic to liver cells due to cell breakdown or cell membrane leakage to release cytosolic LDH into culture medium. To investigate if Compounds CDE is toxic to primary mouse hepatocytes and whether the observed decrease of glucose production and G6pc expression by Compounds CDE (FIGS. 9A and 9B) was due to toxicity, LDH levels in the media of primary mouse hepatocytes after treatment with Compounds CDE as described in the above glucose assay were examined.

In brief, primary mouse hepatocytes were pretreated with control (water) or selenium Compounds CDE at the doses of 150 and 300 ppb in serum-containing DMEM/F12 media, followed by retreatment with these selenium compounds in the presence or absence of insulin (10 and 100 nM) for 6 hours. Cell culture media were then collected for toxicological analysis of LDH and attached cells were subjected to protein analysis to determine protein levels in each. The LDH level obtained in culture medium was normalized by its protein level in each sample.

As shown in FIG. 9C, treatment with Compounds CDE, insulin or both did not cause a significant increase of LDH levels in the media. Instead, LDH levels appear to be slightly decreased in hepatocytes after treatment with Compounds CDE at the dose of 300 ppb either in the presence or absence of insulin, indicating that Compounds CDE at a higher dose may even impact a protective effect against cell breakdown.

As such, these results demonstrate that Compounds CDE are not toxic to primary mouse hepatocytes, which is consistent with the non-toxic effects of Compounds CDE on the viability of AML-12 cells (FIG. 1). In addition, these results also exclude the possibility that the above observed decrease of glucose production and G6pc expression (FIGS. 9A and 9B) is caused by less healthy hepatocytes in primary mouse hepatocytes after treatment with Compounds CDE.

Together, the above studies demonstrate that Compounds CDE can mimic insulin to inhibit G6pc expression and, more importantly, glucose production in primary mouse hepatocytes without being toxic to the cells. These results are consistent with insulin-independent inhibition of G6pc expression and no toxicity to cell survival observed in stable mouse liver AML-12 cells (FIG. 1 and FIG. 3).

Inhibition of Glucose Production and G6pc Expression and Improvement of Insulin Action in these Processes in Primary Mouse Hepatocytes Under Simulated Diabetic Conditions (Simulated by Both 8-CPT and Dex) by Compounds CDE The studies described herein demonstrate that Compounds CDE in combination can mimic insulin to inhibit G6pc expression and improve insulin action in AML-12 cells under the stimulation of 8-CPT/Dex (FIG. 4). To further investigate the effects of Compounds CDE, glucose production and G6pc mRNA expression were examined in primary mouse hepatocytes cotreated with cAMP and Dex, two well-known stimuli of glucose production and G6pc expression in the liver.

Figure 10A:
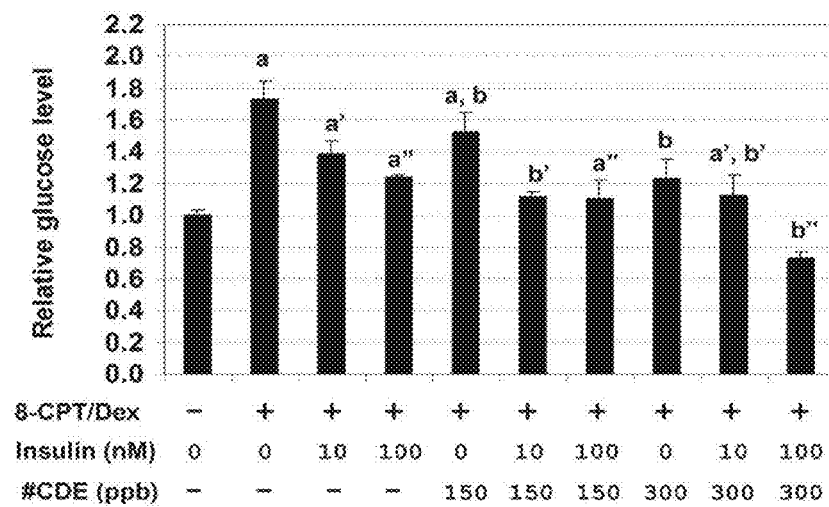
FIGS. 10A-10C show the effect of Compounds CDE on glucose production, G6pc mRNA expression, and extracellular LDH activity in primary mouse hepatocytes stimulated with 8-CPT/Dex.
Figure 10B:
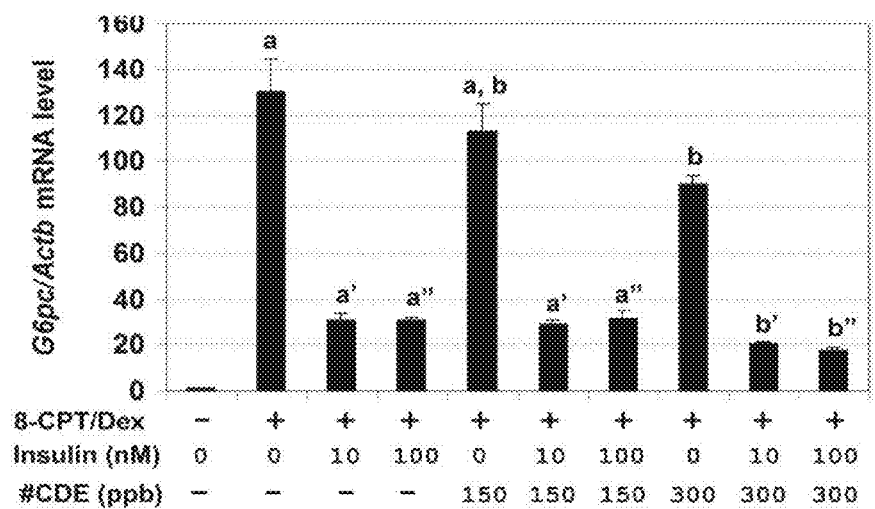
Figure 10C:
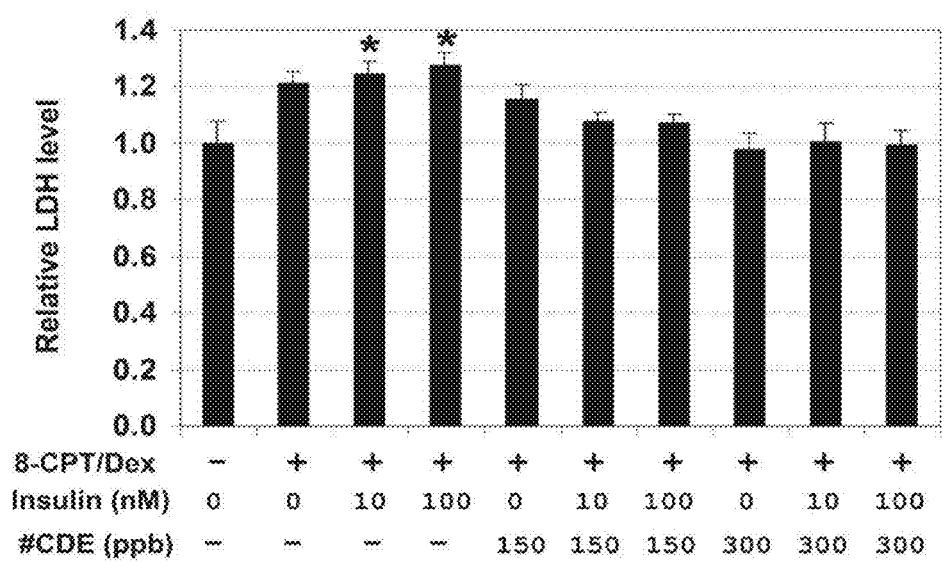

In brief, primary mouse hepatocytes were pretreated with control (water) or 150 or 300 ppb Compounds CDE combination in 10% FBS DMEM/F12 media for 24 hours followed by retreatment of these selenium compounds in the presence or absence of 10 or 100 nM insulin, 0.1 mM 8-CPT and 0.5 µM Dex in serum-free media for 6 hours. After these treatments, culture media were collected for glucose and LDH assays as described earlier. Also a duplicate set of primary mouse hepatocytes (from the same batch of hepatocytes) after the same treatments as described above were subjected to QRT-PCR analysis of G6pc expression. Data are presented as mean±SEM of 3-4 samples. In FIGS. 10A-10B, different letters (a vs b, a' vs b' vs c', a" vs b" vs c") mean a significant difference between those two groups. In FIG. 10C, the * P<0.05 vs vehicle treatment group (the first bar in the graph).

As shown in FIG. 10A, treatment with 8-CPT/Dex caused a significant increase in glucose production when compared to control only treatment group. This data indicated that the cultured primary mouse hepatocytes are functional. Treatments with both doses of insulin significantly decreased 8-CPT/Dex-induced glucose production in the hepatocytes when compared to 8-CPT/Dex group (see FIG. 10A). Importantly, treatment with Compounds CDE at the dose of 150 ppb tended to inhibit 8-CPT/Dex-stimulated glucose production in hepatocytes. More dramatically, Compounds CDE at the dose of 300 ppb significantly inhibited 8-CPT/Dex-stimulated glucose production in hepatocytes and the extent of decreased glucose production was almost identical to the effects of 100 nM insulin. These results suggest that Compounds CDE at 300 ppb is as effective as insulin at the concentration of 100 nM to inhibit glucose production in primary hepatocytes even under conditions similar to diabetic conditions. These results are consistent with the findings observed in the no-8-CPT/Dex-cotreated primary mouse hepatocytes (FIG. 9A), further suggesting that Compounds CDE in combination will mimic insulin, but in an insulin-independent manner, to inhibit glucose production.

In addition, Compounds CDE at both tested doses in combination with 10 nM or 100 nM insulin not only significantly inhibited 8-CPT/Dex-induced glucose production in primary mouse hepatocytes when compared to 8-CPT/Dex treatment group, but also displayed more effectiveness in the process than Compounds CDE or insulin alone at the tested doses (FIG. 10A). For instance, the extent of decreased 8-CPT/Dex-induced glucose production in hepatocytes after treatment with the combination of 150 ppb of Compounds CDE and 10 nM insulin was more pronounced than 150 ppb of Compounds CDE or 10 nM insulin alone. More evidently, glucose production was further decreased in the hepatocytes after the treatment of 300 ppb of Compounds CDE and 100 nM insulin (a decrease to below the levels of control-treated cell group), even though Compounds CDE at 300 ppb or 100 nM insulin alone were very effective in the inhibition of 8-CPT/Dex-induced glucose production (FIG. 10A). The combinations of 10 nM insulin and Compounds CDE at 150 ppb or 300 ppb and the combination of 100 nM insulin and Compounds CDE at 150 ppb almost completely inhibited 8-CPT/Dex-induced glucose production (a decrease near to levels of control cells without 8-CPT/Dex treatment). These results demonstrate that Compounds CDE can either replace or improve insulin action to inhibit 8-CPT/Dex-induced glucose production in primary mouse hepatocytes.

As described earlier, it was found that Compounds CDE in combination can mimic insulin to inhibit 8-CPT/Dex-induced G6pc expression and improve insulin action in the process in AML-12 cells (see FIG. 4). The inhibition of G6pc expression could lead to an inhibition of glucose production in primary mouse hepatocytes. Thus, mouse hepatocytes were pretreated with water (control) or 150 or 300 ppb Compounds CDE combination in 10% FBS DMEM/F12 media for 24 hours followed by retreatment of these selenium compounds in the presence or absence of 10 or 100 nM insulin, 0.1 mM 8-CPT and 0.5 µM Dex in serum-free media for 6 hours. After these treatments, cells were collected and subjected to QRT-PCR analysis of G6pc expression.

As shown in FIG. 10B, 8-CPT/Dex caused a great increase (about 130-fold increase) in the expression of G6pc mRNA. These data further confirming that the hepatocytes were functioning correctly. Treatment with both doses of insulin significantly decreased 8-CPT/Dex-induced G6pc expression in primary mouse hepatocytes when compared to 8-CPT/Dex group (when compared to 8-CPT/Dex group in the bar graph in FIG. 10B). Similar to the above glucose studies, Compounds CDE treatment at the dose of 150 ppb showed a trend, albeit non-significant, to inhibit 8-CPT/Dex-stimulated G6pc in hepatocytes (see FIG. 10B). However, Compounds CDE at the dose of 300 ppb significantly inhibited 8-CPT/Dex-induced G6pc mRNA expression, but this was not as potent as the tested doses of insulin (see FIG. 10B). These results clearly demonstrate that Compounds CDE can inhibit 8-CPT/Dex-induced G6pc expression in an insulin-independent manner, similar to the results obtained in AML-12 cells (FIG. 4).

Treatment of Compounds CDE at 300 ppb in combination with 10 nM or 100 nM insulin further significantly inhibited 8-CPT/Dex-stimulated G6pc expression in hepatocytes when compared to 10 or 100 nM insulin or 300 ppb Compounds CDE treatment. These results are indicated in FIG. 10B by a' vs b' or a'' vs b'' in the bar graph. These results indicate that the combination of insulin and Compounds CDE at 300 ppb was even more effective in inhibiting increased expression of G6pc by 8-CPT/Dex.

The above studies demonstrate that Compounds CDE, especially at the dose of 300 ppb, can mimic insulin, albeit less effectively than insulin, to inhibit 8-CPT/Dex-induced G6pc expression and improve insulin action in the process in the primary mouse hepatocytes. These results are partly consistent with the findings observed in AML-12 cells (FIG. 4). Since G6pc is required for glucose production, the above observed inhibition of 8-CPT/Dex-stimulated glucose production by Compounds CDE (FIG. 10A) is at least partly due to their downregulation of G6pc expression in primary mouse hepatocytes (FIG. 10B).

The LDH levels in the cultured media of the above treated hepatocytes was examined to further investigate whether Compounds CDE are toxic to primary hepatocytes cultured in the presence of 8-CPT/Dex and whether the above observed decrease of glucose production and G6pc expression by Compound CDE (FIG. 10A-B) is due to potential toxicity (as indicated by elevated LDH levels in the medium) of Compounds CDE in the hepatocytes.

As shown in FIG. 10C, treatments of 8-CPT/Dex either in the absence or presence of insulin slightly enhanced LDH levels when compared to vehicle control. However, there was no significant increase of LDH levels in hepatocytes after treatment with 8-CPT/Dex along with Compounds CDE at both tested doses in the absence or the presence of insulin (see FIG. 10C). Also, the slightly increased LDH levels in hepatocytes after treatment with 8-CPT/Dex and insulin were not observed by the co-treatment with Compounds CDE at both tested doses (see FIG. 10C).

These results further indicate that Compounds CDE are not toxic to primary hepatocytes cultured in the presence of 8-CPT/Dex. Also, these results exclude the possibility that the above observed decrease of 8-CPT/Dex-stimulated glucose production and G6pc expression (see FIGS. 10A and 10B) is caused by less healthy hepatocytes in primary mouse hepatocytes after Compounds CDE treatment.

In summary, the above studies demonstrate that Compounds CDE can mimic insulin to inhibit glucose production and G6pc expression and improve insulin action in these processes with no toxicity in primary mouse hepatocytes even under conditions similar to diabetic conditions (stimulated by 8-CPT/Dex).

The inhibition of glucose production by Compounds CDE (described above) was characterized in primary mouse hepatocytes pretreated with the compounds of the present disclosure in serum-containing media. To further confirm that Compounds CDE can mimic insulin to inhibit glucose production in an insulin-independent and other growth factor-independent manner, totally serum-free culture conditions were adopted to remove any potential trace of insulin or other growth factors in FBS. The effects of Compounds CDE on glucose production as well as its potential toxic effect (i.e., LDH level in culture media) in primary mouse hepatocytes cultured under serum-free conditions were examined.

Figure 11A:
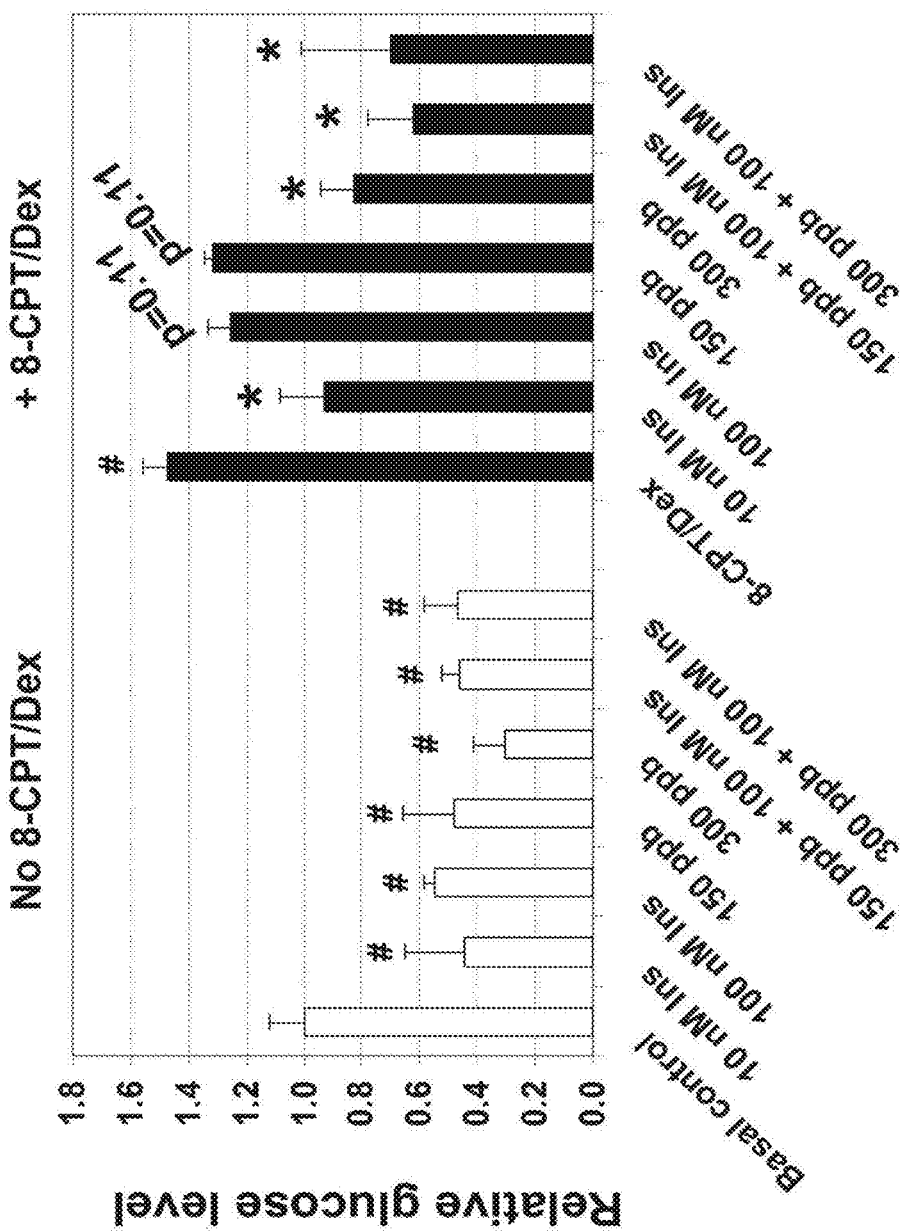
FIGS. 11A-11B show the effect of Compounds CDE on glucose production and extracellular LDH activity in primary mouse hepatocytes cultured in serum-free media.

In brief, primary mouse hepatocytes were serum-starved overnight. The cells were then treated with control (water), or 150 ppb or 300 ppb of Compounds CDE in the presence or absence of insulin, 8-CPT, and Dex in totally serum-free media for a short time period (i.e., 6 hours). Then media were collected and subjected to glucose and LDH analysis and cultured cells to protein analysis for normalization of glucose production and LDH level. Data are presented as mean±SEM of 3 samples. In FIG. 11A, the # P<0.05 vs basal control group (the first bar in the graph) and the * P<0.05 vs the 8-CPT/Dex treatment group (the first filled bar in the graph.

Figure 11B:
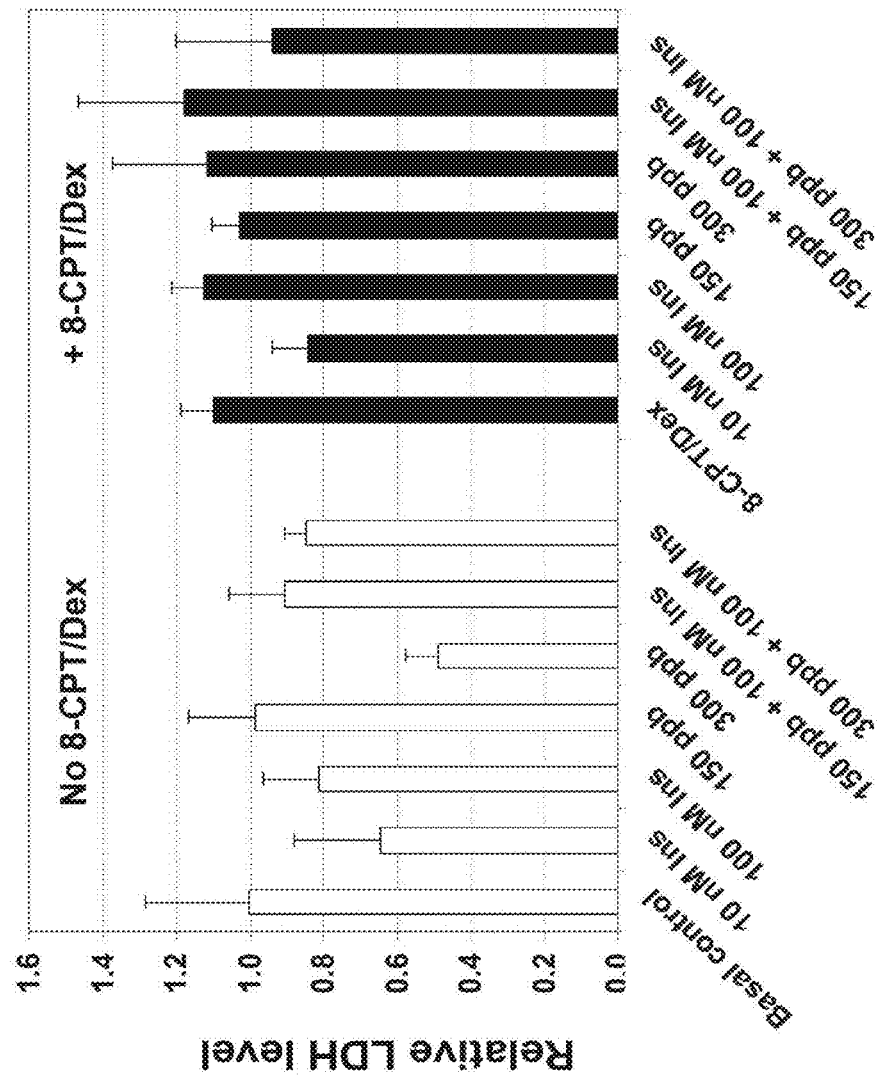

The effects of Compounds CDE on glucose production in mouse hepatocytes without co-treatments of 8-CPT/Dex were investigated (see FIGS. 11A-11B). As shown in FIG. 11A, treatments of both doses of insulin alone significantly inhibited glucose production by about 40-47% decrease in primary mouse hepatocytes. These results indicate that this batch of primary mouse hepatocytes was biologically functional.

More importantly, treatments with Compounds CDE at 150 ppb caused a significant decrease of glucose production in primary mouse hepatocytes as effectively as 100 nM insulin, while Compounds CDE at 300 ppb were even more effective than 100 nM insulin in inhibiting glucose production (see FIG. 11A). Cotreatments with both Compounds CDE and insulin also significantly inhibited glucose production, even though there was no additive or synergistic action between insulin and Compounds CDE in these primary hepatocytes. These results were consistent with the results obtained from hepatocytes pretreated with Compounds CDE in FBS-containing media (see FIG. 9A). Together, these results clearly demonstrate that Compounds CDE can mimic insulin, as effectively as or even more effectively than insulin at the concentration of 100 nM, to inhibit glucose production in an insulin- and growth factor-independent manner. It can also be concluded that Compounds CDE are effective in the inhibition of glucose production in primary mouse hepatocytes after a relatively short time of treatment (i.e., 6 hours), similar to insulin.

Compounds CDE were also tested to see whether 8-CPT/Dex-stimulated glucose production was inhibited in mouse hepatocytes under serum-free culture conditions. As shown in FIG. 11A, treatment with 8-CPT/Dex did cause a significant increase in glucose production when compared to a basal control group (vehicle treated), further indicating that this batch of primary mouse hepatocytes was biologically functioning. Treatment with 10 nM insulin significantly inhibited glucose production, even though there was only a trend of decreased glucose production in hepatocytes after treated with 100 nM insulin. The latter result could be due to a small number of tested samples (n=3) in which glucose production in one sample was pretty large when compared to other two samples in the same group (data not shown).

More importantly, treatment of Compounds CDE at 150 ppb showed a tendency to inhibit 8-CPT/Dex-stimulated glucose production, while Compounds CDE at the concentration of 300 ppb was as effective as insulin at 10 nM to significantly inhibit 8-CPT/Dex-stimulated glucose production in an insulin-independent or other growth factor-independent manner (FIG. 11A). It should be noted that Compounds CDE at the concentration of 300 ppb almost completely abolished the stimulatory effects of 8-CPT/Dex, as the glucose level in this treatment group was comparable to basal control group without 8-CPT/Dex stimulation.

Similarly, cotreatments of both Compounds CDE and insulin also significantly inhibited 8-CPT/Dex-stimulated glucose production (see FIG. 11A). In addition, there was a more pronounced decrease of 8-CPT/Dex-stimulated glucose production by the combination of 150 ppb Compounds CDE and 100 nM insulin than 150 ppb Compound CDE or 100 nM insulin alone. These results indicated that there exists an additive action between Compounds CDE and insulin in the process (FIG. 11A).

The effects of Compounds CDE to inhibit 8-CPT/Dex-stimulated glucose production in the above serum-free culture primary mouse hepatocytes are consistent with the findings observed in hepatocytes pretreated with Compounds CDE in serum-containing media (FIG. 10A). Since hepatocytes were serum-starved and treated with Compounds CDE in totally serum-free condition, these data clearly demonstrate that Compounds CDE can mimic insulin, at least as effective as 10 nM insulin, to inhibit 8-CPT/Dex-stimulated glucose production in an insulin-independent and growth factor-independent manner. It can also be concluded that the compounds described herein act rapidly, after a relatively very short treatment time, to inhibit 8-CPT/Dex-stimulated glucose production in these serum-free culture primary mouse hepatocytes, similar to insulin action. There also exists an additive or synergistic action between Compounds CDE and insulin, at least between 150 ppb Compounds CDE and 100 nM insulin doses, on the inhibition of 8-CPT/Dex-stimulated glucose production in these serum-free culture primary mouse hepatocytes (see FIG. 11A).

Finally, Compounds CDE was tested to determine any toxicity to primary mouse hepatocytes that were cultured in serum-free condition. LDH levels in the culture media in primary mouse hepatocytes after the above treatments were examined and then normalized by their protein levels. As shown in FIG. 11B, there was no significant increase of LDH levels in hepatocytes after all of the above treatments when compared to basal control group containing a water vehicle-treated group (i.e., the first bar in FIG. 11B). These results indicated that there was no cell damage or cell membrane leakage in hepatocytes after exposure to Compound CDE. Instead, a significant decrease of LDH level was observed in hepatocytes after treated with a high 300 ppb dose of Compounds CDE (see FIG. 11B). Therefore, the results suggest that Compounds CDE is not toxic to primary hepatocytes and, instead, at a higher dose, may have some protective effect against cell membrane leakage in these cells. Also, these results exclude the possibility that the above observed inhibition of basal and 8-CPT/Dex-stimulated glucose production (see FIG. 11A) is caused by less healthy hepatocytes in primary mouse hepatocytes after Compounds CDE treatment.

In conclusion, the above studies on serum-free culture primary mouse hepatocytes demonstrate that Compounds CDE can mimic insulin to inhibit both basal and 8-CPT/Dex-stimulated glucose production in a FBS-independent, more specifically insulin- and growth factor-independent manner. Also, these results further suggest that Compounds CDE do not have toxicity on the liver cells.

Compounds CDE: Insulin-Independent Activation of PI3K/Pdk1/Akt Signaling to Enhance Foxo1/3/4 Phosphorylation in Primary Mouse Hepatocytes Our earlier studies on AML-12 cells suggest that Compounds CDE can mimic insulin to enhance Foxo3 and Foxo4 phosphorylation, resulting in inhibition of G6pc expression for glucose production (FIGS. 6A-6C, 7A-7C). It is well documented that insulin acts fast in liver cells to activate PI3K/PDK1/AKT signaling to inactive Foxo1, Foxo3, and Foxo4 transcription factors that very rapidly lower glucose production.

To further investigate whether Compounds CDE will mimic insulin but act in an insulin-independent manner to activate Pdk1/Akt signaling to subsequently enhance FOXO phosphorylation for the inhibition of glucose production, the phosphorylation status of these signaling molecules, key for gluconeogenesis, was investigated in primary mouse hepatocytes under two different culture/treatment conditions.

Compounds CDE Target Foxo1/3/4 Phosphorylation in Primary Mouse Hepatocytes Pretreated with Compounds CDE in Serum-Containing Media for 24 Hours Followed by in Serum-Free Media for 6 Hours To determine if the combination of Compounds CDE can mimic insulin to regulate PI3k/Pdk1/Akt/Foxo1/3/4 signaling, primary mouse hepatocytes were pretreated with control (water) or selenium Compounds CDE at the doses of 150 and 300 ppb in serum-containing DMEM/F12 media for 24 hours. This treatment was followed by retreatments with these selenium compounds in serum-free media for 6 hours. The control-pretreated hepatocytes were also incubated with 100 nM insulin for 6 hours. After these treatments, culture media were collected for the glucose and LDH analysis as detailed in FIGS. 9A-9C. Cells were collected and subjected to protein analysis to determine total protein levels for Western blot analysis of various PI3k/Pdk1/Akt/Foxo1/3/4 signaling molecules. Protein expression levels of these signaling molecules were normalized by Actb protein levels and are presented as mean±SEM of three samples in FIG. 12B-F. Different letters in the bar graphs in FIG. 12B-F means a significant difference between those two groups ($P<0.05$).

As shown in FIG. 12A, insulin treatment caused a significant increase of the phosphorylated forms of Pdk1, Akt at serine residue 473, Foxo1 at threonine 24 (pFoxo1T24), Foxo3 at threonine 32 (pFoxo3T32), but not Gsk3b at serine 9 (pGsk3bS9) while the levels of phosphorylated Foxo4 at threonine 28 (pFoxo4T28) in these cells after insulin treatment were barely detectable. These results suggest that insulin indeed can regulate PI3k/Pdk1/Akt signaling to inactivate Foxo1 and Foxo3 in these hepatocytes under the above described experimental conditions. More importantly, the protein levels of pPdk1, pAktS473, pFoxo1T24 and pFoxo3T32, but not pGsk3bS9 were visibly elevated in these hepatocytes after treatments of both doses of Compounds CDE (FIG. 12A). In addition, pFoxo4T28 levels were also robustly increased in hepatocytes after the treatment of Compounds CDE at 300 ppb (FIG. 12A).

Quantitative analysis showed that there was approximately a 1.5-fold increase of pPdk1, 2.2-3-fold increase of pAktS473, 3-4-fold increase of pFoxo1T24 about a 3-fold increase of pFoxo3T32, but no increase of pGsk3bS9 in Compounds CDE-treated primary mouse hepatocytes (FIGS. 12B-F). The enhanced expression of pFoxo3T32 and pFoxo4T28 by Compounds CDE in primary mouse hepatocytes was consistent with our earlier observation in AML-12 cells (FIGS. 6A-6C, 7A-7C), even though enhanced pPdk1 and pAkt were not observed in AML-12 cells at 6 hours of Compounds CDE treatment (FIGS. 6A-6C, 7A-7C).

The enhanced pPdk1 and pAktS473 protein levels in these hepatocytes caused by insulin and compounds CDE at both tested doses indicate that Compounds CDE, like insulin, can activate Pdk1/Akt signaling. Although the extent of enhanced phosphorylation of pAkt/Foxo1/3 by Compounds CDE was not as strong as 100 nM insulin, Compounds CDE at both tested doses were as effective as 100 nM insulin to inhibit glucose production in primary mouse hepatocytes under the same experimental conditions (FIG. 9A). Thus it appears that an approximate 3-4-fold increase of pFoxo1T24 and pFoxo3T32 by Compounds CDE (FIGS. 12D-E) was enough to inactivate Foxo1 and Foxo3, leading to inhibition of G6pc expression and glucose production in these primary mouse hepatocytes. Our results clearly demonstrate that Compounds CDE can mimic insulin to activate PI3K/Pdk1/Akt signaling to enhance Foxo1/3/4 phosphorylation in the primary mouse hepatocytes under the above described culture and treatment conditions.

Compounds CDE Act Rapidly to Sequentially Activate Pdk1/Akt Signaling to Enhance Foxo1/3 Phosphorylation in Primary Hepatocytes Under Serum-Free Conditions To further investigate whether Compounds CDE can mimic insulin to activate PI3K signaling to enhance Foxo1/3 phosphorylation, time-course expression studies of these signaling molecules in primary mouse hepatocytes under serum-free conditions was performed. In brief, primary mouse hepatocytes were serum-starved overnight and then incubated with selenium Compounds CDE at the dose of 300 ppb in serum-free DMEM/F12 media for 0 minute, 5 minutes, 30 minutes, 1 hour, 2 hours and 3 hours. After treatments, hepatocytes were collected and subjected to Western blot analysis.

As shown in FIGS. 13A-B, phosphorylated Pdk1 levels tend to be increased in these serum-free culture hepatocytes at 5 minutes after the treatment with Compounds CDE. After 30 minutes of Compounds CDE treatment, there was a robust and significant increase of pPdk1 levels in these hepatocytes (FIGS. 13A-B). These results suggest that Compounds CDE can quickly activate PI3k/Pdk1 signaling in these hepatocytes. Subsequent to the activation of Pdk1, there was a trend towards increased pAktT308 levels in hepatocytes at 30 minutes of Compounds CDE treatment and, more importantly, a robust and significant increase of pAktT308 after 1 hour of Compounds CDE treatment (FIGS. 13A, C). These results suggest that Compounds CDE can subsequently activate Akt.

The levels of both pFoxo1T24 and pFoxo3T32, the downstream targets of activated PI3k/Pdk1/Akt signaling, were not affected in hepatocytes by Compounds CDE before 30 minutes of incubation (FIGS. 13A, D). At 1 hour treatment with Compounds CDE, there was a trend towards increased phosphorylation of Foxo1 and Foxo3 in the hepatocytes (FIG. 13D). At 2 and 3 hours of treatment, Compounds CDE significantly enhanced the phosphorylation of both Foxo1 and Foxo3 in these primary mouse hepatocytes cultured under the serum-free conditions (FIGS. 13A, D). Thus, there exists a sequential activation of Pdk1 and Akt followed by enhanced Foxo1 and Foxo3 phosphorylation by Compounds CDE in these hepatocytes, and these events occur less than two hours after treatment with Compounds CDE in a very similar fashion to insulin action. Considering that there is no insulin or growth factors in the plain DMEM/F12 medium, and no FBS was added in the culture media in these experiments, the enhancement of phosphorylation of Pdk1, Akt, Foxo1 and Foxo3 by Compounds CDE in these hepatocytes is independent of FBS, growth factors or insulin. In other words, Compounds CDE can bypass insulin or growth factors action to quickly activate PI3k/Pdk1/Akt signaling and subsequently inactivate Foxo1 and Foxo3 (enhanced Foxo1/3 phosphorylation) in the primary mouse hepatocytes.

Summary

Our studies demonstrate that Compounds CDE can mimic insulin to inhibit glucose production in primary mouse hepatocytes in an insulin-independent manner without being toxic to liver cells. These findings were clearly established from the studies in primary mouse hepatocytes that were cultured under three different conditions. First, it was found that glucose production was remarkably decreased by pretreatment with Compounds CDE in serum-containing media for 24 hours followed by retreatment of these compounds in serum-free media for 6 hours, with the effectiveness comparable to insulin at the dose of 100 nM (FIG. 9A). Next, glucose production was also found to be significantly inhibited in primary mouse hepatocytes by pretreatment with Compounds CDE in serum-containing media for 24 hours followed by retreatment of these compounds in serum-free media in the presence of 8-CPT/Dex (the stimuli of glucose production to mimic the diabetic conditions) for 6 hours, and that the effectiveness of 300 ppb of Compounds CDE in the process was comparable to insulin at the concentration of 100 nM (FIG. 10A). Finally, we adopted the serum-free culture technique and demonstrated that Compounds CDE can mimic insulin to inhibit both basal and 8-CPT/Dex-stimulated glucose production in a FBS-independent or, more specifically, insulin- and growth factor-independent manner after a short treatment time (6 hour treatment) (FIG. 11A). Also, the effectiveness of Compounds CDE in the inhibition of glucose production was comparable to insulin at least at the dose of 10 nM (FIG. 11A). In addition, treatment with Compounds CDE did not have a toxic effect (such as eliciting cell membrane leakage) on the health of primary mouse hepatocytes cultured under the above described three different conditions, since there was no significant increase of LDH in the culture media after Compounds CDE treatment (FIGS. 9C, 10C, 11B).

The reduced glucose production observed in these studies is at least in part attributed to inhibition of G6pc expression in primary mouse hepatocytes by Compounds CDE. It was found that Compounds CDE at 300 ppb caused a significant decrease (42% decrease) in G6pc mRNA levels in hepatocytes while a trend towards decreased G6pc expression (about 31% decrease, albeit not statistically significant) was also observed in hepatocytes after treatment with 150 ppb Compounds CDE (FIG. 9B) Similar results were also obtained in primary mouse hepatocytes stimulated by 8-CPT/Dex (FIG. 10B). Therefore, these results clearly demonstrate that Compounds CDE can mimic insulin to inhibit G6pc expression in primary mouse hepatocytes even in the presence of 8-CPT/Dex in an insulin-independent manner. These results are consistent with the findings observed in AML-12 cells (FIGS. 3-4).

It should be noted that the extent of reduced G6pc expression by Compounds CDE at the higher tested dose was smaller than insulin (10 nM) in primary mouse hepatocytes under the above described two culture conditions (i.e., with or without cotreatment of 8-CPT/Dex), whereas Compounds CDE were as effective as insulin at least at the dose of 10 nM to inhibit basal and 8-CPT/Dex-stimulated glucose production in the hepatocytes (FIGS. 9A, 10A, 11B). Thus it is possible that besides G6pc, Compounds CDE may regulate other molecules to lower the glucose levels in cultured mouse hepatocytes. Regardless, our results suggest that the inhibition of glucose production in primary mouse hepatocytes by Compounds CDE is at least partly due to their inhibition of G6pc expression.

In addition, the results also demonstrate that Compounds CDE can improve or augment insulin action to inhibit glucose production and G6pc expression in primary mouse hepatocytes under simulated diabetic conditions (using 8-CPT/Dex) (FIGS. 10A-B, 11A). These were supported by the following observations:
(1) a more pronounced decrease of 8-CPT/Dex-induced glucose production in the hepatocytes by the combination of 150 ppb Compounds CDE and 10 nM insulin than with 150 ppb Compounds CDE or 10 nM insulin alone (FIG. 10A);
(2) a further decrease of 8-CPT/Dex-induced glucose production in the hepatocytes by the combination of 300 ppb of Compounds CDE and 100 nM insulin than with 300 ppb of Compounds CDE or 100 nM insulin alone (FIG. 10A);
(3) a more pronounced decrease of 8-CPT/Dex-stimulated glucose production by the combination of 150 ppb of Compounds CDE and 100 nM insulin than 150 ppb of Compounds CDE or 100 nM insulin alone in hepatocytes in serum-free condition (FIG. 11A); and
(4) a more pronounced decrease of 8-CPT/Dex-induced G6pc expression by the combination of 300 ppb of Compounds CDE and insulin (10 and 100 nM) than with 300 ppb of Compounds CDE, 10 or 100 nM insulin alone (FIG. 10B).

A more pronounced inhibition of 8-CPT/Dex-induced G6pc expression by the combination of Compounds CDE and insulin than Compounds CDE or insulin alone was also observed in AML-12 cells (FIG. 4). Together, our results demonstrate that Compounds CDE can improve insulin action to inhibit 8-CPT/Dex-induced glucose production and G6pc expression in primary mouse hepatocytes.

Furthermore, the analyses of signaling molecules demonstrate that Compounds CDE can mimic insulin to quickly activate PI3K/Pdk1/Akt signaling to enhance the phosphorylation of Foxo1, 3 and 4 in primary mouse hepatocytes. Western blot analysis of phosphorylated proteins of these molecules in mouse hepatocytes either pretreated with Compounds CDE in serum-containing media for 24 hours followed by retreatments of these compounds in serum-free media for 6 hours (FIGS. 12A-12F), or treated with these compounds in totally serum-free condition for a short time from 5 to 180 minutes (FIGS. 13A-13D) support this conclusion.

In AML-12 cells, we also found that Compounds CDE can target Foxo3/4 to enhance their phosphorylation, even though increased phosphorylation of Pdk1 and Akt were not observed in AML-12 cells at the tested time period (6 hours after Compounds CDE treatment) (FIGS. 6A-6C, 7A-7C). The latter result could be due to the potential transient activation of Pdk1/Akt by Compounds CDE which may occur at an earlier time point (before 6 hours).

Regardless, the studies in primary mouse hepatocytes clearly demonstrate that Compounds CDE can bypass insulin or any growth factors to quickly activate PI3k/Pdk1/Akt signaling and subsequently enhance Foxo1/3/4 phosphorylation. Since FOXO proteins, especially Foxo1, in the liver are important for the regulation of G6pc expression and glucose production, the inhibited glucose production and G6pc expression observed above in primary mouse hepatocyte by Compounds CDE is most likely caused by inactivation of Foxo1/3/4 resulting from insulin-independent activation of Pdk1/Akt signaling and subsequently enhanced Foxo1/3/4 phosphorylation. Also the improvement of insulin action in the above process is also likely due to additive effects of enhanced Foxo1/3/4 phosphorylation by Compounds CDE and insulin.

In short, we have uncovered a selenium compound combination which can bypass insulin action to inhibit glucose production and G6pc expression in primary mouse hepatocytes even in the presence of diabetic stimuli for glucose production and without being toxic to the liver cells. Also, this compound combination, Compounds CDE, can improve insulin action to further inhibit diabetic stimuli-induced glucose production and G6pc expression in primary mouse hepatocytes. Furthermore, this compound combination can also mimic but bypass insulin to quickly activate PI3k/Pdk1/Akt signaling, and subsequently, enhance Foxo1/3/4 phosphorylation in the hepatocytes. Therefore, this compound combination can be used not only as a potent insulin-replacement medicine but also as an insulin-potentiating medicine for the treatments of both type I and II diabetics. Compounds CDE in combination may be useful in the treatment of obesity by bypassing insulin to reduce hepatic glucose output through insulin-independent inactivation of Foxo1/3/4, inhibition of Foxo-mediated G6pc expression and/or improvement of insulin action in these processes in the liver or administered to prevent liver cells becoming insulin-resistant.

Example 7

Reduction of Glucose Levels in the Bloodstream and Improved Glucose Tolerance in Response to Combined Treatment with Compounds CDE in Insulin-Resistant and Diabetic Leptin Receptor (Lepr) Spontaneous Null Mutant Mice Materials and Methods
Compounds Compound C (5'-Methylselenoadenosine), Compound D (Se-Adenosyl-L-homocysteine) and Compound E (Gamma-glutamyl-methylseleno-cysteine), were synthesized in the Chemistry Laboratory of Alltech, Inc. The purities of all tested compounds were verified to be ≥99%, as determined by Mass-Spectrometry.
Animals and Treatments Adult heterozygous diabetic spontaneous mutation (leptin receptor mutation) $Lepr^{db/+}$ mice (C57BL/6J strain) were purchased from The Jackson Laboratory (Bar Harbor, Me.) and then intercrossed to generate homozygous $Lepr^{db/db}$ mice (determined by mouse genotyping). Mouse tail genotyping at weaning time (at postnatal day 21) was performed, according to the protocol from The Jackson Laboratory. These $Lepr^{db/db}$ mice at postnatal day 27 were intraperitoneally injected with physiological saline (0.09% NaCl) or Compounds CDE. Compounds CDE comprise Compound C, Compound D and Compound E in combination (5 µg selenium of each compound per kilogram body weight equivalent to 5 ppb of each selenium compound per injection) every other day until the age of 3.5 months, and then subjected to glucose analysis and glucose-tolerance assays. Body weights of the above treated mice were recorded using a balance every week, and any visible abnormal animal gross morphology and walking behavior were monitored daily.

Additional 5-week-old male $Lepr^{db/db}$ mice were purchased from the Jackson Laboratory and intraperitoneally injected daily with physiological saline (0.09% NaCl) or Compounds CDE. Compounds CDE comprise Compound C, Compound D and Compound E in combination (5 µg selenium of each compound per kilogram body weight, diluted in the sterile physiological saline) starting on postnatal day 38 for 28 days. This experiment was designed to test the potential use of these compounds as an acute diabetes treatment ($Lepr^{db/db}$ mice of >35 days old have or will soon develop hyperglycemia). Testing the younger mice which had been injected for a longer period was intended to evaluate the compounds more as a preventive preparation for pre-diabetic or at-risk subjects. Also body weights of the above treated mice were recorded using a balance every week and any visible abnormal animal gross morphology and walking behavior were monitored daily.

Blood Glucose Assay

After the last injection of physiological saline or Compounds CDE, mice were fasted overnight. Then a small drop of blood from these mice was collected by snipping the mouse tail tip and blood glucose levels were determined using a Glucometer with a maximum capability for glucose measurement of 600 mg/dL.

Glucose Tolerance Test and Quantitation of Area Under Curve (AUC)

Glucose tolerance tests were performed as described previously (Li et al, $Int\ J\ Biol\ Sci$ 2008; 4:29-36). Briefly, overnight-fasted $Lepr^{db/db}$ mice after saline or Compounds CDE treatment were injected intraperitoneally with 2 grams/kg body weight of 20% D-glucose. Blood glucose levels at time 0 (immediately before the injection of glucose), 0.25, 0.5, 1 and 2 hours after injection of glucose were determined using a glucometer with a maximum glucose measurement capacity of 600 mg/dL. Because of this, blood glucose levels over 600 mg/dL were counted as 600 mg/dL in our data analysis. The quantitation of the area under the curve (AUC) of each mouse in the above glucose test assay was calculated by using Microsoft Excel.

Statistical Analysis

Where applicable, a Student's t-test was used to determine the statistical significance of difference between saline- and Compounds CDE-treated groups with a P value less than 0.05. Data are presented as mean±SEM of the indicated numbers of mice in the figures.

Results and Discussion $Lepr^{db/db}$ mice lack all known isoforms of the leptin receptor gene (Lepr). This homozygous mouse model is an aggressive Type II diabetic mouse model with impaired glucose tolerance, reduced insulin sensitivity, hyperglycemia and hyperinsulinemia. These mice display gross obesity at around 3 to 4 weeks of age, elevation of plasma insulin beginning at 10 to 14 days and hyperglycemia (i.e., high blood sugar levels) at 4 to eight 8 of age (Coleman D L. 1978 Diabetologia 14:141-8).

The studies on AML-12 cells and primary mouse hepatocytes described herein indicate that Compounds CDE can mimic insulin but bypass insulin to inactivate Foxo1, Foxo3, and Foxo4 in liver cells. In addition, Compounds CDE can inhibit Foxo-mediated G6pc expression to lower glucose production without being toxic to these liver cells (FIGS. 1, 2A-2B, 3, 4, 6A-6C, 7A-7C, 9A-9C, 10A-10C, 11A-11B, 12A-12F, 13A-13D, 14A-14B, 15A-15B). Also, these in vitro studies show that Compounds CDE can improve insulin action to lower glucose production and G6pc expression in liver cells under simulated diabetic conditions (FIGS. 4, 10A-10C, 11A-11B). Therefore, the $Lepr^{db/db}$ mouse model is an ideal model to investigate the use of this novel compound combination in potentially lowering glucose in the bloodstream and the improvement of insulin sensitivity and glucose tolerance against diabetes.

Reduction of Blood Glucose Levels in $Lepr^{db/db}$ Mice after Administration of Compounds CDE Both Before and after the Onset of Hyperglycemia Two administration regimes of Compounds CDE were adopted to investigate the potential role of Compounds CDE in the prevention and treatment of hyperglycemia as displayed in $Lepr^{db/db}$ mice. The compounds described herein were investigated to determine if they have any effects in preventing the development of hyperglycemia, which develops at the age of 4 to 8 weeks in $Lepr^{db/db}$ mice. Mice were administered treatments by intraperitoneal injection of Compounds CDE right before the onset of hyperglycemia.

In brief, juvenile $Lepr^{db/db}$ mice at the age of 27 days were injected intraperitoneally with Compounds CDE (5 µg selenium of each compound per kilogram body weight, equivalent to 5 ppb of each compound per injection in each mouse) or physiological saline every other day until mice reached the age of 3.5 months. At the end of treatment, the mice were fasted overnight and subjected to glucose analysis. The body weights of these treated mice were recorded using a balance every other day to test if there is any effect of these compounds on the body weight gain during the treatment time period. Data are presented as mean±SEM of indicated number of mice under the bar graphs in FIG. 14A.

It was found that treatment with Compounds CDE did not affect body weight gains in these mutant mice (data not shown), indicating that Compounds CDE likely has little or no inhibitory effects on the abnormally increased appetite for consumption of food displayed in $Lepr^{b/db}$ mice. Also, there was no visible difference in animal gross morphology and walking behavior between saline-treated (control) and Compounds CDE-treated $Lepr^{db/db}$ mice during the treatment period (data not shown). These results indicate that Compounds CDE at the tested doses had no effects on animal behavior or activity.

However, treatment with Compounds CDE caused a significant decrease, about 40% reduction compared to controls, of glucose levels in the bloodstream of $Lepr^{db/db}$ mice (see FIG. 14A) even though the blood glucose levels in Compounds CDE-treated $Lepr^{db/db}$ mice were still higher than normal wild-type mice at equivalent age (about 100 mg/dL, data not shown). Although Compounds CDE at the tested dose did not completely prevent the development of hyperglycemia in $Lepr^{db/db}$ mice, these results clearly demonstrate that Compounds CDE can significantly reduce glucose levels in the bloodstream in this severe Type II diabetes mouse model, indicating the potential of Compounds CDE for the prevention of hyperglycemia.

To further investigate the role of Compounds CDE in lowering glucose output in these diabetic $Lepr^{db/db}$ mice, another administration regime, in which Compounds CDE were injected intraperitoneally after or during the onset of hyperglycemia in $Lepr^{db/db}$ mice, was adopted to examine the blood glucose levels in these mice. In brief, $Lepr^{db/db}$ male mice at the age of 38 days were intraperitoneally injected with saline or Compounds CDE (5 μg selenium of each compound per kilogram body weight) daily for 28 days. Mouse body weight and any abnormal morphology or walking behavior were recorded or monitored daily.

After the above treatments, animals were fasted overnight and then subjected to blood glucose analysis. Similar to the above animal studies, treatment of Compounds CDE did not affect body weight gain, animal gross morphology and walking behavior in Lepr$^{db/db}$ mice during the treatment time period (data not shown). However, treatment with Compounds CDE caused a significant decrease (about 25% reduction) of blood glucose levels in these Lepr$^{db/db}$ mice when compared to saline-treated mice (see FIG. 14B). These studies further demonstrate that Compounds CDE can lower glucose output in these severe type II diabetes mice, indicating the potential of these compounds for the treatment of hyperglycemia.

In summary, these results demonstrate that Compounds CDE can lower glucose output in Lepr$^{db/db}$ mice by intraperitoneal injection of these compounds both before and after or during the onset of hyperglycemia in these mutant animals.

In addition, there were no visible morphological or walking behavior changes in Lepr$^{db/db}$ mice after the treatments of these compounds under the above described injection regimes. In fact, the acute effects of Compounds CDE on animal health in normal wild-type C57BL/6 mice was examined, but no observations of abnormal gross morphological and walking behavior abnormalities during one week after intraperitoneal injection of a high dose of Compounds CDE occurred (500 μg selenium of each compound per kilogram body weight, data not shown). Thus, Compounds CDE likely has little or no toxic effects in these mice.

Together, these results demonstrate that Compound CDEs can significantly lower blood glucose levels in a mouse model of aggressive Type II diabetes. These results indicate the potential of Compounds CDE both the prevention and the treatment of hyperglycemia in diabetic subjects.

Enhanced Glucose Tolerance in Diabetic Lepr$^{db/db}$ Mice after Administration of Compounds CDE Prior to the Onset of Hyperglycemia The glucose tolerance test identifies abnormalities in the way the body handles glucose after a high and rapid rise of blood sugar (e.g., usually after a meal). Insulin plays a critical role not only in the inhibition of glucose production in the liver, but also in glucose uptake, storage and metabolism in muscle, liver, and fat cells, causing a lower glucose levels in the bloodstream.

Diabetic patients have a very low glucose tolerance either due to their inability to produce insulin or respond to insulin efficiently to maintain glucose homeostasis. The in vitro studies described herein indicate that Compounds CDE not only can mimic insulin but also can bypass insulin and improve insulin action to inhibit glucose production and/or the expression of G6pc, a key gene for glucose production, in liver cells (FIGS. 2A-2B, 3, 4, 9A-9C, 10A-10C, 11A-11B). Lepr$^{db/db}$ mice are the ideal mouse Type II diabetic model to investigate the role of Compounds CDE in maintaining glucose homeostasis, considering that impaired glucose tolerance and insulin-resistance are displayed in these mutant mice. Therefore, Compounds CDE effect on improved glucose tolerance in Lepr$^{db/db}$ mice after intraperitoneal injection of Compounds CDE into mice from 27 days to 3.5 months of age was investigated.

Similar to the studies described above, Lepr$^{db/db}$ mice at the age of 27 days were injected intraperitoneally with physiological saline or Compounds CDE in combination (5 μg selenium of each compound per kilogram body weight equivalent to 5 ppb of each compound per injection in each mouse) every other day until mice reached the age of 3.5 months. At the end of treatment, these mice were fasted overnight, injected with glucose (2 g/kg body weight) and blood glucose levels measured at 0.25 hours (15 minutes), 0.5 hours (30 minutes), 1 hour (60 minutes) and 2 hours (120 minutes) post-glucose injection. The blood glucose levels immediately before the glucose injection (referred to as zero time point) were also recorded. Mean±SEM. The * in FIG. 15A indicates that P refers to at least <0.05 when compared to saline-treated group at the same time point.

As shown in FIG. 15A, a significant increase in blood glucose levels was observed in saline-treated Lepr$^{db/db}$ mice after injection of glucose beginning at 0.25 hours and at all the following tested time points. As stated, the glucose measurement limit of the glucometer employed for these analyses was 600 mg/dL. Thus, glucose levels in excess of this limit still had to be recorded as 600 mg/dL. The reason for stating this is to point out that measurements, particularly for the saline-treated animals, may well represent underestimations of the true blood glucose concentrations.

In Compounds CDE-treated Lepr$^{db/db}$ mice, blood glucose levels were significantly lower than saline-treated mice before the glucose injection Similar to saline-treated mice, five of six tested Compounds CDE-treated mice had blood glucose levels near or higher than 600 mg/dL at 0.5 hours and 1 hours after glucose injection (see FIG. 15A). However, blood glucose levels in all six tested Lepr$^{db/db}$ mice after treatment with Compounds CDE were significantly lower than saline-treated littermates at 2 hours after glucose injection (see FIG. 15A).

Quantitative analysis of the area under the curve (AUC) of the above graph shown in FIG. 15A demonstrates that there was also a significant decrease of blood glucose during the tested time period after glucose injection in Compounds CDE-treated Lepr$^{db/db}$ mice when compared to saline-treated mice (see FIG. 15B). Once again, however, due to the measurement limit of the glucometer, it is likely that this decrease was more dramatic than shown in FIG. 15B. Nevertheless, it must be emphasized that the decrease was still significantly different.

It was noted that glucose levels in Compounds CDE-treated Lepr$^{db/db}$ mice at 2 hours after glucose injection were still higher than glucose levels before the glucose injection (see FIG. 15A). These results suggest that a complete clearance of the administered glucose in the blood stream of Lepr$^{dbfilb}$ mice by Compounds CDE will likely take longer than the 2 hours monitoring period employed in this experiment.

In short, the above studies demonstrate that Compounds CDE at the tested dose can significantly improve glucose tolerance in Lepr$^{db/db}$ mice. The action of these compounds is likely mediated through the improvement of insulin sensitivity in the clearance of glucose in the liver as well as other organs such as muscle and adipose tissues.

Summary

These results demonstrate for the first time that Compounds CDE not only can lower fasting glucose levels (FIGS. 14A-14B), but can also improve glucose tolerance (FIGS. 15A-15B) in an aggressive Type II diabetic mouse model. Based on extensive cell culture work, the likely mode of action of Compound CDE in these animals is (1) to bypass insulin to inactivate Foxo1, Foxo3, Foxo4, leading to reduced G6pc expression and glucose production in liver cells, as demonstrated in primary mouse hepatocytes and AML-12 liver cells (see FIGS. 2A-2B, 3, 4, 6A-6C, 7A-7C, 9A-9C, 10A-10C, 11A-11B, 12A-12F, 13A-13D); (2) to improve insulin sensitivity by the inhibition of Foxo1, Foxo3, Foxo4-mediated G6pc expression and glucose production in the liver, as also indicated by studies on cultured liver cells (FIGS. 4, 10A-10C, 11A-11B); and/or (3) improve insulin action or bypass insulin to enhance the uptake and/or metabolism of glucose in liver, muscle and fat cells, as suggested in FIGS. 15A-15B. In addition, the improvement in insulin sensitivity may be due to the enhancement of Insr and Igf1r expression by Compounds CDE, as indicated by studies on mouse liver AML-12 cells (FIGS. 5A-5D).

Regardless, our studies demonstrate that Compounds CDE can inhibit glucose output and improve glucose tolerance in an insulin-resistant, diabetic mouse model. These results suggest that Compounds CDE can be developed for the treatment of hyperglycemia and insulin-insensitivity in diabetic patients. Besides, Compounds CDE can also be used for preventing the development of hyperglycemia in pre-diabetic subjects by its ability to lower glucose output in the bloodstream if administered prior to the onset of hyperglycemia in at risk patients. In addition, Compounds CDE may also be useful for the treatment of obesity due to its ability to lower glucose levels in the bloodstream.

All publications and patents mentioned in the present application are herein incorporated by reference. Various modification and variation of the described methods and compositions of the present application will be apparent to those skilled in the art without departing from the scope and spirit of the present application. Although the present application has been described in connection with specific preferred embodiments, it should be understood that the present application as claimed should not be unduly limited to such specific embodiments. Indeed, various modifications of the described modes for carrying out the present application that are obvious to those skilled in the relevant fields are intended to be within the scope of the following claims.

The invention claimed is:

1. A method of replacing insulin in a subject comprising: administering a composition to the subject, the composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), and a compound of Formula (III); and a carrier, wherein the composition contains at least about 0.033% (w/v) of each of the at least three different compounds that is selected, wherein Formula (I) is:

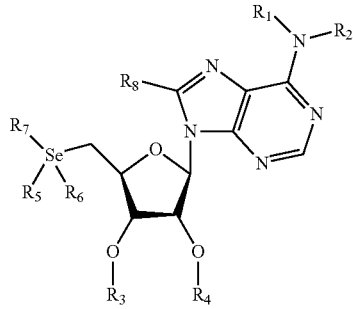

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan; and $R_8$ is hydrogen, azido, alkyl, alkenyl, or alkynyl, wherein Formula (II) is:

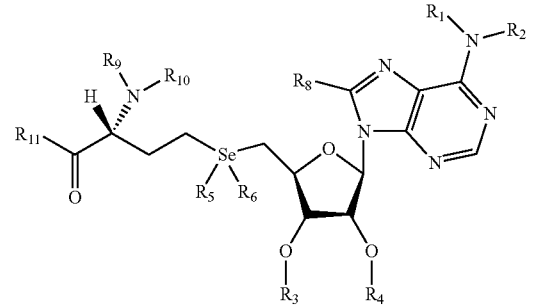

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_8$ is hydrogen, azido, alkyl, alkenyl, or alkynyl;

$R_9$ is H, acyl, alkyl, alkenyl, alkynyl, aralkyl, carboxyl, cycloalkyl, $C(O)R^c$, or $C(O)OR^c$, where $R^c$ is alkyl, cycloalkyl, aryl, aralkyl, or heterocyclyl; or $R_9$ together with $R_{10}$ form a heterocyclic ring having 4 to 8 ring members with at least one heteroatom selected from nitrogen;

$R_{10}$ is H, acyl, alkyl, alkenyl, alkynyl, aralkyl, carboxyl, cycloalkyl, $C(O)R^c$, or $C(O)OR^c$, where $R^c$ is selected from alkyl, cycloalkyl, aryl, aralkyl, or heterocyclyl; or $R_9$ together with $R_{10}$ form a heterocyclic ring having 4 to 8 ring members with at least one heteroatom selected from nitrogen; and $R_{11}$ is OR, alkoxy, aralkoxy, or amino, where R is selected from alkyl, cycloalkyl, aryl, aralkyl, or heterocyclyl, and wherein Formula (III) is:

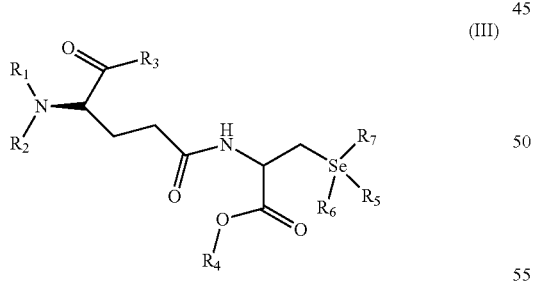

(III)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is OH, OR, alkoxy, aralkoxy, or amino, where R is selected from alkyl, cycloalkyl, aryl, aralkyl, or heterocyclyl;

$R_4$ is alkyl, alkenyl, alkynyl, cycloalkyl, aryl, aralkyl, or heterocyclyl;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl; and $R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

2. A method of enhancing insulin activity in a subject comprising:

administering a composition to the subject, the composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), and a compound of Formula (III); and a carrier, wherein the composition contains at least about 0.033% (w/v) of each of the at least three different compounds that is selected, wherein Formula (I) is:

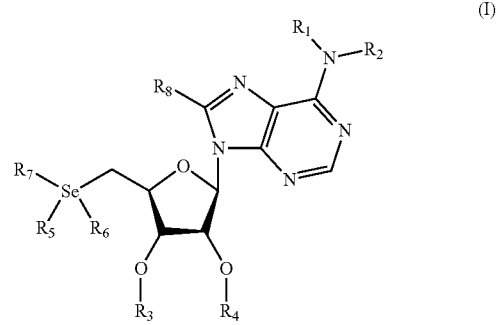

(I)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR", or is absent; wherein R" is selected from alkyl, alkenyl, alkynyl, cycloalkyl, aryl, or aralkyl;

$R_6$ is oxo, hydroxyl, alkyl, alkenyl, alkynyl, OR", or is absent; wherein R" is selected from alkyl, alkenyl, alkynyl, cycloalkyl, aryl, or aralkyl;

$R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan; and $R_8$ is hydrogen, azido, alkyl, alkenyl, or alkynyl, wherein Formula (II) is:

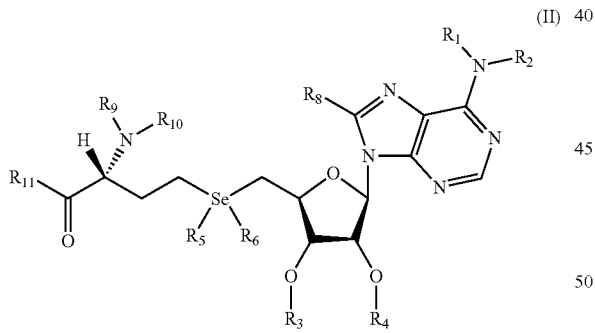

(II)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR", or is absent; wherein R" is selected from alkyl, alkenyl, alkynyl, cycloalkyl, aryl, or aralkyl;

$R_6$ is oxo, hydroxyl, alkyl, alkenyl, alkynyl, OR", or is absent; wherein R" is selected from alkyl, alkenyl, alkynyl, cycloalkyl, aryl, or aralkyl;

$R_8$ is hydrogen, azido, alkyl, alkenyl, or alkynyl;

$R_9$ is H, acyl, alkyl, alkenyl, alkynyl, aralkyl, carboxyl, cycloalkyl, $C(O)R^c$, or $C(O)OR^c$, where $R^c$ is alkyl, cycloalkyl, aryl, aralkyl, or heterocyclyl; or $R_9$ together with $R_{10}$ form a heterocyclic ring having 4 to 8 ring members with at least one heteroatom selected from nitrogen;

$R_{10}$ is H, acyl, alkyl, alkenyl, alkynyl, aralkyl, carboxyl, cycloalkyl, $C(O)R^c$, or $C(O)OR^c$, where $R^c$ is selected from alkyl, cycloalkyl, aryl, aralkyl, or heterocyclyl; or $R_9$ together with $R_{10}$ form a heterocyclic ring having 4 to 8 ring members with at least one heteroatom selected from nitrogen; and $R_{11}$ is OR, alkoxy, aralkoxy, or amino, where R is selected from alkyl, cycloalkyl, aryl, aralkyl, or heterocyclyl, and wherein Formula (III) is:

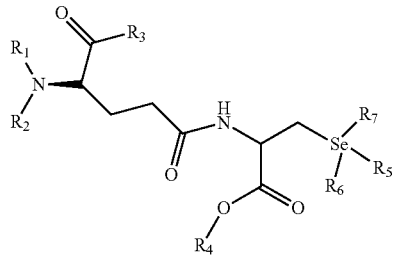

(III)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is OH, OR, alkoxy, aralkoxy, or amino, where R is selected from alkyl, cycloalkyl, aryl, aralkyl, or heterocyclyl;

$R_4$ is alkyl, alkenyl, alkynyl, cycloalkyl, aryl, aralkyl, or heterocyclyl;

R$_5$ is oxo, hydroxyl, alkyl, alkenyl, alkynyl, OR'', or is absent; wherein R'' is selected from alkyl, alkenyl, alkynyl, cycloalkyl, aryl, or aralkyl;

R$_6$ is oxo, hydroxyl, alkyl, alkenyl, alkynyl, OR'', or is absent; wherein R'' is selected from alkyl, alkenyl, alkynyl, cycloalkyl, aryl, or aralkyl; and R$_7$ is a C$_3$-C$_{16}$ alkyl, alkenyl, alkynyl, ketone, amino alcohol, amino acid, OR$^a$, Se—R$^b$, or S—R$^b$, wherein R$^a$ for OR$^a$ is selected from the group consisting of H, alkyl, cycloalkyl, aryl, aralkyl, and heterocyclyl, where R$^b$ for Se—R$^b$ is selected from the group consisting of H, C$_3$-C$_{16}$ alkyl, cycloalkyl, aryl, aralkyl, and heterocyclyl, wherein R$^b$ for S—R$^b$ is selected from the group consisting of H, C$_3$-C$_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

3. The method of claim 2, further comprising administering insulin or an analog or derivative thereof.

4. A method of inhibiting glucose production in a subject comprising:

administering a composition to the subject, the composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), and a compound of Formula (III); and a carrier, wherein the composition contains at least about 0.033% (w/v) of each of the at least three different compounds that is selected, wherein Formula (I) is:

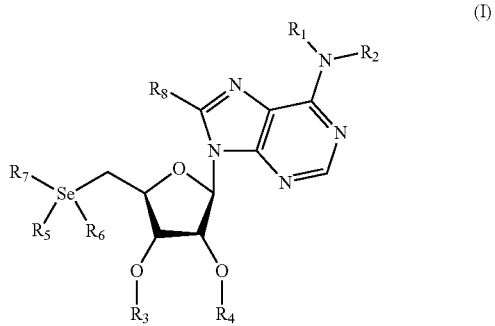

(I)

or a pharmaceutically acceptable salt, hydrate, or prodrug thereof, wherein

R$_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or R$_1$ together with R$_2$ form a heterocyclic ring having 4 to 8 ring members with at least one heteroatom selected from nitrogen;

R$_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or R$_1$ together with R$_2$ form a heterocyclic ring having 4 to 8 ring members with at least one heteroatom selected from nitrogen;

R$_3$ is H, acyl, alkyl, alkenyl, alkynyl, aralkyl, cycloalkyl, carboxyl, or C-amido; or R$_3$ together with R$_4$ and the atoms to which they are attached form a heterocyclic ring having 4 to 8 ring members with at least two heteroatoms selected from oxygen;

R$_4$ is H, acyl, alkyl, alkenyl, alkynyl, aralkyl, cycloalkyl, carboxyl, or C-amido; or R$_3$ together with R$_4$ and the atoms to which they are attached form a heterocyclic ring having 4 to 8 ring members with at least two heteroatoms selected from oxygen;

R$_5$ is oxo, hydroxyl, alkyl, alkenyl, alkynyl, OR'', or is absent; wherein R'' is selected from alkyl, alkenyl, alkynyl, cycloalkyl, aryl, or aralkyl;

R$_6$ is oxo, hydroxyl, alkyl, alkenyl, alkynyl, OR'', or is absent; wherein R'' is selected from alkyl, alkenyl, alkynyl, cycloalkyl, aryl, or aralkyl;

R$_7$ is a C$_3$-C$_{16}$ alkyl, alkenyl, alkynyl, ketone, amino alcohol, amino acid, OR$^a$, Se—R$^b$, or S—R$^b$, wherein R$^a$ for OR$^a$ is selected from the group consisting of H, alkyl, cycloalkyl, aryl, aralkyl, and heterocyclyl, where R$^b$ for Se—R$^b$ is selected from the group consisting of H, C$_3$-C$_{16}$ alkyl, cycloalkyl, aryl, aralkyl, and heterocyclyl, wherein R$^b$ for S—R$^b$ is selected from the group consisting of H, C$_3$-C$_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan; and R$_8$ is hydrogen, azido, alkyl, alkenyl, or alkynyl, wherein Formula (II) is:

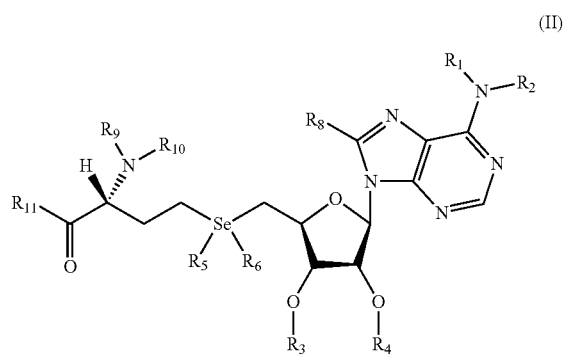

(II)

or a pharmaceutically acceptable salt, hydrate, or prodrug thereof, wherein

R$_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or R$_1$ together with R$_2$ form a heterocyclic ring having 4 to 8 ring members with at least one heteroatom selected from nitrogen;

R$_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or R$_1$ together with R$_2$ form a heterocyclic ring having 4 to 8 ring members with at least one heteroatom selected from nitrogen;

R$_3$ is H, acyl, alkyl, alkenyl, alkynyl, aralkyl, cycloalkyl, carboxyl, or C-amido; or R$_3$ together with R$_4$ and the atoms to which they are attached form a heterocyclic ring having 4 to 8 ring members with at least two heteroatoms selected from oxygen;

R4 is H, acyl, alkyl, alkenyl, alkynyl, aralkyl, cycloalkyl, carboxyl, or C-amido; or R3 together with R4 and the atoms to which they are attached form a heterocyclic ring having 4 to 8 ring members with at least two heteroatoms selected from oxygen;

R5 is oxo, hydroxyl, alkyl, alkenyl, alkynyl, OR", or is absent; wherein R" is selected from alkyl, alkenyl, alkynyl, cycloalkyl, aryl, or aralkyl;

R6 is oxo, hydroxyl, alkyl, alkenyl, alkynyl, OR", or is absent; wherein R" is selected from alkyl, alkenyl, alkynyl, cycloalkyl, aryl, or aralkyl;

R8 is hydrogen, azido, alkyl, alkenyl, or alkynyl;

R9 is H, acyl, alkyl, alkenyl, alkynyl, aralkyl, carboxyl, cycloalkyl, C(O)R$^c$, or C(O)OR$^c$, where R$^c$ is alkyl, cycloalkyl, aryl, aralkyl, or heterocyclyl; or R9 together with R10 form a heterocyclic ring having 4 to 8 ring members with at least one heteroatom selected from nitrogen;

R10 is H, acyl, alkyl, alkenyl, alkynyl, aralkyl, carboxyl, cycloalkyl, C(O)R$^c$, or C(O)OR$^c$, where R$^c$ is selected from alkyl, cycloalkyl, aryl, aralkyl, or heterocyclyl; or R9 together with R10 form a heterocyclic ring having 4 to 8 ring members with at least one heteroatom selected from nitrogen; and R11 is OR, alkoxy, aralkoxy, or amino, where R is selected from alkyl, cycloalkyl, aryl, aralkyl, or heterocyclyl, and wherein Formula (III) is:

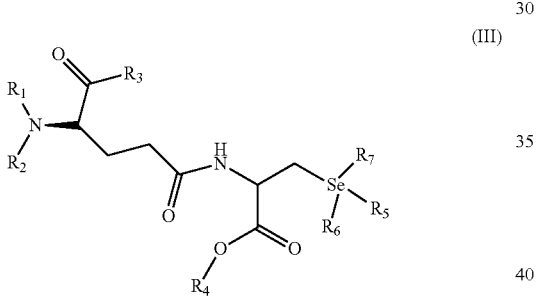

(III)

or a pharmaceutically acceptable salt, hydrate, or prodrug thereof, wherein

R1 is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or R1 together with R2 form a heterocyclic ring having 4 to 8 ring members with at least one heteroatom selected from nitrogen;

R2 is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or R1 together with R2 form a heterocyclic ring having 4 to 8 ring members with at least one heteroatom selected from nitrogen;

R3 is OH, OR, alkoxy, aralkoxy, or amino, where R is selected from alkyl, cycloalkyl, aryl, aralkyl, or heterocyclyl;

R4 is alkyl, alkenyl, alkynyl, cycloalkyl, aryl, aralkyl, or heterocyclyl;

R5 is oxo, hydroxyl, alkyl, alkenyl, alkynyl, OR", or is absent; wherein R" is selected from alkyl, alkenyl, alkynyl, cycloalkyl, aryl, or aralkyl;

R6 is oxo, hydroxyl, alkyl, alkenyl, alkynyl, OR", or is absent; wherein R" is selected from alkyl, alkenyl, alkynyl, cycloalkyl, aryl, or aralkyl; and R7 is a $C_3$-$C_{16}$ alkyl, alkenyl, alkynyl, ketone, amino alcohol, amino acid, OR$^a$, Se—R$^b$, or S—R$^b$, wherein R$^a$ for OR$^a$ is selected from the group consisting of H, alkyl, cycloalkyl, aryl, aralkyl, and heterocyclyl, where R$^b$ for Se—R$^b$ is selected from the group consisting of H, $C_3$-$C_{16}$ alkyl, cycloalkyl, aryl, aralkyl, and heterocyclyl, wherein R$^b$ for S—R$^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

5. A method of modulating glucose metabolism in a subject comprising:

administering a composition to the subject, the composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), and a compound of Formula (III); and a carrier, wherein the composition contains at least about 0.033% (w/v) of each of the at least three different compounds that is selected, wherein Formula (I) is:

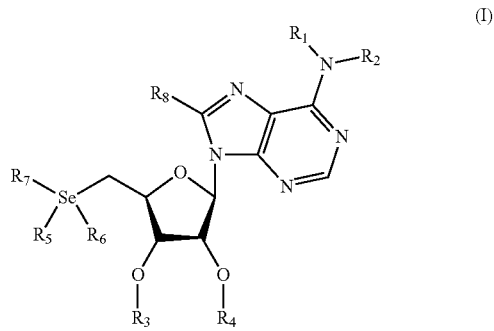

(I)

or a pharmaceutically acceptable salt, hydrate, or prodrug thereof, wherein

R1 is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or R1 together with R2 form a heterocyclic ring having 4 to 8 ring members with at least one heteroatom selected from nitrogen;

R2 is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or R1 together with R2 form a heterocyclic ring having 4 to 8 ring members with at least one heteroatom selected from nitrogen;

R3 is H, acyl, alkyl, alkenyl, alkynyl, aralkyl, cycloalkyl, carboxyl, or C-amido; or R3 together with R4 and the atoms to which they are attached form a heterocyclic ring having 4 to 8 ring members with at least two heteroatoms selected from oxygen;

R4 is H, acyl, alkyl, alkenyl, alkynyl, aralkyl, cycloalkyl, carboxyl, or C-amido; or R3 together with R4 and the atoms to which they are attached form a heterocyclic ring having 4 to 8 ring members with at least two heteroatoms selected from oxygen;

$R_5$ is oxo, hydroxyl, alkyl, alkenyl, alkynyl, OR", or is absent; wherein R" is selected from alkyl, alkenyl, alkynyl, cycloalkyl, aryl, or aralkyl;

$R_6$ is oxo, hydroxyl, alkyl, alkenyl, alkynyl, OR", or is absent; wherein R" is selected from alkyl, alkenyl, alkynyl, cycloalkyl, aryl, or aralkyl;

$R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan; and $R_8$ is hydrogen, azido, alkyl, alkenyl, or alkynyl, wherein Formula (II) is:

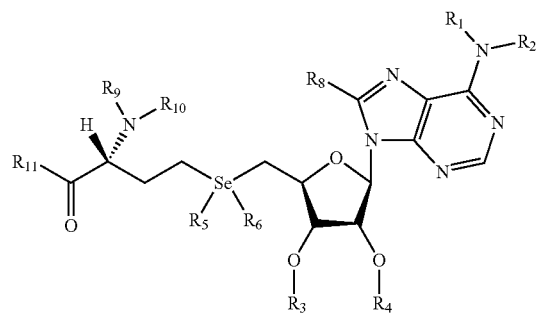

(II)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR", or is absent; wherein R" is selected from alkyl, alkenyl, alkynyl, cycloalkyl, aryl, or aralkyl;

$R_6$ is oxo, hydroxyl, alkyl, alkenyl, alkynyl, OR", or is absent; wherein R" is selected from alkyl, alkenyl, alkynyl, cycloalkyl, aryl, or aralkyl;

$R_8$ is hydrogen, azido, alkyl, alkenyl, or alkynyl;

$R_9$ is H, acyl, alkyl, alkenyl, alkynyl, aralkyl, carboxyl, cycloalkyl, $C(O)R^c$, or $C(O)OR^c$, where $R^c$ is alkyl, cycloalkyl, aryl, aralkyl, or heterocyclyl; or $R_9$ together with $R_{10}$ form a heterocyclic ring having 4 to 8 ring members with at least one heteroatom selected from nitrogen;

$R_{10}$ is H, acyl, alkyl, alkenyl, alkynyl, aralkyl, carboxyl, cycloalkyl, $C(O)R^c$, or $C(O)OR^c$, where $R^c$ is selected from alkyl, cycloalkyl, aryl, aralkyl, or heterocyclyl; or $R_9$ together with $R_{10}$ form a heterocyclic ring having 4 to 8 ring members with at least one heteroatom selected from nitrogen; and $R_{11}$ is OR, alkoxy, aralkoxy, or amino, where R is selected from alkyl, cycloalkyl, aryl, aralkyl, or heterocyclyl, and wherein Formula (III) is:

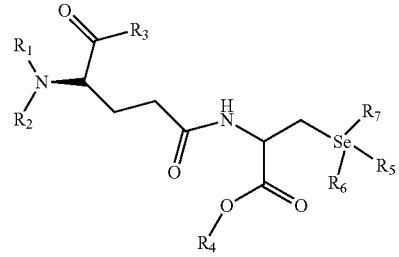

(III)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is OH, OR, alkoxy, aralkoxy, or amino, where R is selected from alkyl, cycloalkyl, aryl, aralkyl, or heterocyclyl;

$R_4$ is alkyl, alkenyl, alkynyl, cycloalkyl, aryl, aralkyl, or heterocyclyl;

$R_5$ is oxo, hydroxyl, alkyl, alkenyl, alkynyl, OR", or is absent; wherein R" is selected from alkyl, alkenyl, alkynyl, cycloalkyl, aryl, or aralkyl;

$R_6$ is oxo, hydroxyl, alkyl, alkenyl, alkynyl, OR", or is absent; wherein R" is selected from alkyl, alkenyl, alkynyl, cycloalkyl, aryl, or aralkyl; and $R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

6. The method of claim 1, wherein the composition comprises 5'-Methylselenoadenosine, Se-Adenosyl-L-homocysteine and Gamma-glutamyl-methylseleno-cysteine.

7. The method of claim 2, wherein the composition comprises 5'-Methylselenoadenosine, Se-Adenosyl-L-homocysteine and Gamma-glutamyl-methylseleno-cysteine.

8. The method of claim 3, wherein the composition comprises 5'-Methylselenoadenosine, Se-Adenosyl-L-homocysteine and Gamma-glutamyl-methylseleno-cysteine.

9. The method of claim 4, wherein the composition comprises 5'-Methylselenoadenosine, Se-Adenosyl-L-homocysteine and Gamma-glutamyl-methylseleno-cysteine.

10. The method of claim 5, wherein the composition comprises 5'-Methylselenoadenosine, Se-Adenosyl-L-homocysteine and Gamma-glutamyl-methylseleno-cysteine.

11. The method of claim 1, wherein the composition comprises at least 0.1% (w/v) of 5'-Methylselenoadenosine.

12. The method of claim 2, wherein the composition comprises at least 0.1% (w/v) of 5'-Methylselenoadenosine.

13. The method of claim 3, wherein the composition comprises at least 0.1% (w/v) of 5'-Methylselenoadenosine.

14. The method of claim 4, wherein the composition comprises at least 0.1% (w/v) of 5'-Methylselenoadenosine.

15. The method of claim 5, wherein the composition comprises at least 0.1% (w/v) of 5'-Methylselenoadenosine.

16. The method of claim 1, wherein the composition further comprises insulin or an analog or derivative thereof.

17. The method of claim 2, wherein the composition further comprises insulin or an analog or derivative thereof.

18. The method of claim 3, wherein the composition further comprises insulin or an analog or derivative thereof.

19. The method of claim 4, wherein the composition further comprises insulin or an analog or derivative thereof.

20. The method of claim 5, wherein the composition further comprises insulin or an analog or derivative thereof.

21. The method of claim 1, wherein the composition further comprises an insulin sensitizer, an insulin secretagogue, or an incretin mimetic.

22. The method of claim 2, wherein the composition further comprises an insulin sensitizer, an insulin secretagogue, or an incretin mimetic.

23. The method of claim 3, wherein the composition further comprises an insulin sensitizer, an insulin secretagogue, or an incretin mimetic.

24. The method of claim 4, wherein the composition further comprises an insulin sensitizer, an insulin secretagogue, or an incretin mimetic.

25. The method of claim 1, wherein the composition excludes one or more of 5'-Methylthioadenosine, S-Adenosyl-L-homocysteine or Gamma-glutamyl-methyl-cysteine.

26. The method of claim 2, wherein the composition excludes one or more of 5'-Methylthioadenosine, S-Adenosyl-L-homocysteine or Gamma-glutamyl-methyl-cysteine.

27. The method of claim 3, wherein the composition excludes one or more of 5'-Methylthioadenosine, S-Adenosyl-L-homocysteine or Gamma-glutamyl-methyl-cysteine.

28. The method of claim 4, wherein the composition excludes one or more of 5'-Methylthioadenosine, S-Adenosyl-L-homocysteine or Gamma-glutamyl-methyl-cysteine.

29. The method of claim 5, wherein the composition excludes one or more of 5'-Methylthioadenosine, S-Adenosyl-L-homocysteine or Gamma-glutamyl-methyl-cysteine.

30. A composition comprising at least two different compounds selected from the group consisting of 5'-Methylselenoadenosine, Se-Adenosyl-L-homocysteine, Gamma-glutamyl-methylseleno-cysteine, a compound of Formula (I), a compound of Formula (II), and a compound of Formula (III); and a carrier, wherein the composition contains at least about 0.033% (w/v) of each of the at least two different compounds that is selected, wherein Formula (I) is:

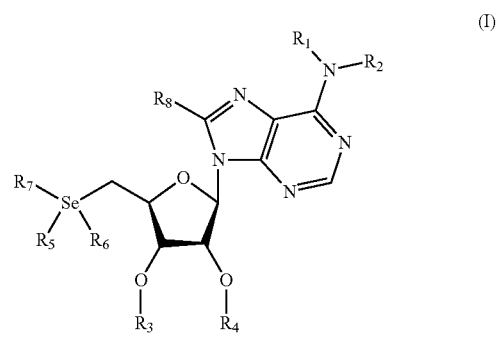

(I)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan; and $R_8$ is hydrogen, azido, alkyl, alkenyl, or alkynyl, wherein Formula (II) is:

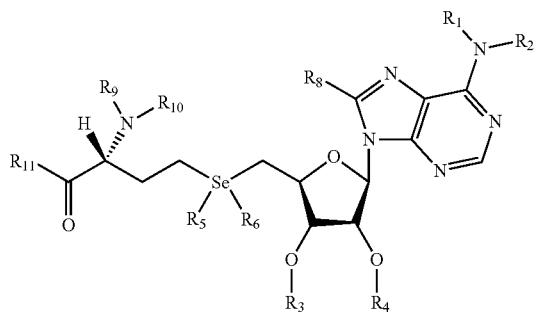

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_8$ is hydrogen, azido, alkyl, alkenyl, or alkynyl;

$R_9$ is H, acyl, alkyl, alkenyl, alkynyl, aralkyl, carboxyl, cycloalkyl, $C(O)R^c$, or $C(O)OR^c$, where $R^c$ is alkyl, cycloalkyl, aryl, aralkyl, or heterocyclyl; or $R_9$ together with $R_{10}$ form a heterocyclic ring having 4 to 8 ring members with at least one heteroatom selected from nitrogen;

$R_{10}$ is H, acyl, alkyl, alkenyl, alkynyl, aralkyl, carboxyl, cycloalkyl, $C(O)R^c$, or $C(O)OR^c$, where $R^c$ is selected from alkyl, cycloalkyl, aryl, aralkyl, or heterocyclyl; or $R_9$ together with $R_{10}$ form a heterocyclic ring having 4 to 8 ring members with at least one heteroatom selected from nitrogen; and $R_{11}$ is OR, alkoxy, aralkoxy, or amino, where R is selected from alkyl, cycloalkyl, aryl, aralkyl, or heterocyclyl, and wherein Formula (III) is:

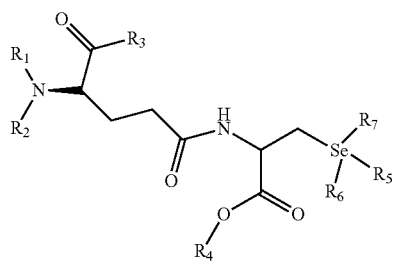

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is OH, OR, alkoxy, aralkoxy, or amino, where R is selected from alkyl, cycloalkyl, aryl, aralkyl, or heterocyclyl;

$R_4$ is alkyl, alkenyl, alkynyl, cycloalkyl, aryl, aralkyl, or heterocyclyl;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl; and $R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

31. A composition comprising at least three different compounds selected from the group consisting of 5'-Methylselenoadenosine, Se-Adenosyl-L-homocysteine, Gamma-glutamyl-methylseleno-cysteine, a compound of Formula (I), a compound of Formula (II), and a compound of Formula (III); and a carrier, wherein the composition contains at least about 0.033% (w/v) of each of the at least three different compounds that is selected, wherein Formula (I) is:

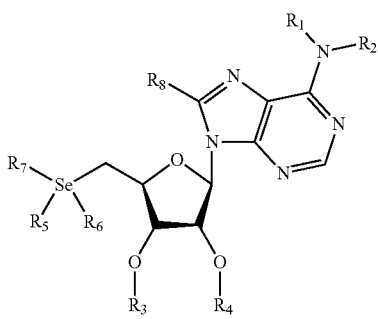

(I)

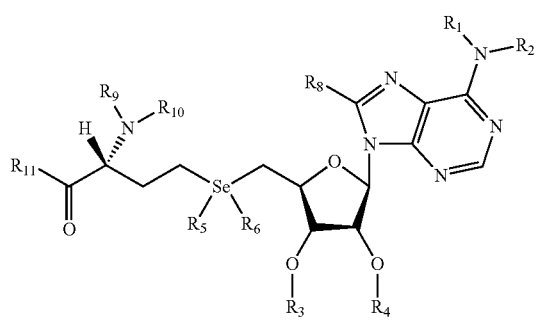

(II)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan; and $R_8$ is hydrogen, azido, alkyl, alkenyl, or alkynyl, wherein Formula (II) is:

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;

$R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least two heteroatoms selected from oxygen;

$R_5$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_6$ is oxo, hydroxyl, alkyl, alkenyl, alkynyl, OR'', or is absent; wherein R'' is selected from alkyl, alkenyl, alkynyl, cycloalkyl, aryl, or aralkyl;

$R_8$ is hydrogen, azido, alkyl, alkenyl, or alkynyl;

$R_9$ is H, acyl, alkyl, alkenyl, alkynyl, aralkyl, carboxyl, cycloalkyl, C(O)$R^c$, or C(O)O$R^c$, where $R^c$ is alkyl, cycloalkyl, aryl, aralkyl, or heterocyclyl; or $R_9$ together with $R_{10}$ form a heterocyclic ring having 4 to 8 ring members with at least one heteroatom selected from nitrogen;

$R_{10}$ is H, acyl, alkyl, alkenyl, alkynyl, aralkyl, carboxyl, cycloalkyl, C(O)$R^c$, or C(O)O$R^c$, where $R^c$ is selected from alkyl, cycloalkyl, aryl, aralkyl, or heterocyclyl; or $R_9$ together with $R_{10}$ form a heterocyclic ring having 4 to 8 ring members with at least one heteroatom selected from nitrogen; and $R_{11}$ is OR, alkoxy, aralkoxy, or amino, where R is selected from alkyl, cycloalkyl, aryl, aralkyl, or heterocyclyl, and wherein Formula (III) is:

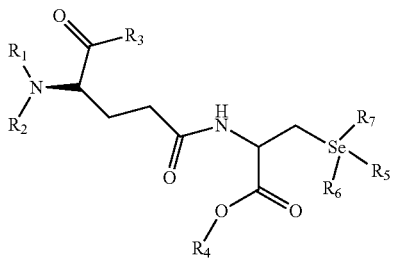

(III)

or a pharmaceutically acceptable salt, hydrate, or prodrug thereof, wherein
- $R_1$ is H, acyl, alkyl, alkenyl, alkynyl, aralkyl, carboxyl, cycloalkyl, C(O)R', or C(O)OR', wherein R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from nitrogen;
- $R_2$ is H, acyl, alkyl, alkenyl, alkynyl, aralkyl, carboxyl, cycloalkyl, C(O)R''', or C(O)OR''', wherein R''' is selected from alkyl, cycloalkyl, aryl, aralkyl, or heterocyclyl; or $R_1$ together with $R_2$ form a heterocyclic ring having 4 to 8 ring members with at least one heteroatom selected from nitrogen;
- $R_3$ is OH, OR, alkoxy, aralkoxy, or amino, where R is selected from alkyl, cycloalkyl, aryl, aralkyl, or heterocyclyl;
- $R_4$ is alkyl, alkenyl, alkynyl, cycloalkyl, aryl, aralkyl, or heterocyclyl;
- $R_5$ is oxo, hydroxyl, alkyl, alkenyl, alkynyl, OR'', or is absent; wherein R'' is selected from alkyl, alkenyl, alkynyl, cycloalkyl, aryl, or aralkyl;
- $R_6$ is oxo, hydroxyl, alkyl, alkenyl, alkynyl, OR'', or is absent; wherein R'' is selected from alkyl, alkenyl, alkynyl, cycloalkyl, aryl, or aralkyl; and
- $R_7$ is a $C_3$-$C_{16}$ alkyl, alkenyl, alkynyl, ketone, amino alcohol, amino acid, $OR^a$, Se—$R^b$, or S—$R^b$, wherein $R^a$ for $OR^a$ is selected from the group consisting of H, alkyl, cycloalkyl, aryl, aralkyl, and heterocyclyl, where $R^b$ for Se—$R^b$ is selected from the group consisting of H, $C_3$-$C_{16}$ alkyl, cycloalkyl, aryl, aralkyl, and heterocyclyl, wherein $R^b$ for S—$R^b$ is selected from the group consisting of H, $C_3$-$C_{16}$ alkyl, cycloalkyl, aryl, aralkyl, and heterocyclyl, and wherein the amino acid is selected from the group consisting of arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, and tryptophan.

32. The composition of claim 30, wherein a compound according to the Formula (I) is included in the at least two different compounds that are selected.

33. The composition of claim 30, wherein a compound according to the Formula (II) is included in the at least two different compounds that are selected.

34. The composition of claim 30, wherein a compound according to the Formula (III) is included in the at least two different compounds that are selected.

* * * * *